(12) United States Patent
Fortte et al.

(10) Patent No.: US 10,351,557 B2
(45) Date of Patent: Jul. 16, 2019

(54) COMPOUNDS FOR ELECTRONIC DEVICES

(75) Inventors: Rocco Fortte, Frankfurt (DE); Christof Pflumm, Darmstadt (DE); Constanze Brocke, Gross-Gerau (DE); Amir Hossain Parham, Frankfurt am Main (DE)

(73) Assignee: Merck Patent GmbH (DE)

( * ) Notice: Subject to any disclaimer, the term of this patent is extended or adjusted under 35 U.S.C. 154(b) by 733 days.

(21) Appl. No.: 13/704,487

(22) PCT Filed: May 23, 2011

(86) PCT No.: PCT/EP2011/002547
§ 371 (c)(1),
(2), (4) Date: Dec. 14, 2012

(87) PCT Pub. No.: WO2011/157346
PCT Pub. Date: Dec. 22, 2011

(65) Prior Publication Data
US 2013/0092879 A1  Apr. 18, 2013

(30) Foreign Application Priority Data
Jun. 18, 2010  (DE) .................. 10 2010 024 335

(51) Int. Cl.
| | |
|---|---|
| H01L 51/00 | (2006.01) |
| C07D 471/04 | (2006.01) |
| C07D 251/24 | (2006.01) |
| C07D 403/04 | (2006.01) |
| C07D 471/02 | (2006.01) |
| C07D 471/14 | (2006.01) |
| C07D 491/052 | (2006.01) |
| C09K 11/06 | (2006.01) |
| H01L 51/50 | (2006.01) |

(52) U.S. Cl.
CPC ......... *C07D 471/04* (2013.01); *C07D 251/24* (2013.01); *C07D 403/04* (2013.01); *C07D 471/02* (2013.01); *C07D 471/14* (2013.01); *C07D 491/052* (2013.01); *C09K 11/06* (2013.01); *H01L 51/0032* (2013.01); *H01L 51/0035* (2013.01); *H01L 51/0072* (2013.01); *C09K 2211/1007* (2013.01); *C09K 2211/1011* (2013.01); *C09K 2211/1029* (2013.01); *C09K 2211/1059* (2013.01); *C09K 2211/1088* (2013.01); *H01L 51/0077* (2013.01); *H01L 51/0085* (2013.01); *H01L 51/5016* (2013.01); *H01L 51/5056* (2013.01); *H01L 51/5072* (2013.01); *Y02E 10/549* (2013.01)

(58) Field of Classification Search
CPC .................................................. H01L 51/0072
USPC ....................................................... 252/500
See application file for complete search history.

(56) References Cited

U.S. PATENT DOCUMENTS

| | | | |
|---|---|---|---|
| 3,106,563 A | 10/1963 | Schmidt-Nickels | |
| 3,167,557 A | 1/1965 | Klemm et al. | |
| 3,244,719 A | 4/1966 | Braun et al. | |
| 3,764,690 A * | 10/1973 | Draber et al. | 514/341 |
| 8,241,763 B2 * | 8/2012 | Buesing | C07C 13/62 |
| | | | 257/40 |
| 2005/0101660 A1 * | 5/2005 | Lee | A61K 31/335 |
| | | | 514/452 |
| 2009/0261717 A1 | 10/2009 | Buesing et al. | |

FOREIGN PATENT DOCUMENTS

| | | |
|---|---|---|
| GB | 627519 A | 8/1949 |
| JP | 2000315579 A | 11/2000 |
| JP | 2008-500958 A | 1/2008 |
| WO | WO-2008006449 A1 | 1/2008 |
| WO | WO-2010064871 A1 | 6/2010 |
| WO | WO-2011021803 A2 | 2/2011 |

OTHER PUBLICATIONS

Meesala et al, "A rapid and efficient entry to synthesis of quino and chromenocarbazoles," Tetrahedron, 65 (2009) 6050-6056.*
Sato, Ryu, et al, Heterocycles, 1988, 27(11), pp. 2563-2566.*
Warner, Philip M., J. Am. Chem. Soc., 1994, 116, 11059-11066.*
Meesala, Ramu, et al., "A Rapid and Efficient Entry to Synthesis of Quino and Chromenocarbazoles via Ullmann-Goldberg Condensation", Tetrahedron, vol. 65, (2009), pp. 6050-6056.
(Continued)

*Primary Examiner* — William D Young
(74) *Attorney, Agent, or Firm* — Drinker Biddle & Reath LLP

(57) ABSTRACT

The present invention relates to compounds of the formula (I),

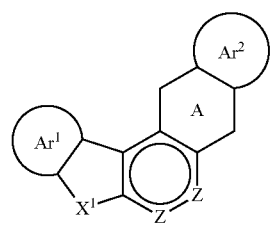

to the use of compounds of the formula (I) in electronic devices, and to electronic devices containing one or more compounds of the formula (I). The invention furthermore relates to preparation processes for compounds of the formula (I) and to formulations comprising one or more compounds of the formula (I).

9 Claims, No Drawings

(56) References Cited

OTHER PUBLICATIONS

Xu, Xiufang, et al., "Systematic Investigation of the Molecular Behaviors of Heterofullerenes C48X2 (X=B, N)", Chemical Physics, vol. 287, (2003), pp. 317-333.
Caplus Database; XP-002649598; 1989.
Caplus Database; XP-002649599; (1992).
Sun, Lijun, et al., "The Regiospecific Synthesis of Angularly-Fused Xanthones via the Benzannulation of 1,2-Adducts Derived from 3-(o-Anisoyl)-4-Substituted Cyclobutenediones and their Dithianyl Derivatives", Tetrahedron Letters, vol. 38, No. 21, (1997), pp. 3663-3666.
International Search Report for PCT/EP2011/002547 dated Oct. 28, 2011.
Kitahara et al., "Synthesis of Indole Rings Fused Quinacridones", Journal of the Chemical Society of Japan,vol. 1992, Issue 6 (1992) pp. 662-666 [Previously cited the Abstract only on Dec. 14, 2012— Caplus Database: XP-002649599: (1992)].

* cited by examiner

COMPOUNDS FOR ELECTRONIC DEVICES

CROSS-REFERENCE TO RELATED APPLICATIONS

This application is a national stage application (under 35 U.S.C. § 371) of PCT/EP2011/002547, filed May 23, 2011, which claims benefit of German application 10 2010 024 335.3, filed June 18, 2010 which are both incorporated by reference.

The present invention relates to compounds of the formula (I), to the use of compounds of the formula (I) in electronic devices, and to electronic devices comprising one or more compounds of the formula (I). The invention furthermore relates to preparation processes for compounds of the formula (I) and to formulations comprising one or more compounds of the formula (I).

Organic semiconductor materials, such as the compounds according to the invention, are being developed for a number of different applications in electronic devices.

The structure of organic electroluminescent devices (OLEDs) in which the compounds according to the invention can be employed as functional materials is described, for example, in U.S. Pat. Nos. 4,539,507, 5,151,629, EP 0676461 and WO 98/27136.

Further improvements are still necessary with respect to the performance data of the organic electroluminescent devices, in particular with a view to broad commercial use. Of particular importance in this connection are the lifetime, the efficiency and the operating voltage of the organic electroluminescent devices and the colour values achieved. In particular in the case of blue-emitting electroluminescent devices, there is potential for improvement with respect to the lifetime of the devices.

In addition, it is desirable for the compounds for use as organic semiconductor materials to have high thermal stability and a high glass-transition temperature and to be sublimable without decomposition.

In this connection there is, inter alia, a demand for alternative hole-transport materials. In the case of hole-transport materials in accordance with the prior art, the voltage generally increases with the layer thickness of the hole-transport layer. In practice, a greater layer thickness of the hole-transport layer would frequently be desirable, but this often has the consequence of a higher operating voltage and worse performance data. In this connection, there is a demand for novel hole-transport materials which have high charge-carrier mobility, enabling thicker hole-transport layers to be achieved with just a slight increase in the operating voltage.

Arylamine derivatives are known from the prior art as hole-transport and hole-injection materials. Materials of this type based on indenofluorenes are disclosed, for example, in WO 06/100896 and WO 06/122630. The indenofluorenamines described above have disadvantages in processability: during the vapour-deposition or coating process, premature deposition and thus complication of the industrial process may occur. In addition, the known hole-transporting materials frequently have low electron stability, which results in short lifetimes of the electronic devices comprising the compounds. There continues to be a need for improvement here.

Furthermore, there is a demand for alternative matrix materials for use in electronic devices. In particular, there is a demand for matrix materials for phosphorescent emitters which simultaneously result in good efficiency, a long lifetime and a low operating voltage. It is precisely the properties of the matrix materials that are frequently limiting for the lifetime and efficiency of the organic electroluminescent device.

In accordance with the prior art, carbazole derivatives, for example bis-(carbazolyl)biphenyl, are frequently used as matrix materials. There is still potential for improvement here, in particular with respect to the lifetime and glass-transition temperature of the materials. There continues to be a need for improvement with respect to the operating voltage of the electronic devices comprising the materials in question.

Furthermore, ketones (WO 04/093207), phosphine oxides, sulfones (WO 05/003253) and triazine compounds, such as triazinylspirobifluorene (cf. the applications WO 05/053055 and WO 10/015306), are used as matrix materials for phosphorescent emitters. In particular with ketones, low operating voltages and long lifetimes are achieved. There is still potential for improvement here, in particular with respect to the efficiency and compatibility with metal complexes which contain ketoketonate ligands, for example acetylacetonate.

Metal complexes, for example BAlq or zinc(II) bis[2-(2-benzothiazolyl)-phenolate], are furthermore used as matrix materials for phosphorescent emitters. There is still a need for improvement here, in particular with respect to the operating voltage and chemical stability. Purely organic compounds are frequently more stable than these metal complexes. Thus, some of these metal complexes are hydrolysis-sensitive, which makes handling the complexes more difficult.

Also of particular interest is the provision of alternative materials as matrix components of mixed-matrix systems. A mixed-matrix system in the sense of this application is taken to mean a system in which two or more different matrix compounds are used mixed together with one (or more) dopant compounds as the emitting layer. These systems are, in particular, of interest in the case of phosphorescent organic electroluminescent devices. For more detailed information, reference is made to the application WO 10/108579.

Compounds known from the prior art which may be mentioned as matrix components in mixed-matrix systems are, inter alia, CBP (biscarbazolylbiphenyl) and TCTA (triscarbazolyltriphenylamine). However, there continues to be a demand for alternative compounds for use as matrix components in mixed-matrix systems. In particular, there is a demand for compounds which effect an improvement in the operating voltage and lifetime of the electronic devices.

The applications WO 10/136109 and WO 11/000455 disclose indenocarbazole and indolocarbazole derivatives having different linking geometry of the indene or indole and carbazole units. The compounds are very highly suitable for use as functional materials in organic electroluminescent devices, in particular as matrix materials for phosphorescent emitters and as electron-transport materials. However, there continues to be a demand for alternative compounds, in particular those by means of which a reduction in the operating voltage, an increase in the power efficiency and an increase in the lifetime can be achieved.

Furthermore, EP 1860097, WO 2006/100896, WO 2007/140847, WO 2006/122630 and WO 2008/006449 disclose indenofluorenediamine derivatives for use in electronic devices, in particular as hole-transport materials. However, there continues to be a demand for alternative compounds, in particular those by means of which a reduction in the operating voltage, an increase in the power efficiency and an increase in the lifetime can be achieved.

The present invention describes, as a novel class of materials, compounds of the formula (I) which exhibit advantageous properties on use in electronic devices, preferably organic electroluminescent devices. The compounds are preferably used as hole-transport or hole-injection materials, as matrix materials for fluorescent or phosphorescent emitters or as electron-transport materials.

The invention thus relates to compounds of the formula (I)

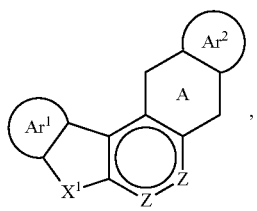

formula (I)

where

represents a group of the formula

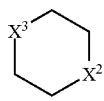

or a group of the formula

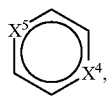

and where the symbols occurring are as defined below:

$X^1$, $X^2$, $X^3$ are on each occurrence a divalent group selected, identically or differently, from $BR^1$, $C(R^1)_2$, $Si(R^1)_2$, C=O, C=NR$^1$, C=C(R$^1$)$_2$, NR$^1$, O, S, S=O, S(=O)$_2$, PR$^1$ and P(=O)R$^1$;

$X^4$, $X^5$ are on each occurrence selected, identically or differently, from $CR^1$, N and P;

Z is on each occurrence selected, identically or differently, from $CR^1$ and N;

$Ar^1$, $Ar^2$ are on each occurrence, identically or differently, an aryl group having 6 to 60 aromatic ring atoms or a heteroaryl group having 5 to 60 aromatic ring atoms, each of which may be substituted by one or more radicals $R^2$;

$R^1$, $R^2$ are on each occurrence, identically or differently, H, D, F, Cl, Br, I, B(OR$^3$)$_2$, CHO, C(O)R$^3$, CR$^3$=C(R$^3$)$_2$, CN, COOR$^3$, CON(R$^3$)$_2$, Si(R$^3$)$_3$, N(R$^3$)$_2$, NO$_2$, P(=O)(R$^3$)$_2$, OSO$_2$R$^3$, OH, S(=O)R$^3$, S(=O)$_2$R$^3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^3$, where one or more CH$_2$ groups may be replaced by —R$^3$C=CR$^3$—, —C≡C—, Si(R$^3$)$_2$, Ge(R$^3$)$_2$, Sn(R$^3$)$_2$, C=O, C=S, C=Se, C=NR$^3$, —COO—, —CONR$^3$—, NR$^3$, P(=O)(R$^3$), —O—, —S—, SO or SO$_2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^3$, or an aryloxy, heteroaryloxy, aralkyl or heteroaralkyl group having 5 to 60 aromatic ring atoms, which may be substituted by one or more radicals R$^3$, or a combination of these systems, where two or more radicals R$^1$ or R$^2$ may be linked to one another and may form an aliphatic or aromatic ring system;

$R^3$ is on each occurrence, identically or differently, H, D, F, Cl, Br, I, B(OR$^4$)$_2$, CHO, C(O)R$^4$, CR$^4$=C(R$^4$)$_2$, CN, COOR$^4$, CON(R$^4$)$_2$, Si(R$^4$)$_3$, N(R$^4$)$_2$, NO$_2$, P(=O)(R$^4$)$_2$, OSO$_2$R$^4$, OH, S(=O)R$^4$, S(=O)$_2$R$^4$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^4$, where one or more CH$_2$ groups may be replaced by —R$^4$C=CR$^4$—, —C≡C—, Si(R$^4$)$_2$, Ge(R$^4$)$_2$, Sn(R$^4$)$_2$, C=O, C=S, C=Se, C=NR$^4$, —COO—, —CONR$^4$—, NR$^4$, P(=O)(R$^4$), —O—, —S—, SO or SO$_2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^4$, or an aryloxy or heteroaryloxy group having 5 to 60 aromatic ring atoms, which may be substituted by one or more radicals R$^4$, or a combination of these systems, where two or more radicals R$^3$ may be linked to one another and may form an aliphatic or aromatic ring system;

$R^4$ is, identically or differently on each occurrence, H, D, F or an aliphatic, aromatic and/or heteroaromatic organic radical having 1 to 20 C atoms, in which, in addition, one or more H atoms may be replaced by D or F; two or more identical or different substituents R$^4$ here may also be linked to one another and form an aliphatic or aromatic ring system;

where it is excluded that $X^2$ and $X^3$ simultaneously represent a group of the formula C=O, and where it is furthermore excluded that $X^4$ and $X^5$ simultaneously represent a group of the formula $CR^1$, and where the following compounds are furthermore excluded:

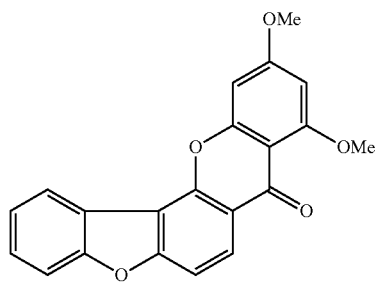

-continued

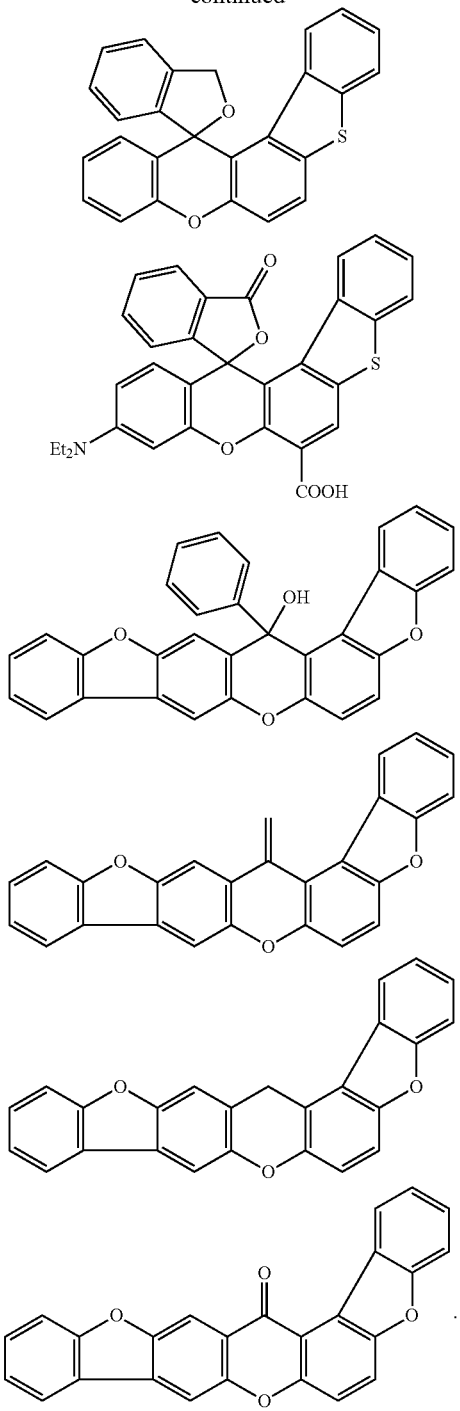

For reasons of clarity, it should be emphasised that, for the purposes of this application, an aromatic or heteroaromatic ring may be represented by a central circle in the ring as an alternative to the classical Lewis notation.

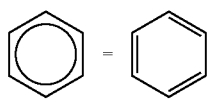

The groups

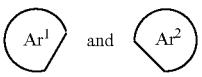

occurring in formula (I) furthermore denote a group $Ar^1$ or $Ar^2$ as defined above which is fused to the five-membered ring or six-membered ring in question, so that it forms with the five-membered ring or six-membered ring a joint condensed aryl or heteroaryl group or a joint aromatic or heteroaromatic ring system.

An aryl group in the sense of this invention contains 6 to 60 C atoms; a heteroaryl group in the sense of this invention contains 1 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

An aryl or heteroaryl group, which may in each case be substituted by the above-mentioned radicals $R^1$ or $R^2$ and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aralkyl group in the sense of this invention is an alkyl group which is substituted by an aryl group, where the term aryl group is to be understood as defined above and the alkyl group has 1 to 20 C atoms, where individual H atoms and/or $CH_2$ groups in the alkyl group may also be replaced by the groups mentioned above under the definition of $R^1$ and $R^2$ and where the alkyl group represents the group which is bonded to the remainder of the compound. Correspondingly, a heteroaralkyl group represents an alkyl group which is substituted by a heteroaryl group, where the term heteroaryl group is to be understood as defined above and the alkyl group has 1 to 20 C atoms, where individual H atoms and/or $CH_2$ groups in the alkyl group may also be replaced by the groups mentioned above under the definition of $R^1$ and $R^2$ and where the alkyl group represents the group which is bonded to the remainder of the compound.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via one or more single bonds are also taken to be aromatic or heteroaromatic ring systems in the sense of this invention.

An aromatic or heteroaromatic ring system having 5-60 aromatic ring atoms, which may also in each case be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals $R^1$ and $R^2$, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

$X^1$, $X^2$ and $X^3$ are preferably selected on each occurrence, identically or differently, from $C(R^1)_2$, C=O, $NR^1$, O and S. $X^1$, $X^2$ and $X^3$ are very particularly preferably selected on each occurrence, identically or differently, from $C(R^1)_2$, $NR^1$, O and S.

Preferred combinations of the groups $X^1$, $X^2$ and $X^3$ are furthermore shown in the following table.

|    | $X^1$ | $X^2$ | $X^3$ |
|----|-------|-------|-------|
| 1  | $C(R^1)_2$ | $C(R^1)_2$ | $C(R^1)_2$ |
| 2  | $C(R^1)_2$ | $C(R^1)_2$ | C=O |
| 3  | $C(R^1)_2$ | $C(R^1)_2$ | $NR^1$ |
| 4  | $C(R^1)_2$ | $C(R^1)_2$ | O |
| 5  | $C(R^1)_2$ | $C(R^1)_2$ | S |
| 6  | $C(R^1)_2$ | C=O | $C(R^1)_2$ |
| 7  | $C(R^1)_2$ | C=O | C=O |
| 8  | $C(R^1)_2$ | C=O | $NR^1$ |
| 9  | $C(R^1)_2$ | C=O | O |
| 10 | $C(R^1)_2$ | C=O | S |
| 11 | $C(R^1)_2$ | $NR^1$ | $C(R^1)_2$ |
| 12 | $C(R^1)_2$ | $NR^1$ | C=O |
| 13 | $C(R^1)_2$ | $NR^1$ | $NR^1$ |
| 14 | $C(R^1)_2$ | $NR^1$ | O |
| 15 | $C(R^1)_2$ | $NR^1$ | S |
| 16 | $C(R^1)_2$ | O | $C(R^1)_2$ |
| 17 | $C(R^1)_2$ | O | C=O |
| 18 | $C(R^1)_2$ | O | $NR^1$ |
| 19 | $C(R^1)_2$ | O | O |
| 20 | $C(R^1)_2$ | O | S |
| 21 | $C(R^1)_2$ | S | $C(R^1)_2$ |
| 22 | $C(R^1)_2$ | S | C=O |
| 23 | $C(R^1)_2$ | S | $NR^1$ |
| 24 | $C(R^1)_2$ | S | O |
| 25 | $C(R^1)_2$ | S | S |
| 26 | C=O | $C(R^1)_2$ | $C(R^1)_2$ |
| 27 | C=O | $C(R^1)_2$ | C=O |
| 28 | C=O | $C(R^1)_2$ | $NR^1$ |
| 29 | C=O | $C(R^1)_2$ | O |
| 30 | C=O | $C(R^1)_2$ | S |
| 31 | C=O | C=O | $C(R^1)_2$ |
| 32 | C=O | C=O | C=O |
| 33 | C=O | C=O | $NR^1$ |
| 34 | C=O | C=O | O |
| 35 | C=O | C=O | S |
| 36 | C=O | $NR^1$ | $C(R^1)_2$ |
| 37 | C=O | $NR^1$ | C=O |
| 38 | C=O | $NR^1$ | $NR^1$ |
| 39 | C=O | $NR^1$ | O |

|     | $X^1$ | $X^2$ | $X^3$ |
| --- | --- | --- | --- |
| 40  | C=O | $NR^1$ | S |
| 41  | C=O | O | $C(R^1)_2$ |
| 42  | C=O | O | C=O |
| 43  | C=O | O | $NR^1$ |
| 44  | C=O | O | O |
| 45  | C=O | O | S |
| 46  | C=O | S | $C(R^1)_2$ |
| 47  | C=O | S | C=O |
| 48  | C=O | S | $NR^1$ |
| 49  | C=O | S | O |
| 50  | C=O | S | S |
| 51  | $NR^1$ | $C(R^1)_2$ | $C(R^1)_2$ |
| 52  | $NR^1$ | $C(R^1)_2$ | C=O |
| 53  | $NR^1$ | $C(R^1)_2$ | $NR^1$ |
| 54  | $NR^1$ | $C(R^1)_2$ | O |
| 55  | $NR^1$ | $C(R^1)_2$ | S |
| 56  | $NR^1$ | C=O | $C(R^1)_2$ |
| 57  | $NR^1$ | C=O | C=O |
| 58  | $NR^1$ | C=O | $NR^1$ |
| 59  | $NR^1$ | C=O | O |
| 60  | $NR^1$ | C=O | S |
| 61  | $NR^1$ | $NR^1$ | $C(R^1)_2$ |
| 62  | $NR^1$ | $NR^1$ | C=O |
| 63  | $NR^1$ | $NR^1$ | $NR^1$ |
| 64  | $NR^1$ | $NR^1$ | O |
| 65  | $NR^1$ | $NR^1$ | S |
| 66  | $NR^1$ | O | $C(R^1)_2$ |
| 67  | $NR^1$ | O | C=O |
| 68  | $NR^1$ | O | $NR^1$ |
| 69  | $NR^1$ | O | O |
| 70  | $NR^1$ | O | S |
| 71  | $NR^1$ | S | $C(R^1)_2$ |
| 72  | $NR^1$ | S | C=O |
| 73  | $NR^1$ | S | $NR^1$ |
| 74  | $NR^1$ | S | O |
| 75  | $NR^1$ | S | S |
| 76  | O | $C(R^1)_2$ | $C(R^1)_2$ |
| 77  | O | $C(R^1)_2$ | C=O |
| 78  | O | $C(R^1)_2$ | $NR^1$ |
| 79  | O | $C(R^1)_2$ | O |
| 80  | O | $C(R^1)_2$ | S |
| 81  | O | C=O | $C(R^1)_2$ |
| 82  | O | C=O | C=O |
| 83  | O | C=O | $NR^1$ |
| 84  | O | C=O | O |
| 85  | O | C=O | S |
| 86  | O | $NR^1$ | $C(R^1)_2$ |
| 87  | O | $NR^1$ | C=O |
| 88  | O | $NR^1$ | $NR^1$ |
| 89  | O | $NR^1$ | O |
| 90  | O | $NR^1$ | S |
| 91  | O | O | $C(R^1)_2$ |
| 92  | O | O | C=O |
| 93  | O | O | $NR^1$ |
| 94  | O | O | O |
| 95  | O | O | S |
| 96  | O | S | $C(R^1)_2$ |
| 97  | O | S | C=O |
| 98  | O | S | $NR^1$ |
| 99  | O | S | O |
| 100 | O | S | S |
| 101 | S | $C(R^1)_2$ | $C(R^1)_2$ |
| 102 | S | $C(R^1)_2$ | C=O |
| 103 | S | $C(R^1)_2$ | $NR^1$ |
| 104 | S | $C(R^1)_2$ | O |
| 105 | S | $C(R^1)_2$ | S |
| 106 | S | C=O | $C(R^1)_2$ |
| 107 | S | C=O | C=O |
| 108 | S | C=O | $NR^1$ |
| 109 | S | C=O | O |
| 110 | S | C=O | S |
| 111 | S | $NR^1$ | $C(R^1)_2$ |
| 112 | S | $NR^1$ | C=O |
| 113 | S | $NR^1$ | $NR^1$ |
| 114 | S | $NR^1$ | O |
| 115 | S | $NR^1$ | S |
| 116 | S | O | $C(R^1)_2$ |
| 117 | S | O | C=O |
| 118 | S | O | $NR^1$ |
| 119 | S | O | O |
| 120 | S | O | S |
| 121 | S | S | $C(R^1)_2$ |
| 122 | S | S | C=O |
| 123 | S | S | $NR^1$ |
| 124 | S | S | O |
| 125 | S | S | S |

It is furthermore particularly preferred for $X^1$ to represent a group of the formula $NR^1$, very particularly preferably a group $NR^1$ in which $R^1$ represents an aromatic or heteroaromatic ring system having 5 to 60 aromatic ring atoms, which may be substituted by one or more radicals $R^3$.

$X^4$ and $X^5$ are furthermore preferably selected on each occurrence, identically or differently, from $CR^1$ and N, where both groups $X^4$ and $X^5$ are not simultaneously equal to $CR^1$. Very particularly preferably, one of the two groups $X^4$ and $X^5$ is equal to $CR^1$ and the other is equal to N. In a still more preferred embodiment, $X^4$ is equal to $CR^1$ and $X^5$ is equal to N.

For compounds of the formula (I), it is preferred that all three groups $X^1$, $X^2$ and $X^3$ do not simultaneously represent O.

For compounds of the formula (I), it is furthermore preferred that all three groups $X^1$, $X^2$ and $X^3$ do not simultaneously represent S.

According to a preferred embodiment, the radical $R^1$ of the group $NR^1$ does not stand for H, D or an alkyl group if one or more of the groups $X^1$, $X^2$ and $X^3$ represent a group of the formula $NR^1$.

According to a particularly preferred embodiment, $R^1$ in $NR^1$ represents a group of the formula $C(O)R^3$, $COOR^3$, $CON(R^3)_2$, $S(=O)R^3$, $S(=O)_2R^3$, or an aromatic or heteroaromatic ring system having 5 to 60 aromatic ring atoms, which may in each case be substituted by one or more radicals $R^3$, or an aryloxy, heteroaryloxy, aralkyl or heteroaralkyl group having 5 to 60 aromatic ring atoms, which may be substituted by one or more radicals $R^3$, or a combination of these systems, if one or more of the groups $X^1$, $X^2$ and $X^3$ represent a group of the formula $NR^1$.

If one or more of the groups $X^1$, $X^2$ and $X^3$ represent a group of the formula $NR^1$, $R^1$ as constituent of the group $NR^1$ very particularly preferably represents an aromatic or heteroaromatic ring system having 5 to 60 aromatic ring atoms, which may be substituted by one or more radicals $R^3$. $R^1$ in this case is still more preferably an aryl or heteroaryl group having 5 to 20 aromatic ring atoms, which may in each case be substituted by one or more radicals $R^3$. Most preferably, $R^1$ in $NR^1$ which stands for $X^1$, $X^2$ and/or $X^3$ is selected from phenyl, biphenyl, terphenyl, quaterphenyl, naphthyl, anthracenyl, pyrenyl, phenanthrenyl, benzanthracenyl, perylenyl, fluoranthenyl, benzimidazolyl, pyridyl, pyrimidyl, pyrazinyl, pyridazinyl and triazinyl, where the said groups may each be substituted by one or more radicals $R^3$.

According to a further preferred embodiment, $Ar^1$ and $Ar^2$ represent on each occurrence, independently of one another, an aryl or heteroaryl group having 5 to 40, particularly preferably having 5 to 20, aromatic ring atoms.

In a further preferred embodiment of the invention, $R^1$ and $R^2$ is on each occurrence, identically or differently, H, D, F, CN, $Si(R^3)_3$, $N(R^3)_2$ or a straight-chain alkyl or alkoxy group having 1 to 20 C atoms or a branched or cyclic alkyl or alkoxy group having 3 to 20 C atoms, each of which may be substituted by one or more radicals $R^3$, where one or more $CH_2$ groups may be replaced by —C≡C—, —$R^3$C=C$R^3$—, Si($R^3$)$_2$, C=O, C=N$R^3$, —N$R^3$—, —O—, —S—, —COO— or —CON$R^3$—, or an aryl or heteroaryl group having 5 to 20 aromatic ring atoms, which may in each case be substituted by one or more radicals $R^3$, where two or more radicals $R^1$ or $R^2$ may be linked to one another and may form an aliphatic or aromatic ring system.

In a further preferred embodiment of the invention, $R^3$ is on each occurrence, identically or differently, H, D, F, CN, Si($R^4$)$_3$, N($R^4$)$_2$ or a straight-chain alkyl or alkoxy group having 1 to 20 C atoms or a branched or cyclic alkyl or alkoxy group having 3 to 20 C atoms, each of which may be substituted by one or more radicals $R^4$, where one or more $CH_2$ groups may be replaced by —C≡C—, —$R^4$C=C$R^4$—, Si($R^4$)$_2$, C=O, C=N$R^4$, —N$R^4$—, —O—, —S—, —COO— or —CON$R^4$—, or an aryl or heteroaryl group having 5 to 20 aromatic ring atoms, which may in each case be substituted by one or more radicals $R^4$, where two or more radicals $R^3$ may be linked to one another and may form an aliphatic or aromatic ring system.

In accordance with the invention, compounds of the formula (I) may conform to one of the two formulae (Ia) or (Ib)

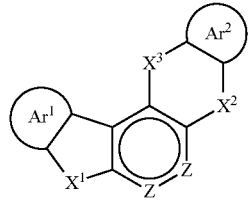

formula (Ia)

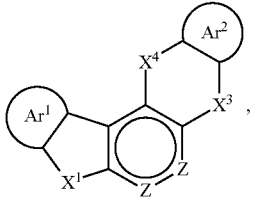

formula (Ib)

where the symbols occurring are as defined above.

It is preferred in accordance with the invention for the groups $Ar^1$ and $Ar^2$ to be selected on each occurrence, identically or differently, from the following groups:

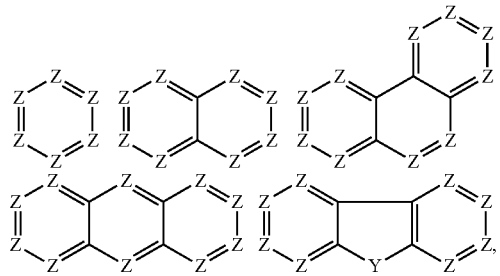

where the groups may be fused to the remainder of the compound via any desired bond Z—Z, where these Z cannot be equal to N, Z is otherwise as defined above, and furthermore Y is selected on each occurrence, identically or differently, from C($R^2$)$_2$, C=O, N$R^2$, O, S, S=O or S(=O)$_2$.

Y is preferably selected from C($R^2$)$_2$, N$R^2$, O and S.

Particularly preferred embodiments of compounds of the formula (I) are compounds of the following formulae (I-1) to (I-56)

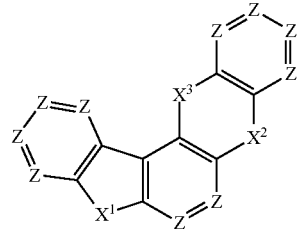

formula (I-1)

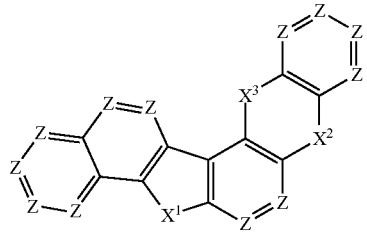

formula (I-2)

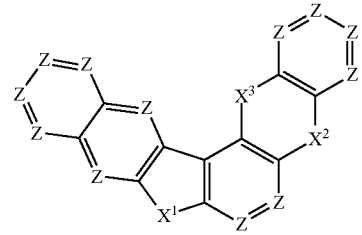

formula (I-3)

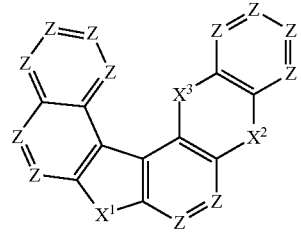

formula (I-4)

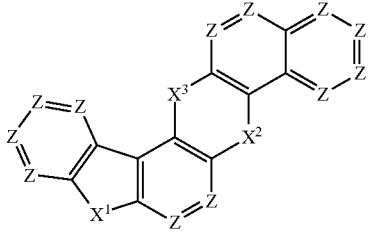

formula (I-5)

formula (I-6)
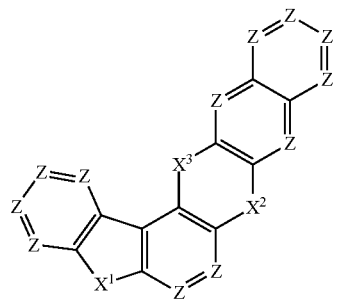
formula (I-7)
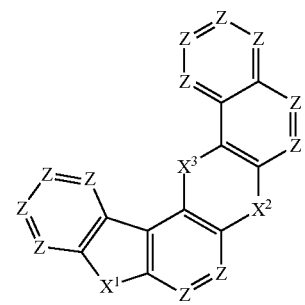
formula (I-8)
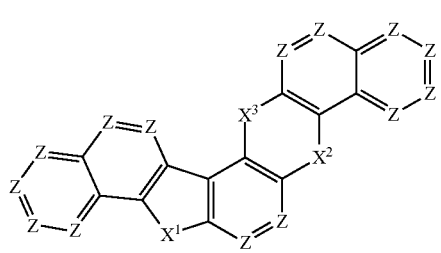
formula (I-9)
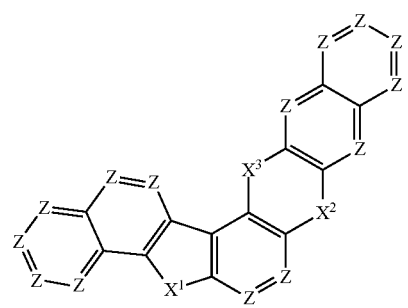
formula (I-10)
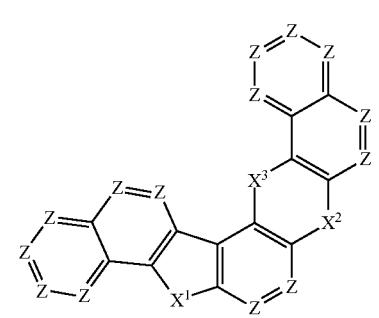
formula (I-11)
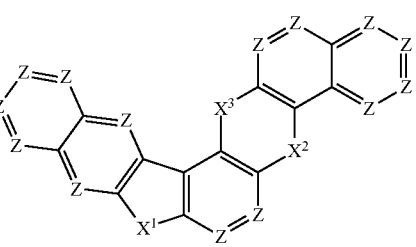
formula (I-12)
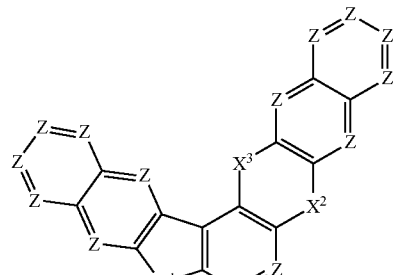
formula (I-13)
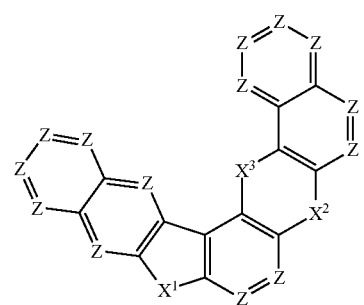
formula (I-14)
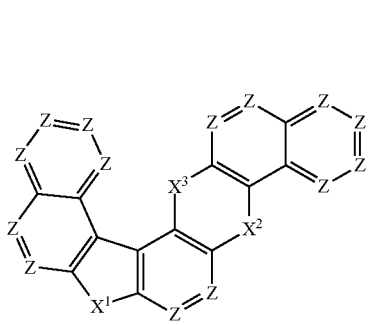
formula (I-15)
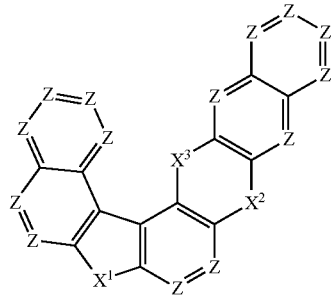

formula (I-16)
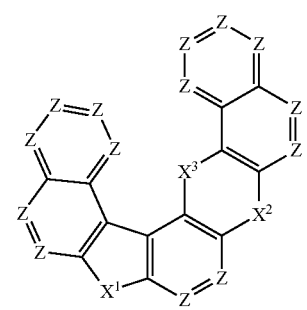
formula (I-17)
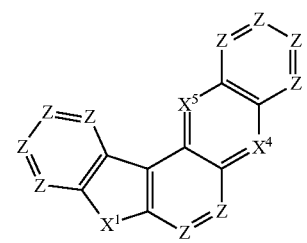
formula (I-18)
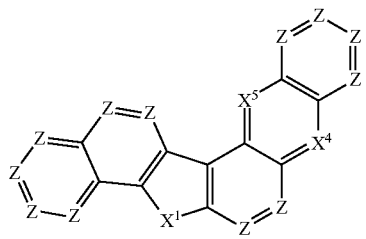
formula (I-19)
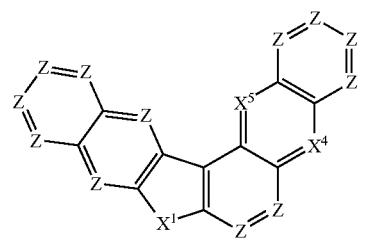
formula (I-20)
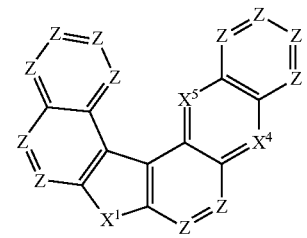
formula (I-21)
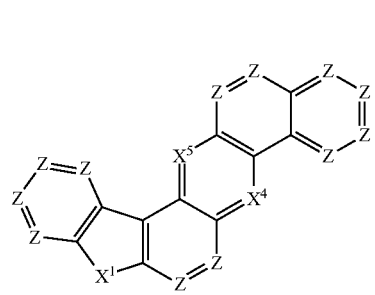
formula (I-22)
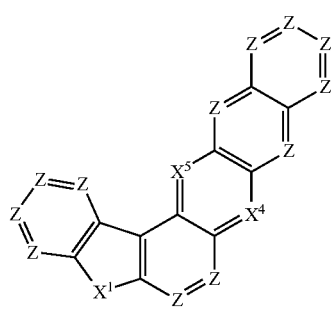
formula (I-23)
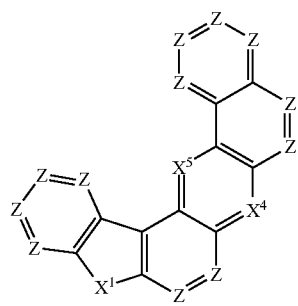
formula (I-24)
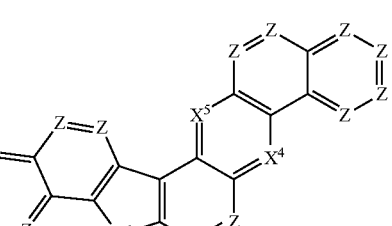
formula (I-25)
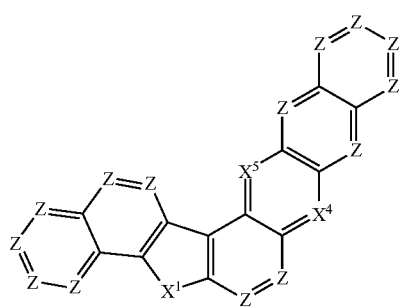
formula (I-26)
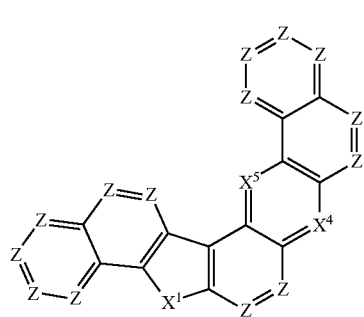

formula (I-27)
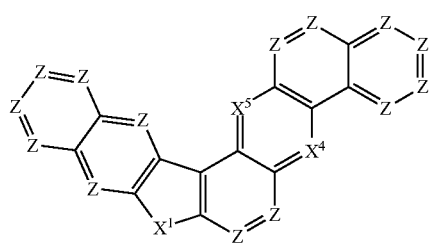
formula (I-28)
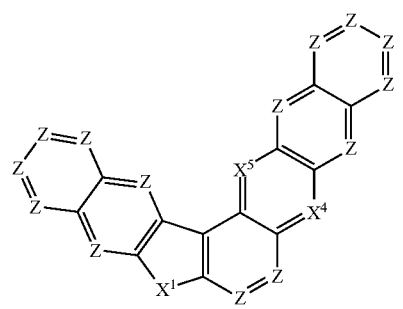
formula (I-29)
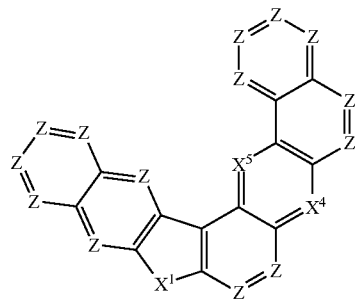
formula (I-30)
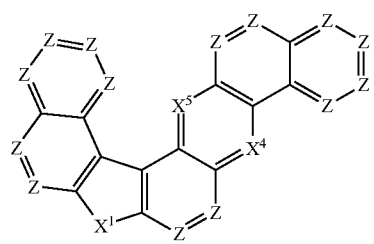
formula (I-31)
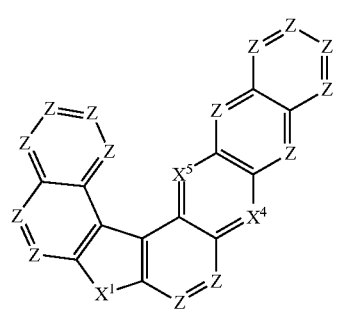
formula (I-32)
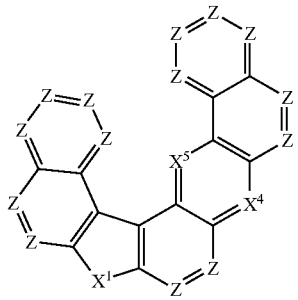
formula (I-33)
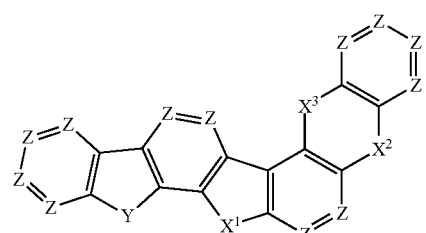
formula (I-34)
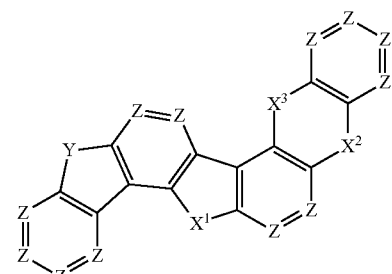
formula (I-35)
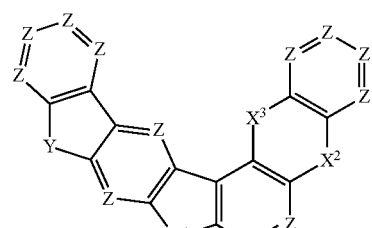
formula (I-36)
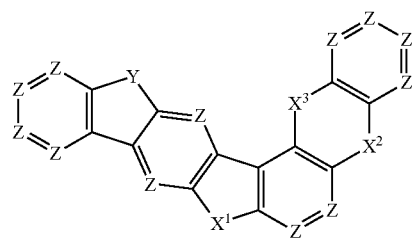
formula (I-37)
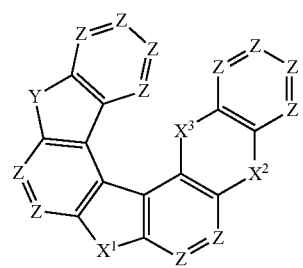

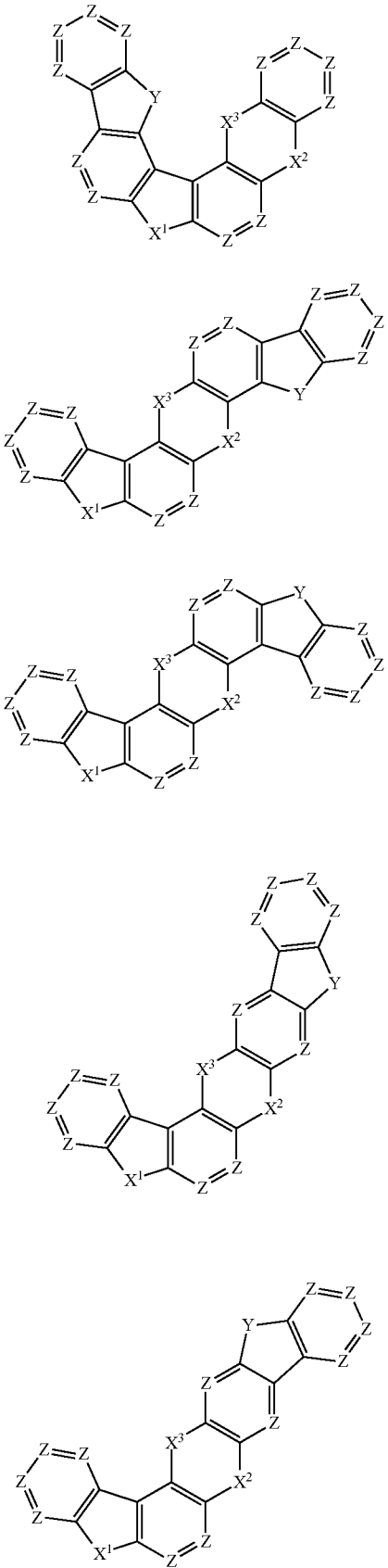
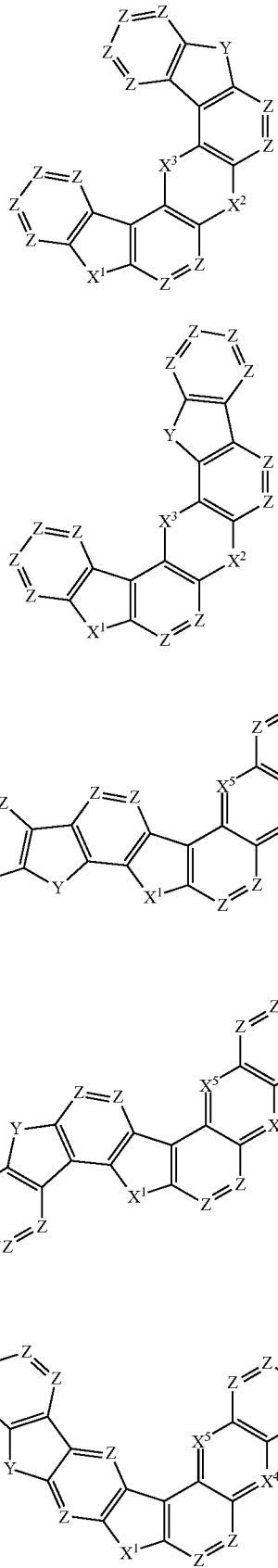

formula (I-48)
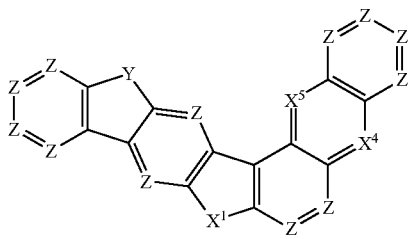

formula (I-49)
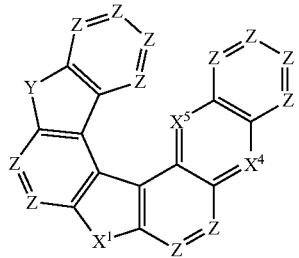

formula (I-50)
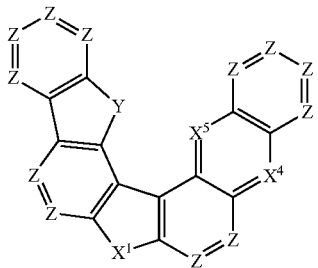

formula (I-51)
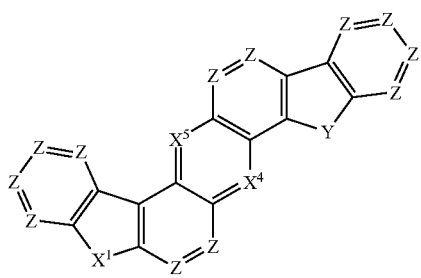

formula (I-52)
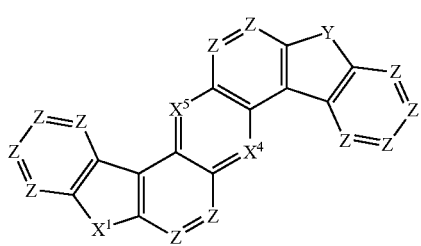

formula (I-53)
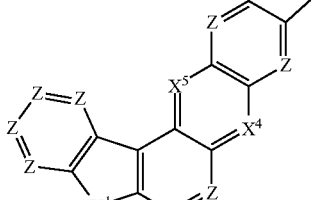

formula (I-54)
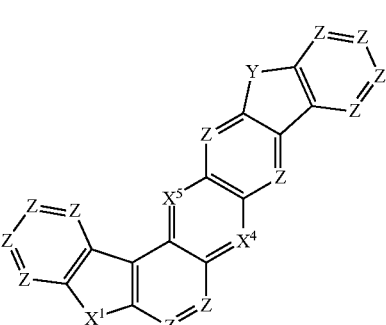

formula (I-55)
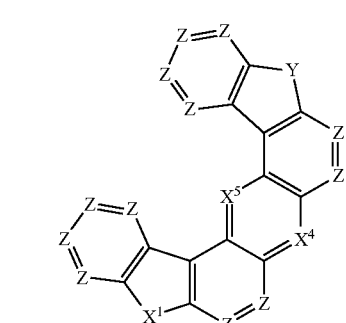

formula (I-56)
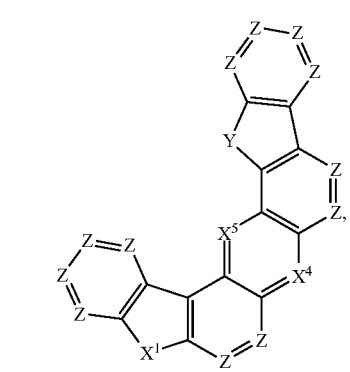

where the groups $X^1$, $X^2$, $X^3$, $X^4$, $X^5$, Z and Y are as defined above.

The compounds according to the invention particularly preferably conform to one of the formulae (I-1) to (I-7) and (I-17) to (I-23) mentioned above.

It is preferred for the compounds according to the invention that not more than two adjacent groups Z are equal to N. It is furthermore preferred that not more than three groups Z per aromatic ring are equal to N and the remaining groups Z are equal to $CR^1$. It is particularly preferred that not more than one group Z per aromatic ring is equal to N and the remaining groups Z are equal to CR¹. Very particularly preferably, all groups Z are equal to CR¹.
Very particular preference is furthermore given to compounds of the following formulae (I-1a) to (I-7a) and (I-17a) to (I-23a)
formula (I-1a)
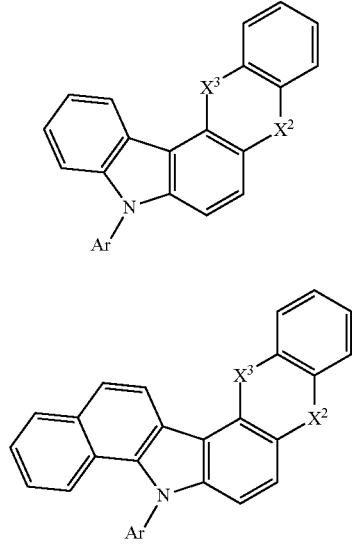
formula (I-2a)
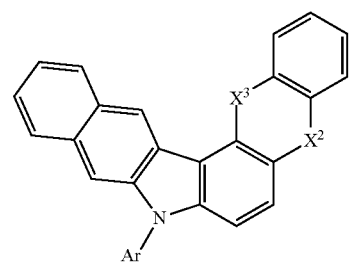
formula (I-3a)
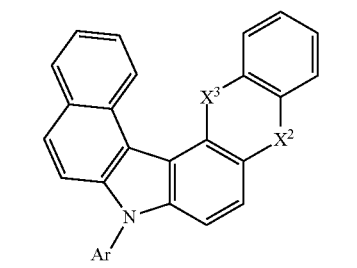
formula (I-4a)
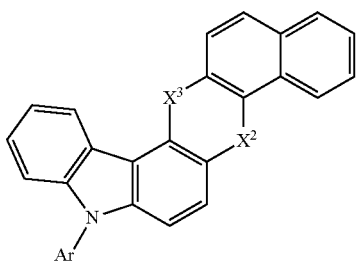
formula (I-5a)
formula (I-6a)
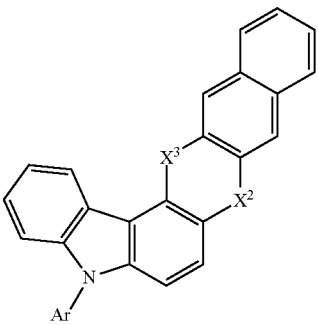
formula (I-7a)
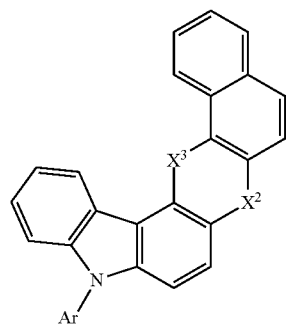
formula (I-17a)
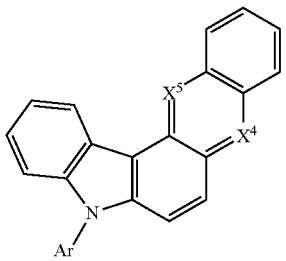
formula (I-18a)
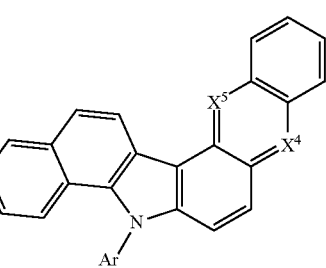
formula (I-19a)
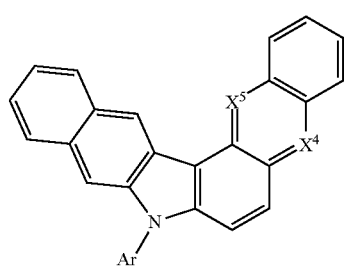

formula (I-20a)

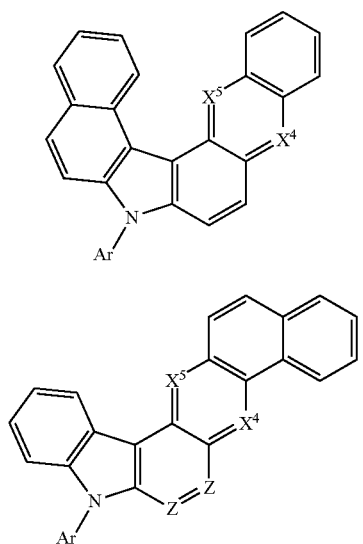

formula (I-21a)

formula (I-22a)

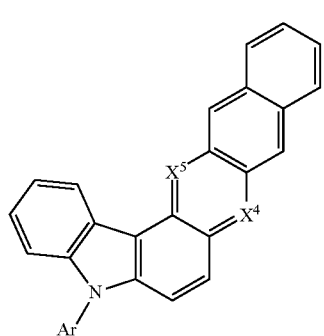

formula (I-23a)

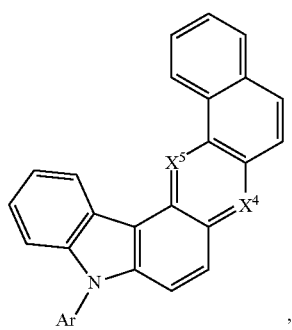

where Ar, $X^2$, $X^3$, $X^4$ and $X^5$ are as defined above, and furthermore the compounds of the formulae shown above may be substituted by one or more radicals $R^1$ or $R^2$.

For the formulae (I-1a) to (I-7a) and (I-17a) to (I-23a), the preferred embodiments of the groups $X^2$, $X^3$, $X^4$ and $X^5$ mentioned above apply in particular.

The preferred embodiments described in the preceding sections can in accordance with the invention be combined with one another as desired.

Examples of compounds according to the invention are shown in the following table.

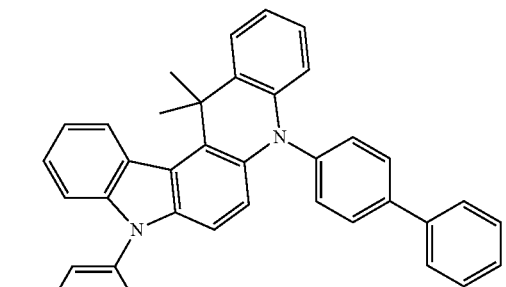

1

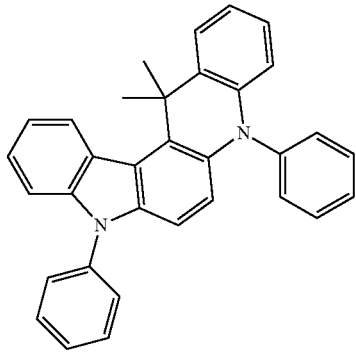 [SMILES: CC1(C)c2ccccc2N(c2ccccc2)c2ccc3c(c21)c1ccccc1n3-c1ccccc1]

2

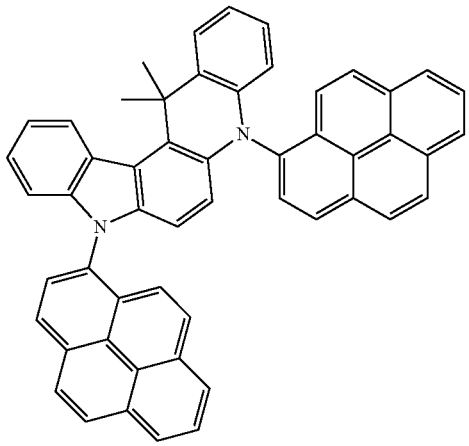 [SMILES: CC1(C)c2ccccc2N(c2ccc3ccc4cccc5ccc2c3c45)c2ccc3c(c21)c1ccccc1n3-c1ccc2ccc3cccc4ccc1c2c34]

3

-continued
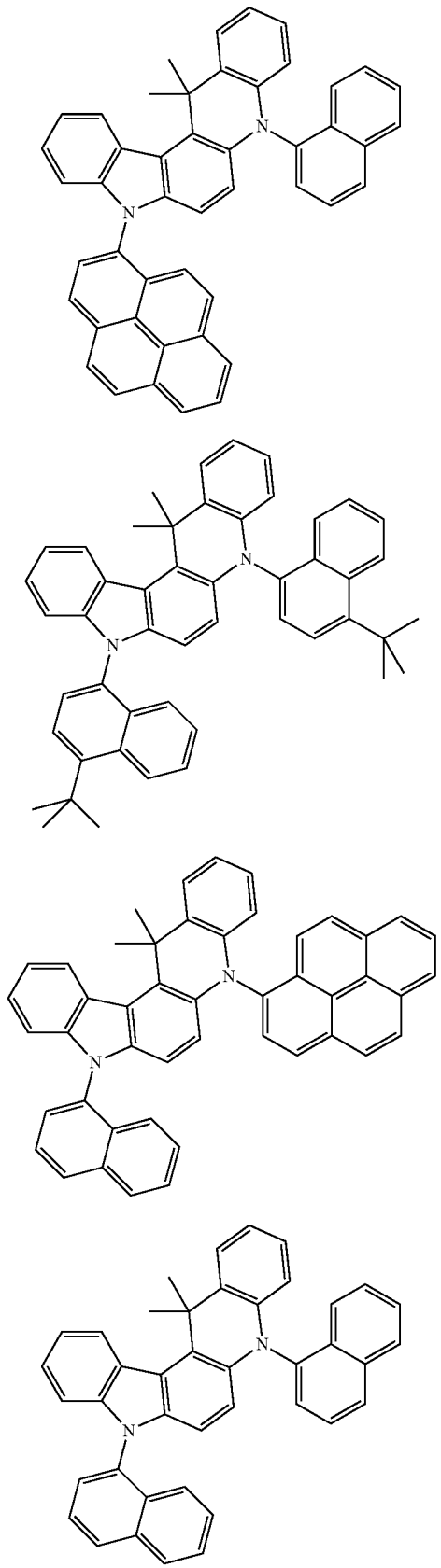
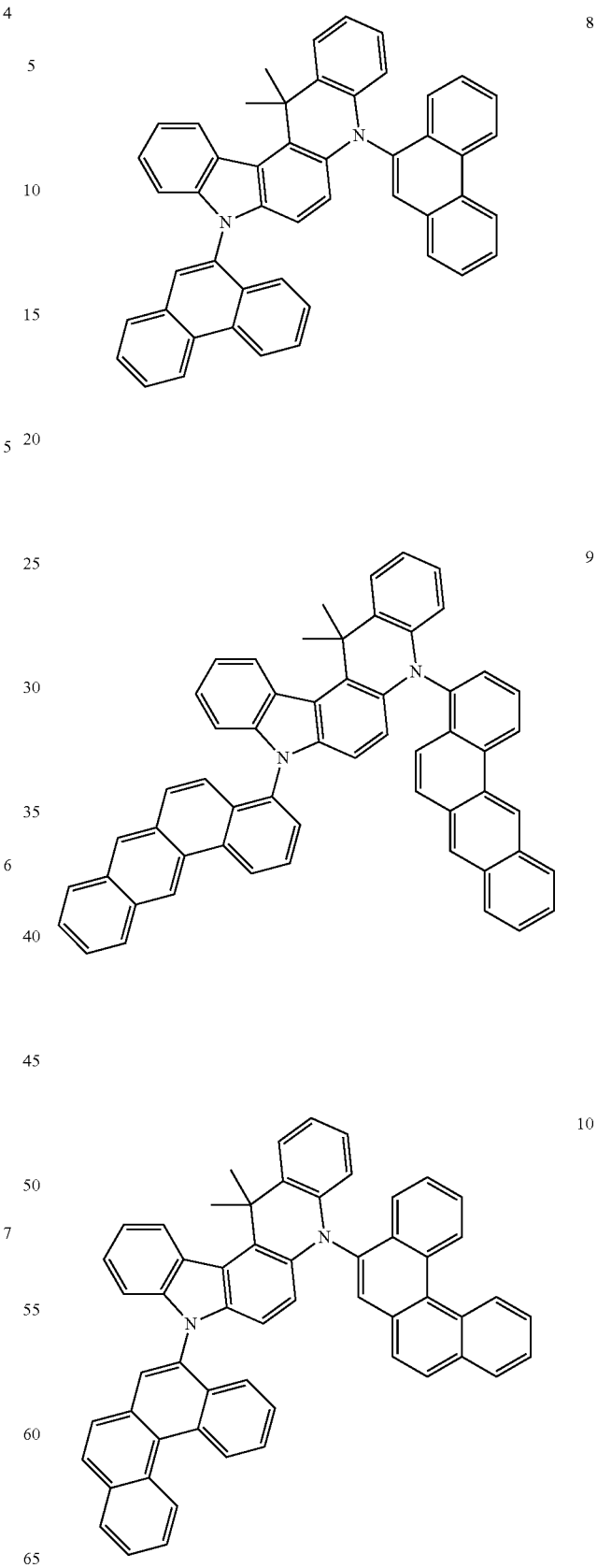

| 29 -continued | 30 -continued |
|---|---|
| 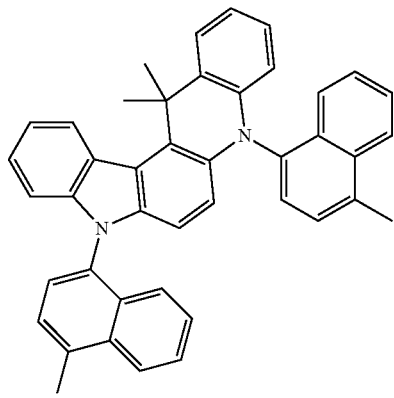 [SMILES: Cc1ccc(N2c3ccccc3C(C)(C)c3c2ccc2c3c3ccccc3n2-c2ccc(C)c3ccccc23)c2ccccc12] 11 | 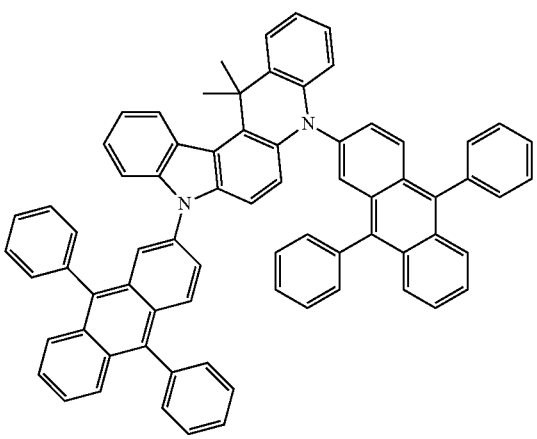 14 |
| 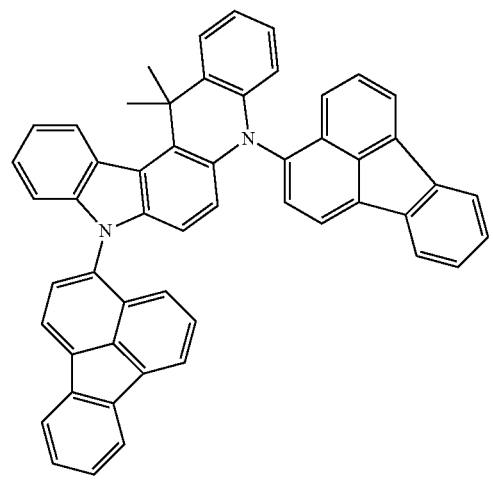 [SMILES: CC1(C)c2ccccc2N(c2ccc3c4c(cccc24)-c2ccccc2-3)c2ccc3c(c21)c1ccccc1n3-c1ccc2c3c(cccc13)-c1ccccc1-2] 12 | 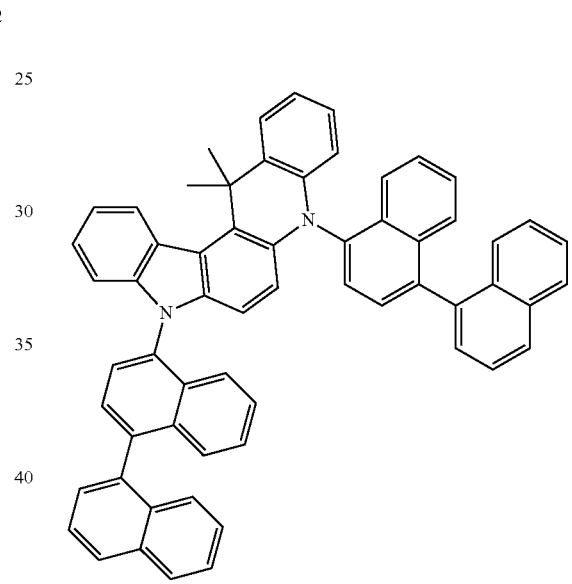 15 |
| 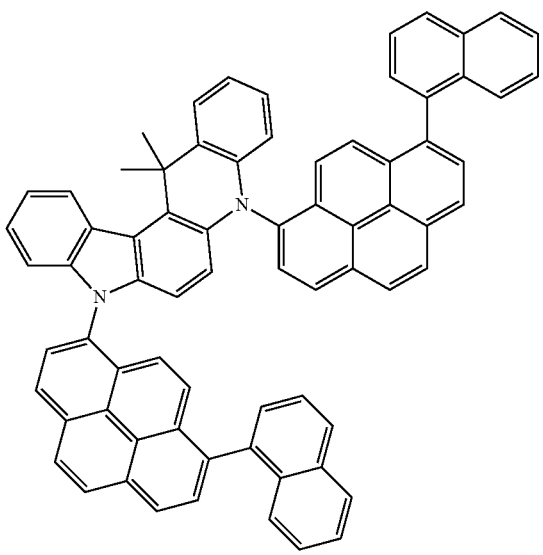 [SMILES: CC1(C)c2ccccc2N(c2ccc3ccc4ccc(-c5cccc6ccccc56)c5ccc2c3c45)c2ccc3c(c21)c1ccccc1n3-c1ccc2ccc3ccc(-c4cccc5ccccc45)c4ccc1c2c34] 13 | 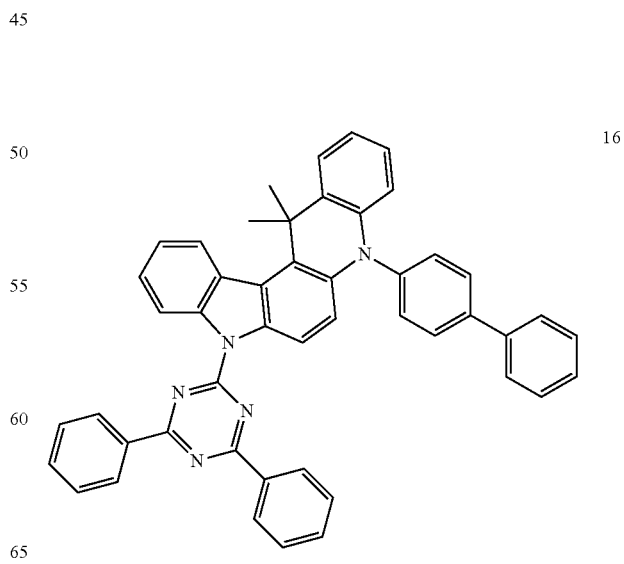 16 |

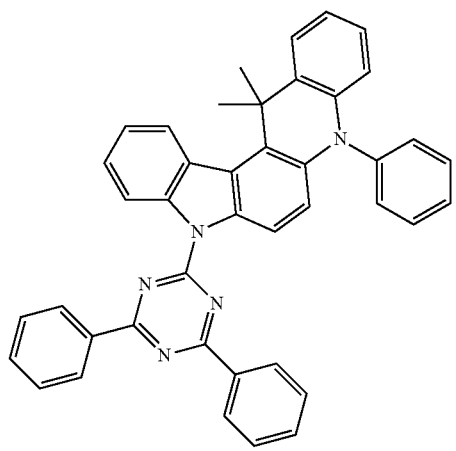 [SMILES: CC1(C)c2ccccc2N(c2ccccc2)c2ccc3c(c21)c1ccccc1n3-c1nc(-c2ccccc2)nc(-c2ccccc2)n1]
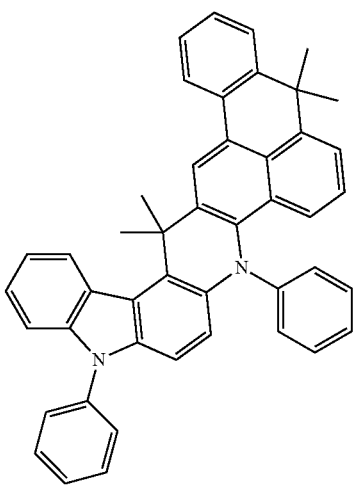 [SMILES: CC1(C)c2ccccc2-c2cc3c(c4cccc1c24)N(c1ccccc1)c1ccc2c(c1C3(C)C)c1ccccc1n2-c1ccccc1]

-continued
23
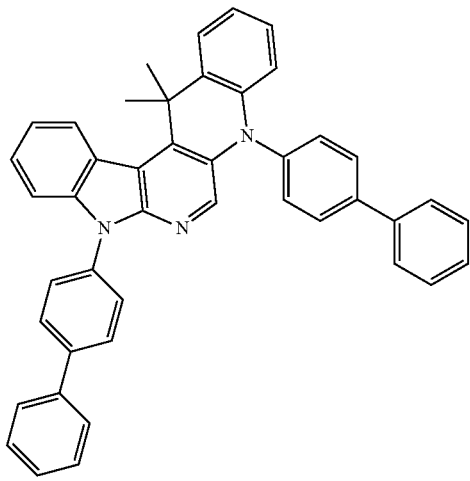 [SMILES: CC1(C)c2ccccc2N(c2ccc(-c3ccccc3)cc2)c2cnc3c(c21)c1ccccc1n3-c1ccc(-c2ccccc2)cc1]
24
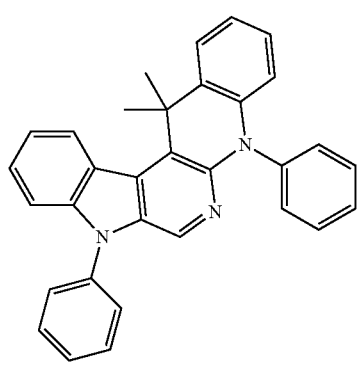 [SMILES: CC1(C)c2ccccc2N(c2ccccc2)c2ncc3c(c21)c1ccccc1n3-c1ccccc1]
25
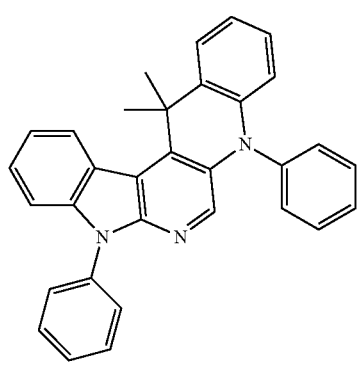
-continued
26
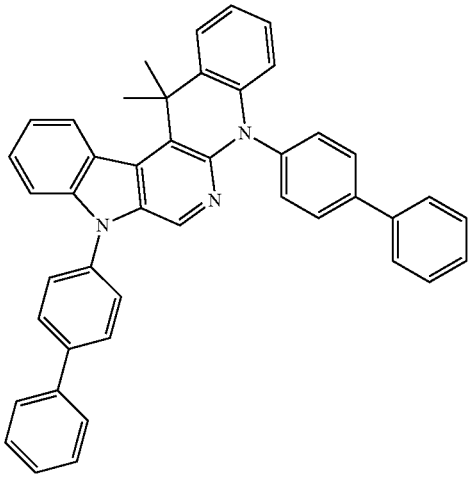 [SMILES: CC1(C)c2ccccc2N(c2ccc(-c3ccccc3)cc2)c2ncc3c(c21)c1ccccc1n3-c1ccc(-c2ccccc2)cc1]
27
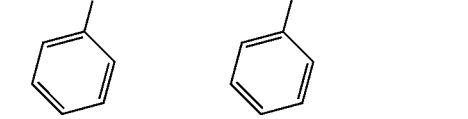
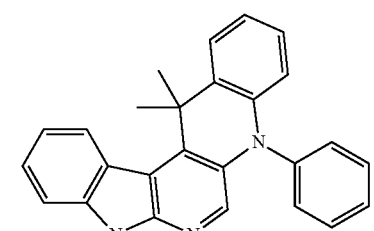
28
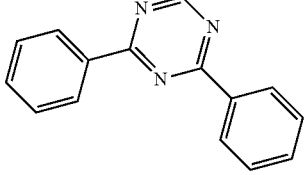
29
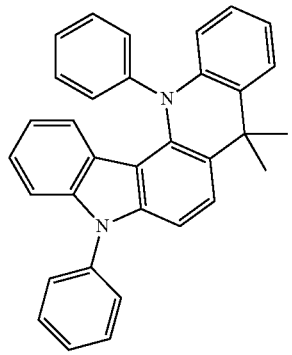 [SMILES: CC1(C)c2ccccc2N(c2ccccc2)c2c1ccc1c2c2ccccc2n1-c1ccccc1]

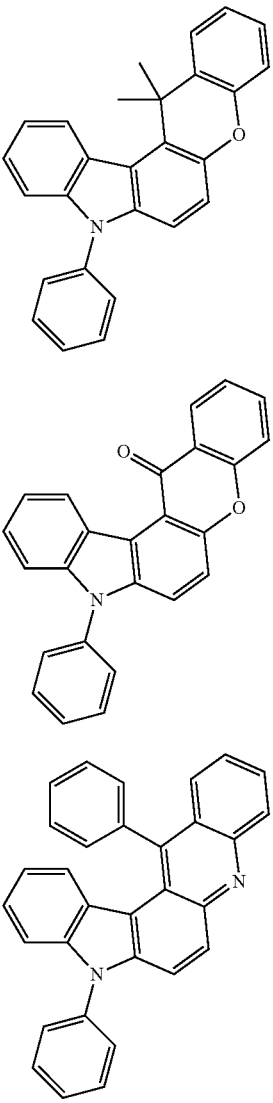

30

31

32

The compounds according to the invention can be prepared by synthetic steps known to the person skilled in the art, such as, for example, bromination, Suzuki coupling, Hartwig-Buchwald coupling, etc.

Possible synthetic routes to compounds of the formula (I) having a substituted nitrogen atom as group $X^1$ are shown in general terms in Schemes 1 to 4 below.

Compounds of the formula (I) in which $X^1$ represents another group, for example O, S or $C(R^1)_2$, can also be obtained analogously. In these cases, the synthesis starts from a dibenzothiophene, dibenzofuran or fluorene derivative instead of the corresponding carbazole derivative.

Compounds in which nitrogen-analogous heterocycles, preferably including pyridine, pyrimidine, pyridazine, pyrazine and triazine, occur instead of the aromatic rings shown can also be prepared analogously.

Scheme 1 below shows, inter alia, the synthesis of compounds of the formula (Ia) where $X^2$ is a group N—H or N—Ar and $X^3$ is a group C=O (compounds of type a). To this end, the synthesis starts from a halogen-substituted carbazole derivative, which is reacted with an anthranilic acid derivative in an Ullmann coupling. The resultant derivative is reacted with $POCl_3$ at about 60° C., where a ring-closure reaction occurs and the six-membered ring containing the bridging group C=O as $X^3$ is formed. The resultant compound can be N-arylated, for example, in a Hartwig-Buchwald reaction. In a variant of the reaction with $POCl_3$, in which a temperature of about 120° C. is employed, a compound type b, which conforms to the formula (Ib) according to the invention, where $X^4$ is a nitrogen atom and $X^5$ is a group C—Cl, is formed instead of a derivative of type a. The unfunctionalised compound where $X^5$ is CH can be prepared from these compounds by a defunctionalisation reaction, or an aryl group can be introduced instead of the chlorine atom via a coupling reaction, for example a Suzuki coupling (cf. Scheme 1).

Scheme 1

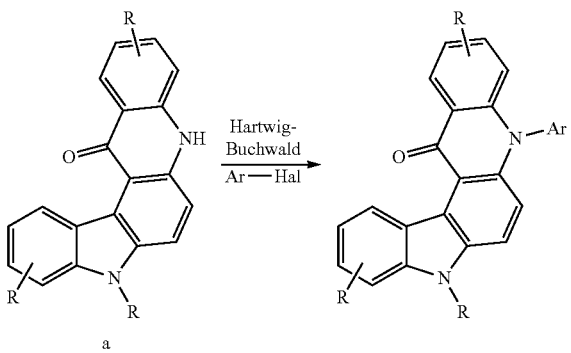

a

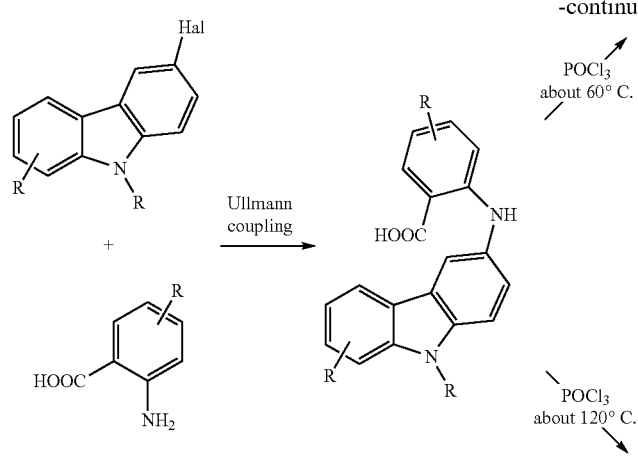
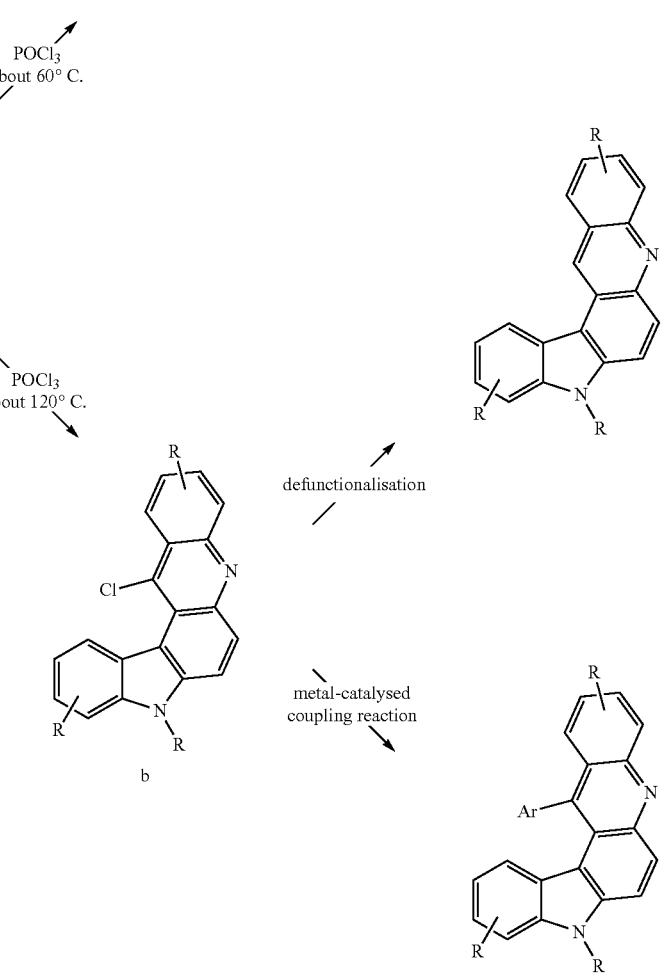

R = any desired radical
Ar = aromatic or heteroaromatic ring system
Hal = halogen Compounds of type c where $X^2$ is N—H or N—Ar and $X^3$ is $C(R)_2$ can furthermore be obtained starting from the intermediate formed in the Ullmann coupling shown in Scheme 1, by reaction with an alkyllithium compound followed by treatment with acid, for example methanesulfonic acid or polyphosphoric acid (Scheme 2).

Scheme 2

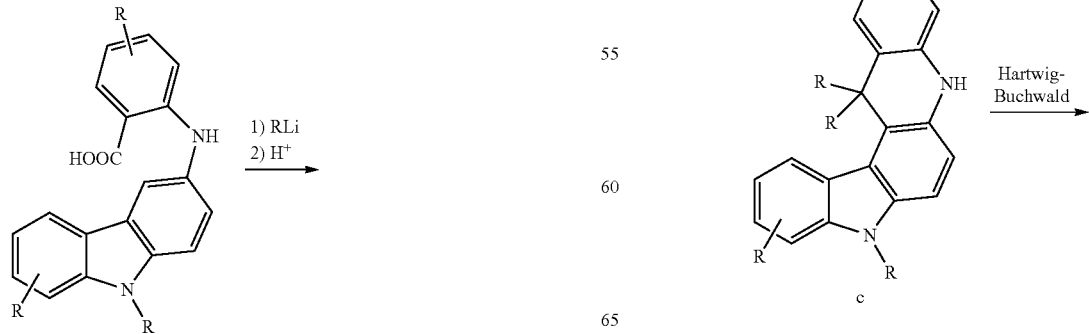

-continued

-continued

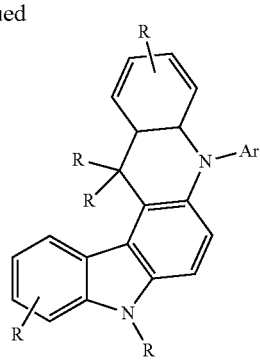

R = any desired radical
Ar = aromatic or heteroaromatic ring system

Diaryl ether or diaryl thioether intermediates can again furthermore be obtained, as shown in Scheme 3, starting from hydroxyl- or thiol-substituted carbazole derivatives by reaction with a halogen-substituted benzoic acid derivative.

Scheme 3

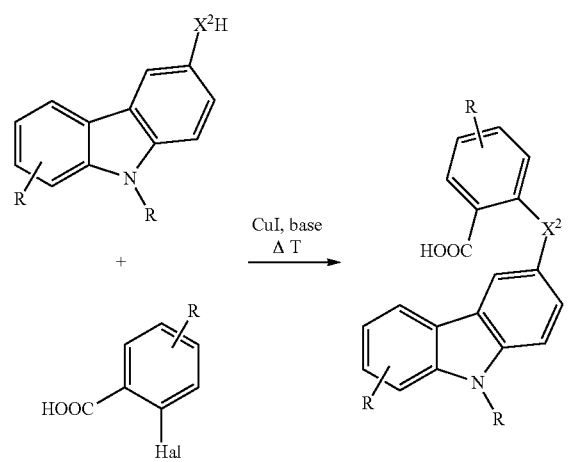

$X^2$ = O, S
Hal = halogen
R = any desired radical

These intermediates can be reacted, analogously to that shown in Scheme 1, with $POCl_3$ to give compounds of type d ($X^2$=O) or of type e ($X^2$=S) (Scheme 4). Alternatively, the intermediates can be reacted, analogously to that shown in Scheme 2, by the addition reaction of organolithium compounds followed by acid treatment to give compounds of type f ($X^2$=O) or of type g ($X^2$=S) (Scheme 4).

Scheme 4

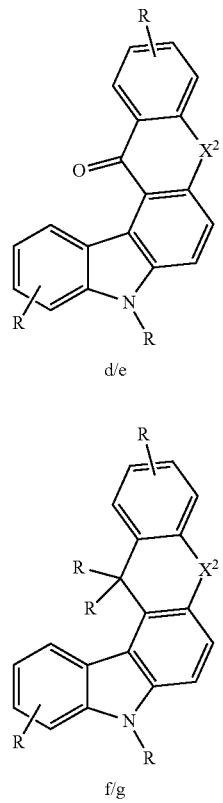

$X^2$ = O, S
R = any desired radical

The invention thus relates to a process for the preparation of the compounds of the formula (I) according to the invention, characterised in that an intermediate of the following formula (Za) or (Zb) is employed

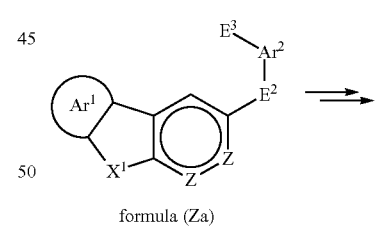

formula (Za)

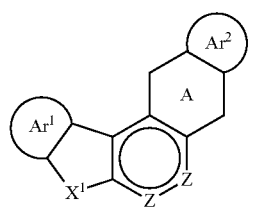

formula (I)

where 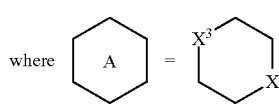

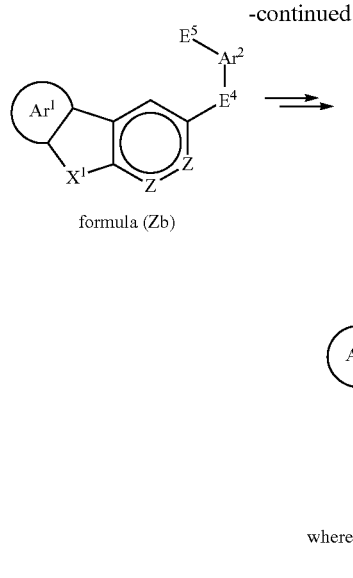

formula (Zb)

formula (I)

where the symbols occurring are as defined above, and $E^2$ represents a precursor of the divalent group $X^2$, $E^3$ represents a precursor of the divalent group $X^3$, $E^4$ represents a precursor of the group $X^4$, and $E^5$ represents a precursor of the group $X^5$.

The compounds according to the invention described above, in particular compounds which are substituted by reactive leaving groups, such as bromine, iodine, boronic acid or boronic acid ester, can be used as monomers for the preparation of corresponding oligomers, dendrimers or polymers. The oligomerisation or polymerisation here is preferably carried out via the halogen functionality or the boronic acid functionality.

The invention therefore furthermore relates to oligomers, polymers or dendrimers comprising one or more compounds of the formula (I), where the bond(s) to the polymer, oligomer or dendrimer may be localised at any desired positions in formula (I) substituted by $R^1$ or $R^2$. Depending on the linking of the compound of the formula (I), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (I) may, for example, be linked via a trivalent or polyvalent group, for example via a trivalent or polyvalent aromatic or heteroaromatic group, to give a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689 or WO 07/006383), cis- and trans-indenofluorenes (for example in accordance with WO 04/041901 or WO 04/113412), ketones (for example in accordance with WO 05/040302), phenanthrenes (for example in accordance with WO 05/104264 or WO 07/017066) or also a plurality of these units. The polymers, oligomers and dendrimers usually also contain further units, for example emitting (fluorescent or phosphorescent) units, such as, for example, vinyltriarylamines (for example in accordance with WO 07/068325) or phosphorescent metal complexes (for example in accordance with WO 06/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (I) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 02/067343 A1 and WO 2005/026144 A1.

The compounds of the formula (I) according to the invention are suitable for use in electronic devices, in particular in organic electroluminescent devices (OLEDs). Depending on the substitution, the compounds are employed in various functions and layers. For example, compounds which contain electron-deficient groups, such as six-membered ring heteroaryl groups having one, preferably a plurality of nitrogen atoms or five-membered ring heteroaryl groups having two or more nitrogen atoms, are particularly suitable for use as matrix material for phosphorescent dopants or as electron-transport material.

The compounds according to the invention are preferably employed as matrix material in a hole-transport and/or hole-injection layer or in an emitting layer. However, they can also be employed in other layers and/or functions, for example as fluorescent dopants in an emitting layer or as electron-transport materials in an electron-transport layer.

The invention therefore furthermore relates to the use of the compounds of the formula (I) according to the invention in electronic devices. The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably organic electroluminescent devices (OLEDs).

The invention also relates to formulations comprising at least one compound of the formula (I) or at least one polymer, oligomer or dendrimer containing at least one unit of the formula (I), and at least one solvent, preferably an organic solvent.

The formulations according to the invention are used, for example, in the production of organic electroluminescent devices, which is described in greater detail in a following section.

The invention again furthermore relates to electronic devices comprising at least one compound of the formula (I). The electronic devices here are preferably selected from the devices mentioned above. Particular preference is given to organic electroluminescent devices comprising an anode, a cathode and at least one emitting layer, characterised in that at least one organic layer, which may be an emitting layer, a hole-transport layer or another layer, comprises at least one compound of the formula (I).

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*), coupling-out layers and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device may also comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue and yellow, orange or red light are used in the emitting layers. Particular preference is given to three-layer systems, i.e. systems having three emitting layers, where at least one of these layers comprises at least one compound of the formula (I) and where the three layers exhibit blue, green and orange or red emission (for the basic structure see, for example, WO 05/011013).

Alternatively and/or additionally, the compounds according to the invention may also be present in the hole-transport layer. Emitters which have broadband emission bands and thus exhibit white emission are likewise suitable for white emission.

It is preferred in accordance with the invention for the compound of the formula (I) to be employed in an electronic device comprising one or more phosphorescent dopants. The compound here can be used in various layers, preferably in a hole-transport layer, a hole-injection layer or in the emitting layer. However, the compound of the formula (I) can also be employed in accordance with the invention in an electronic device comprising one or more fluorescent dopants.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to employ further phosphorescent complexes without inventive step in combination with the compounds of the formula (I) according to the invention in organic electroluminescent devices.

Examples of suitable phosphorescent emitter compounds are furthermore revealed by the following table:

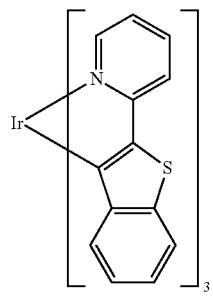

-continued
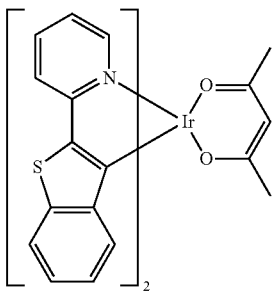
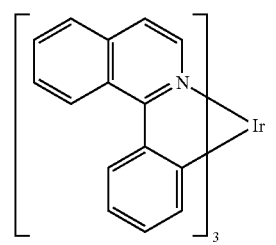
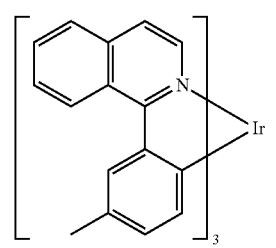
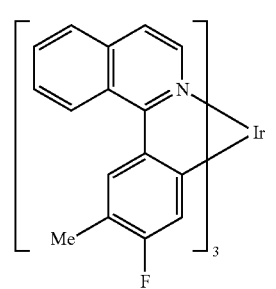
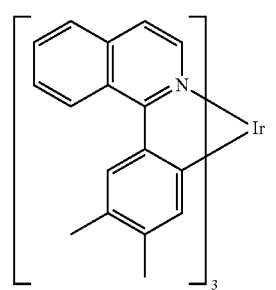
-continued
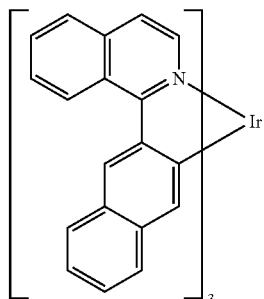
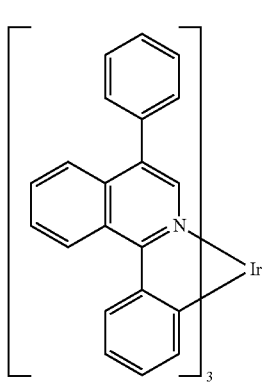
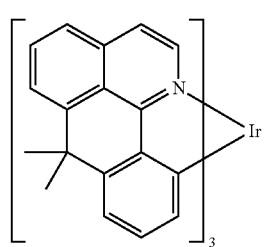
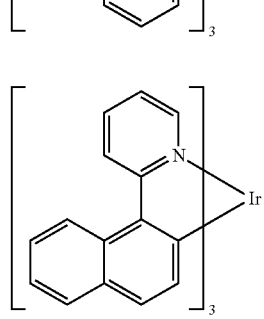
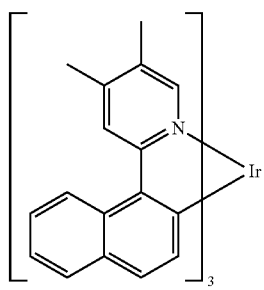

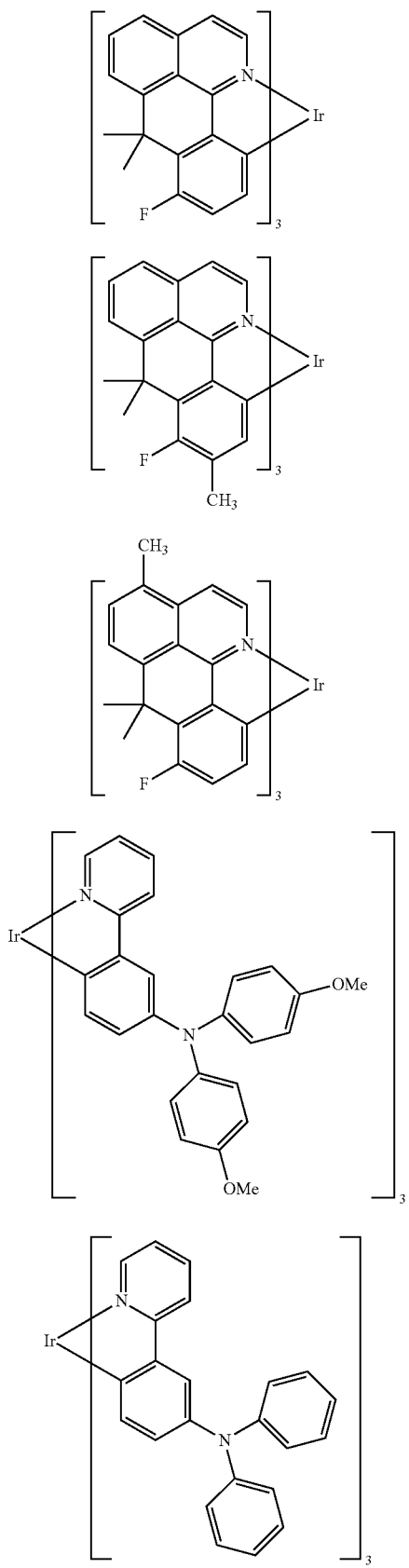
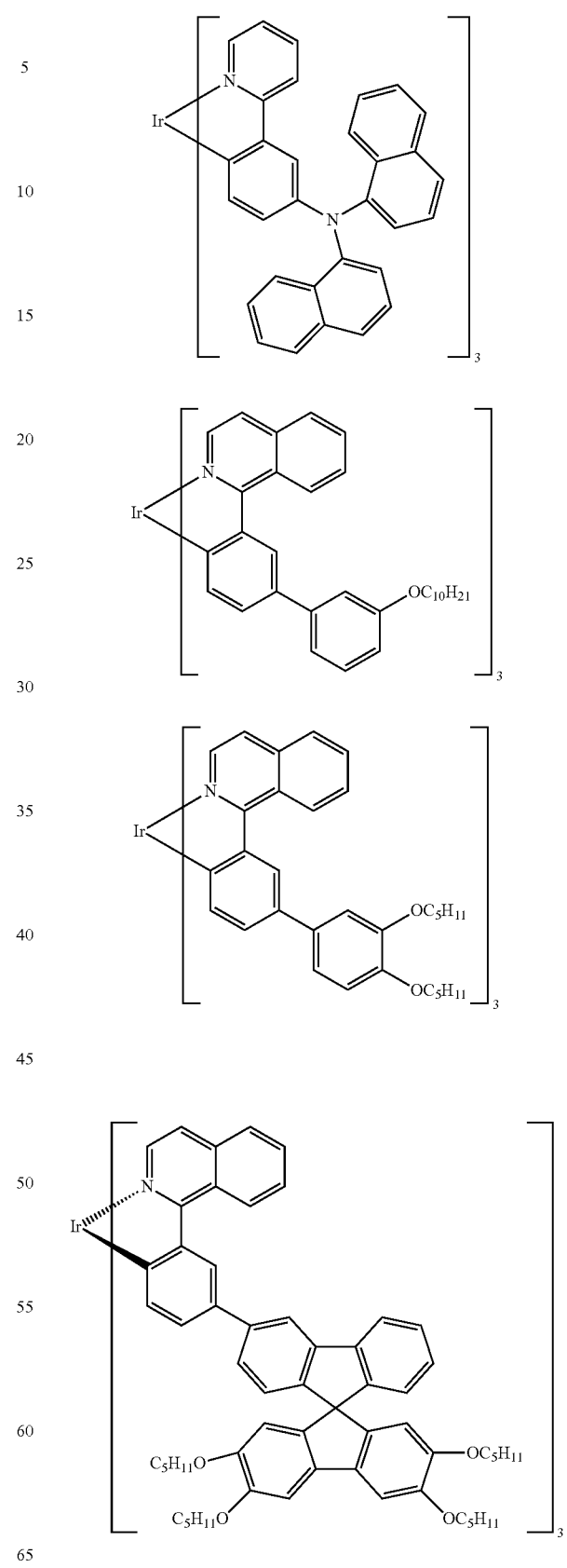

-continued
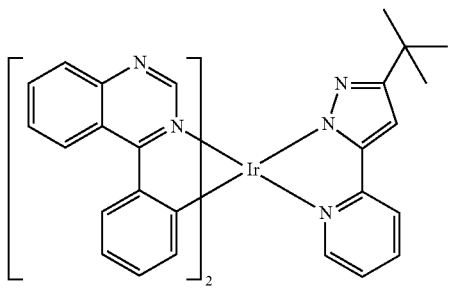
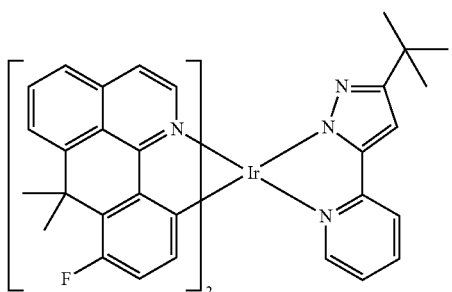
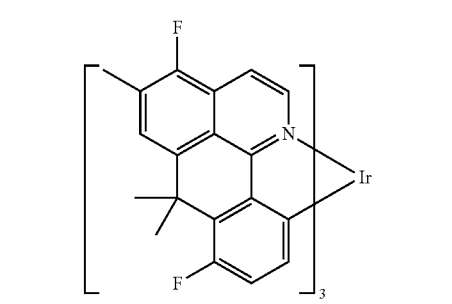
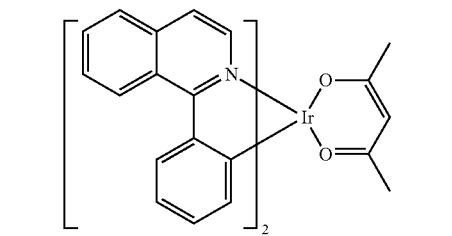
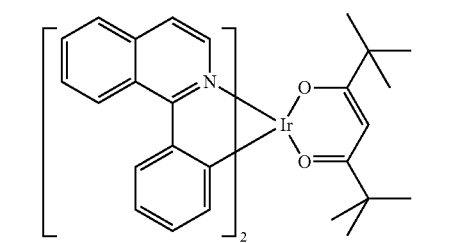
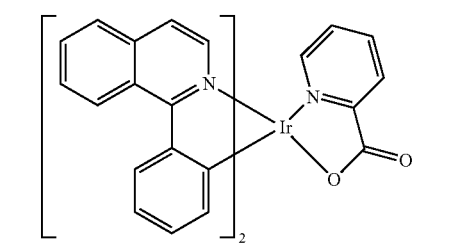
-continued
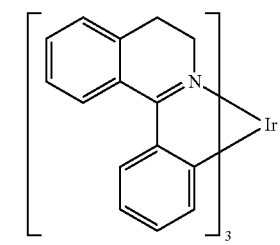
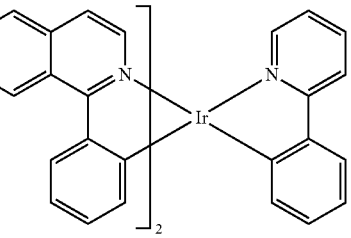
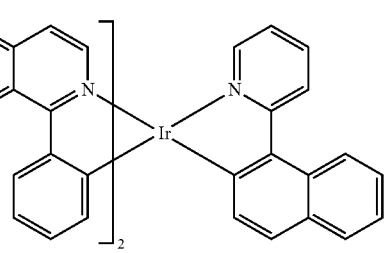
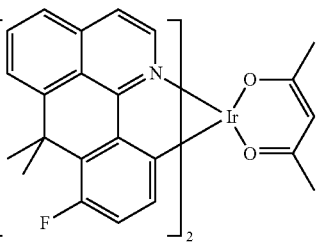
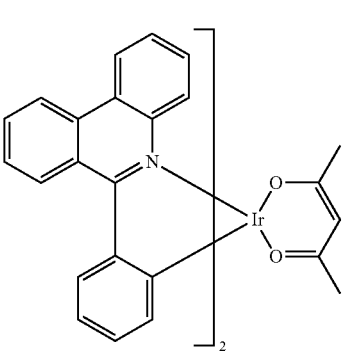
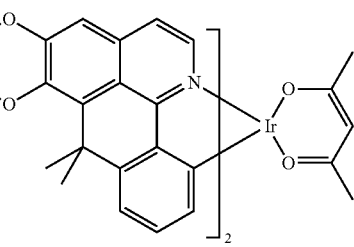

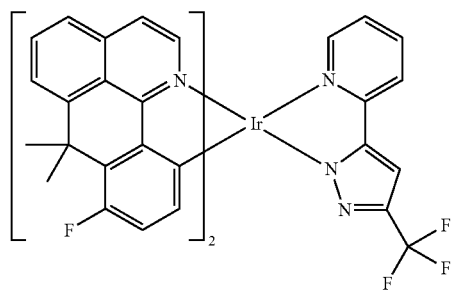
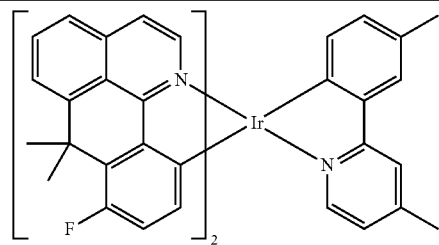
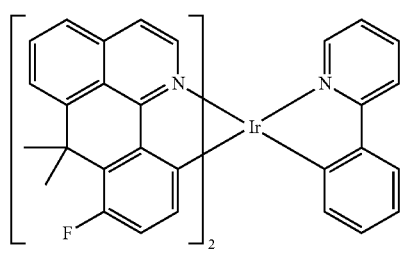
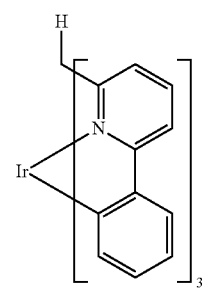
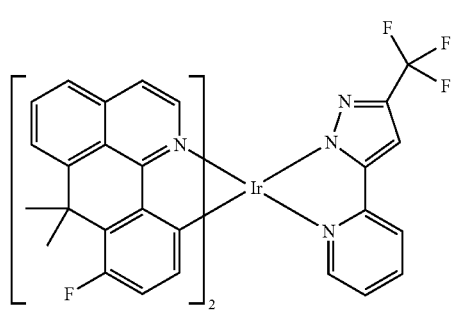
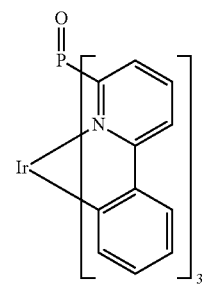
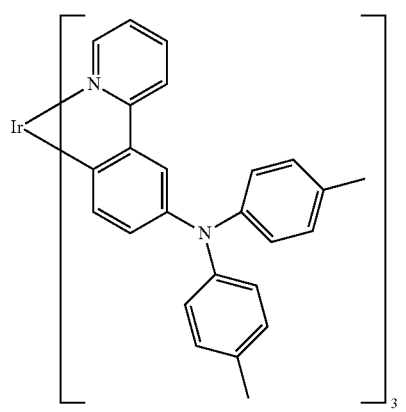
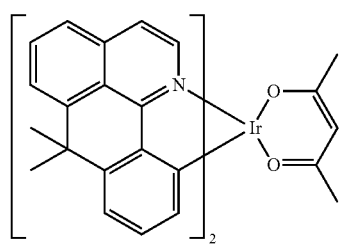
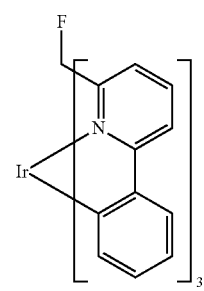
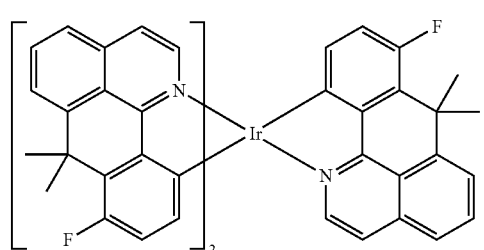
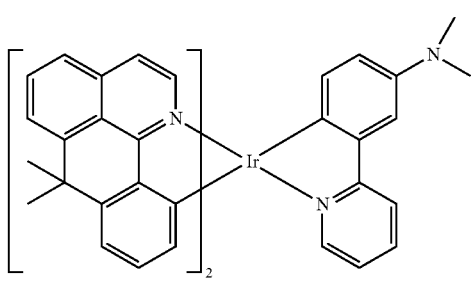

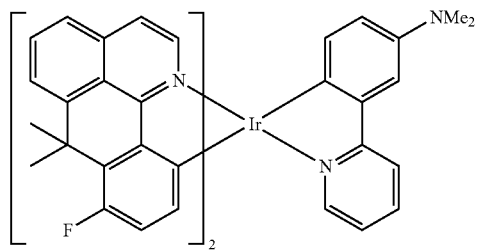
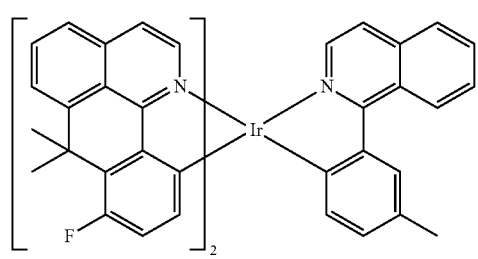
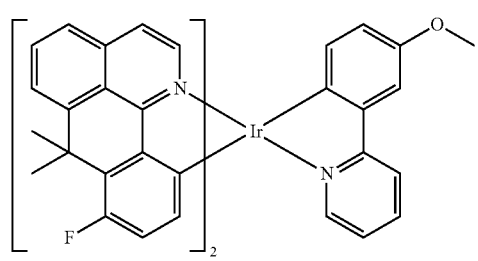
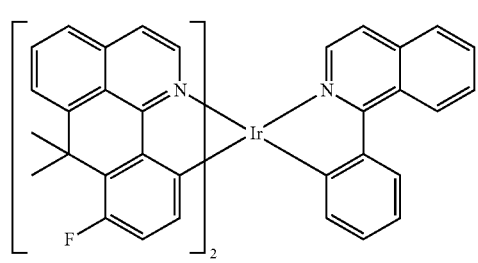
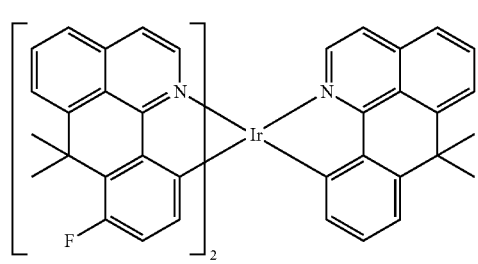
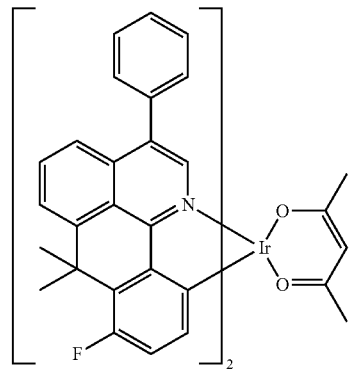
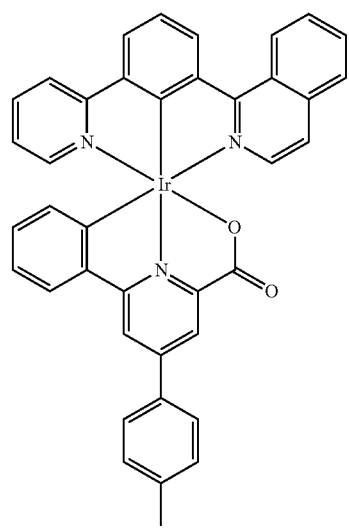
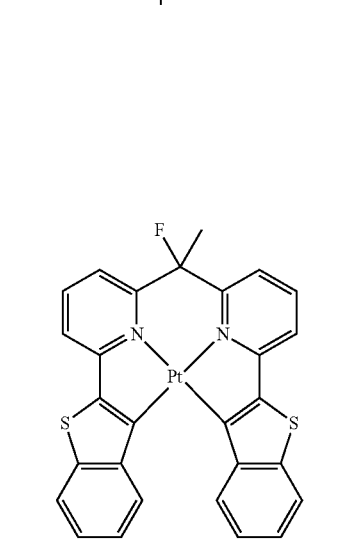

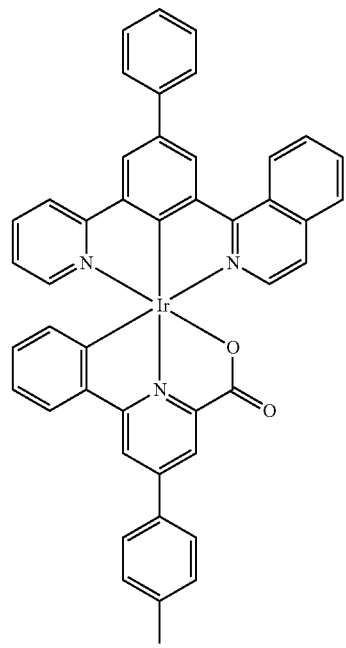
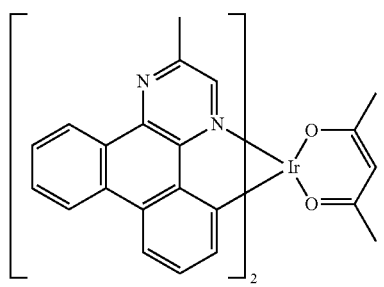
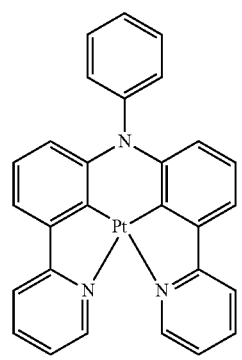
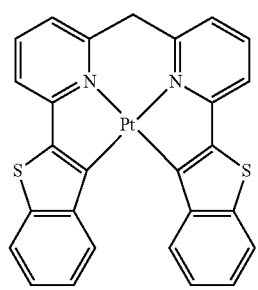
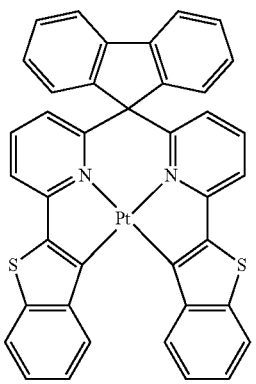
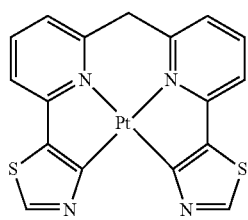
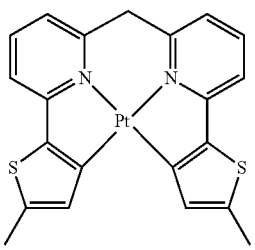
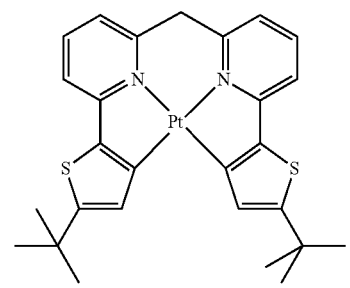
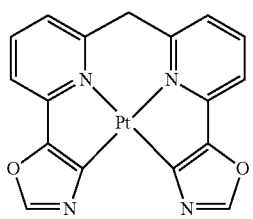

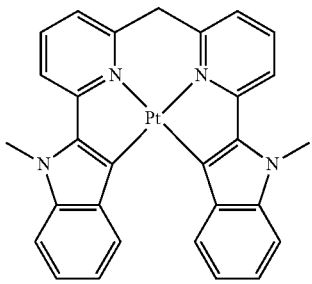
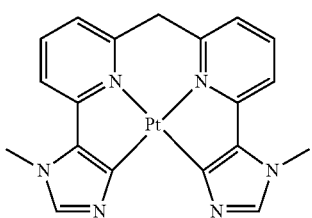
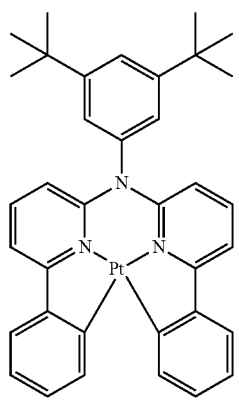
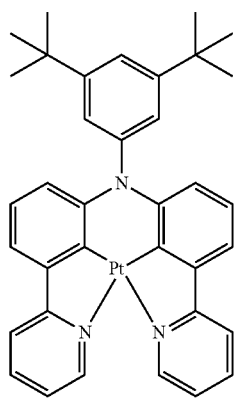
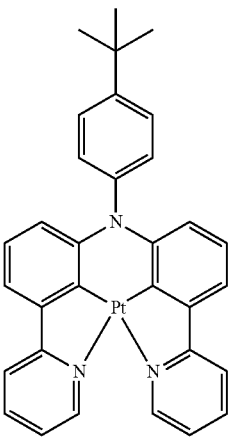
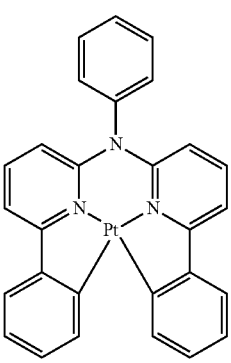
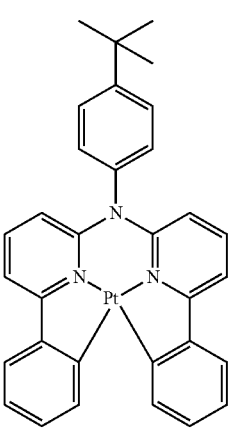
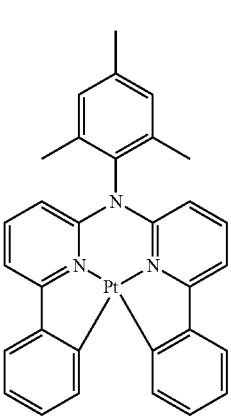

-continued
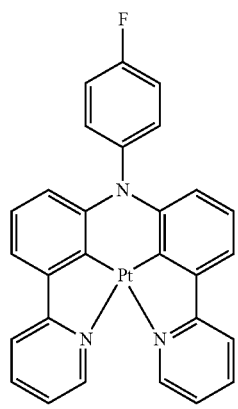
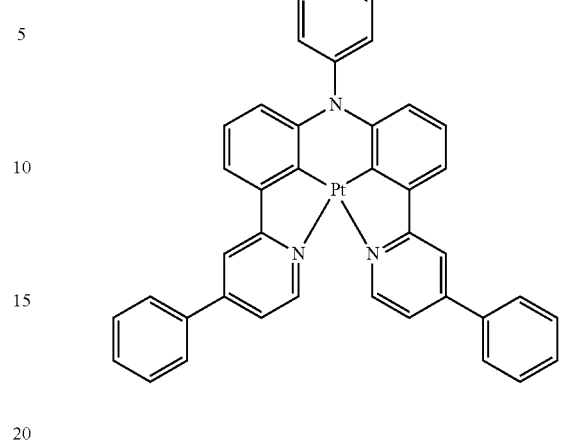
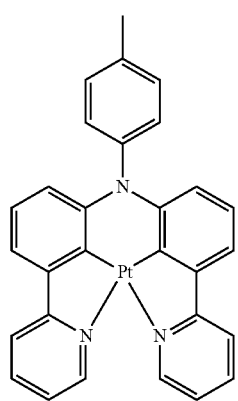
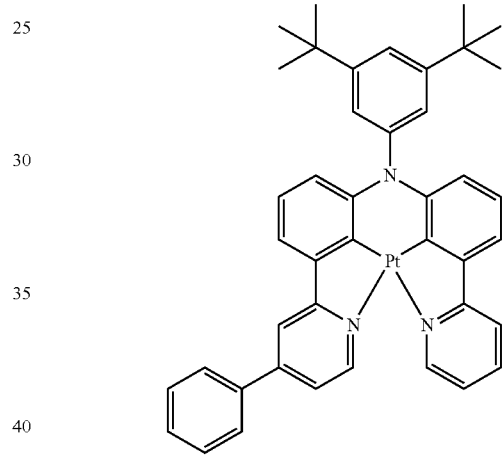
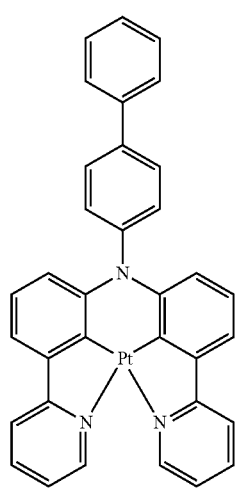
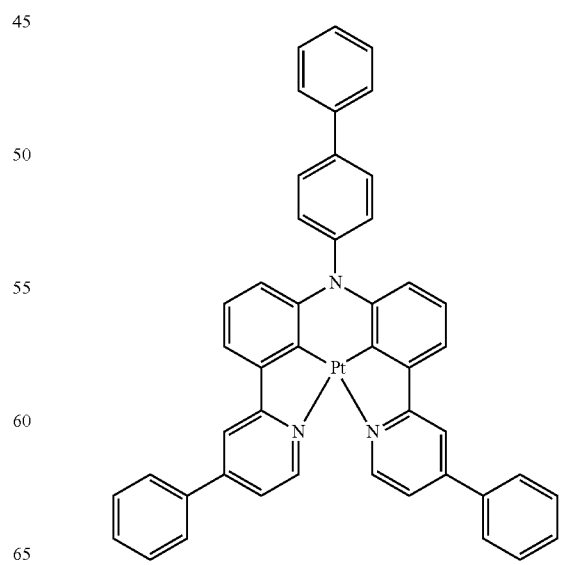

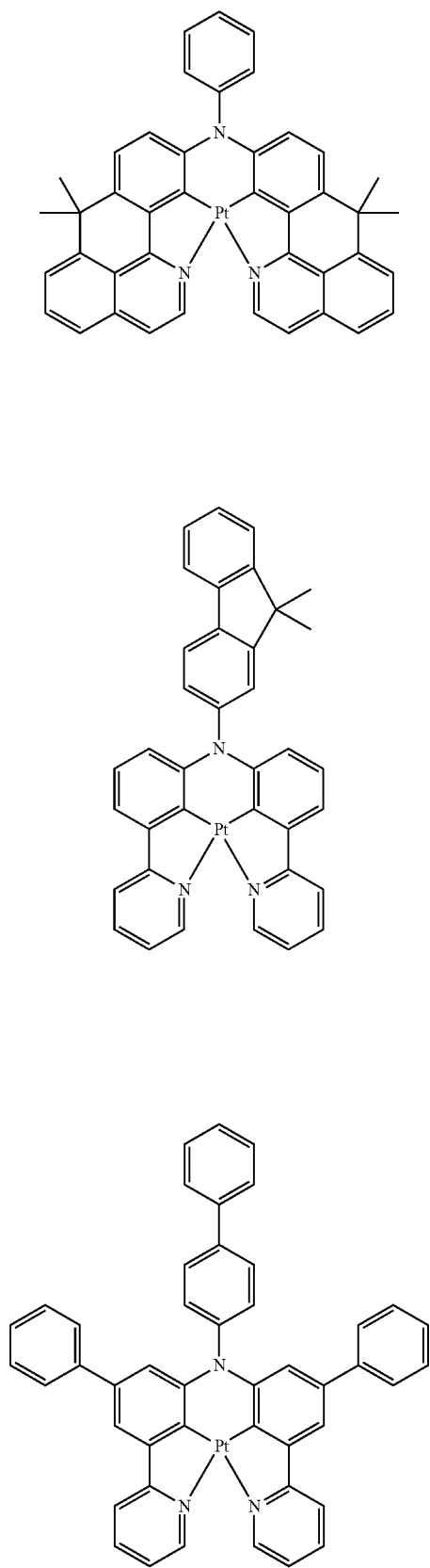
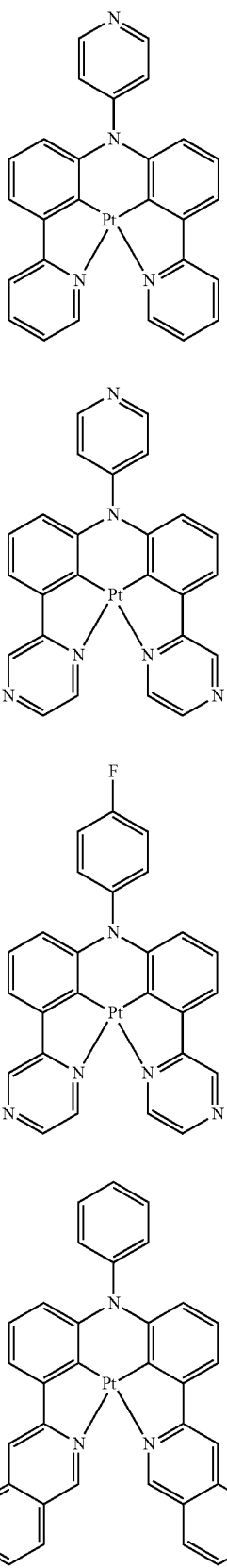

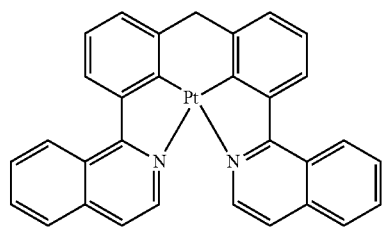
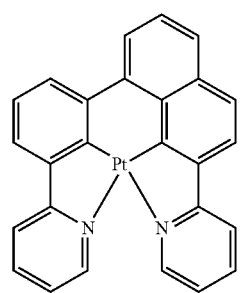
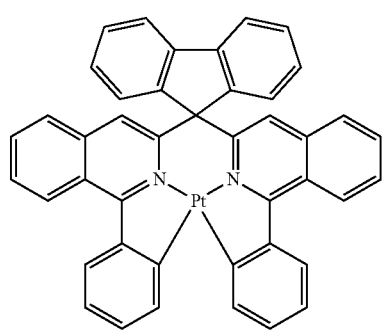
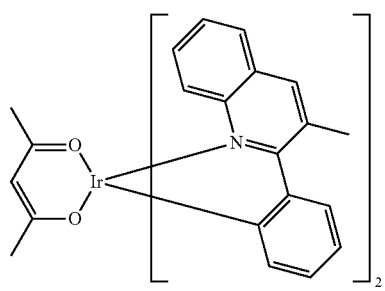
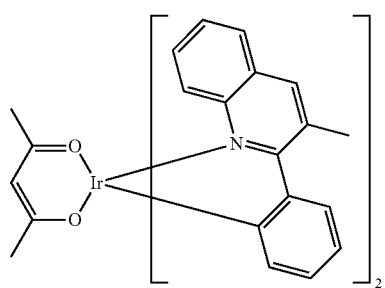
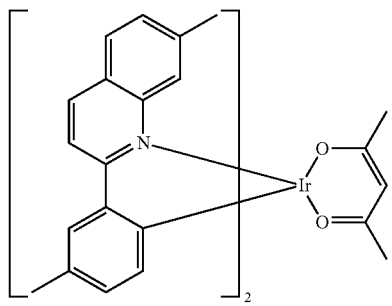
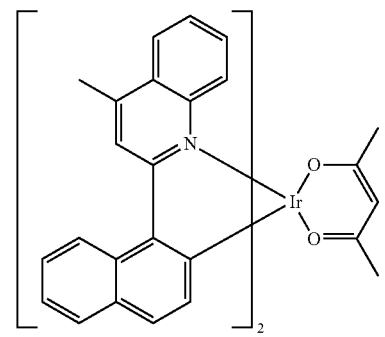
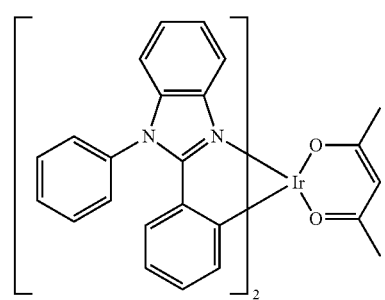
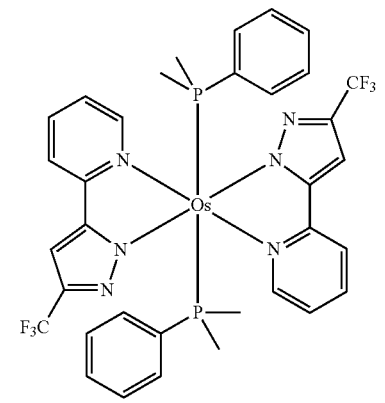
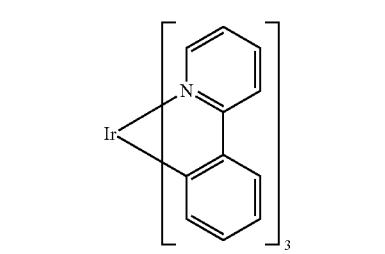

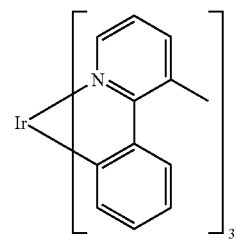
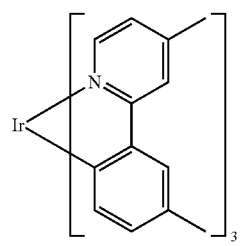
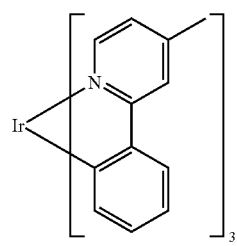
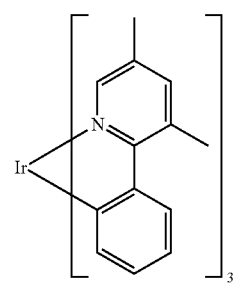
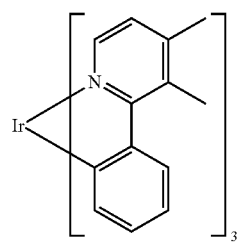
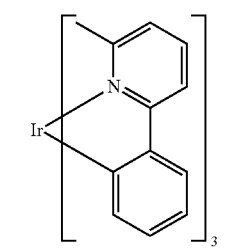
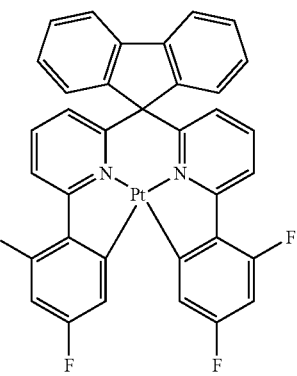
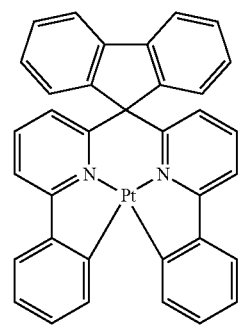
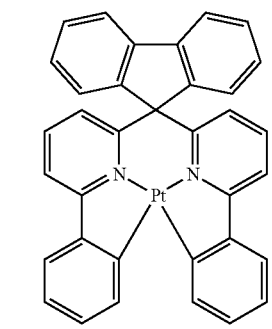
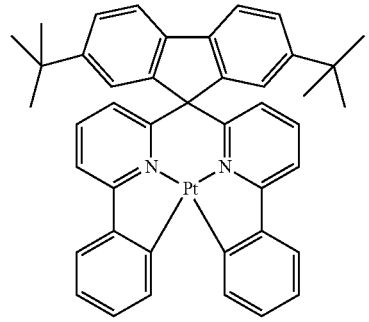
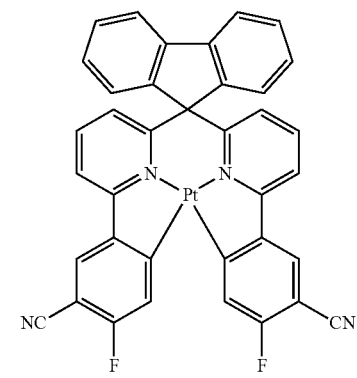

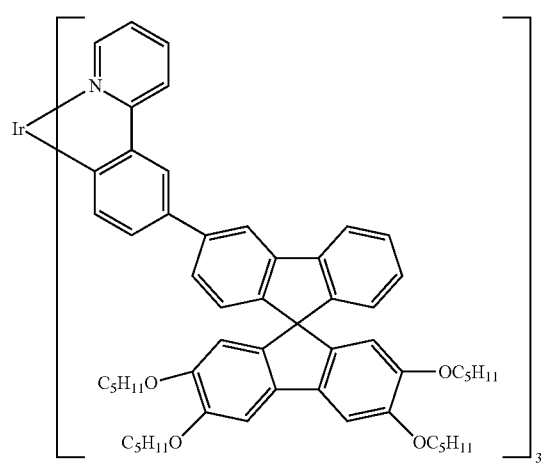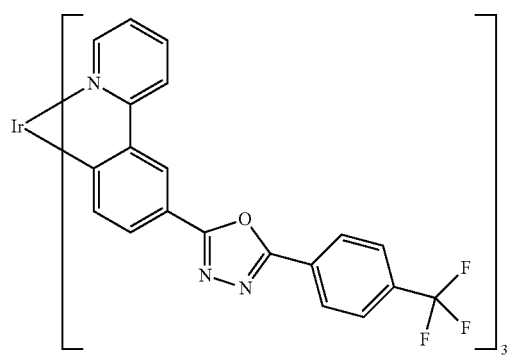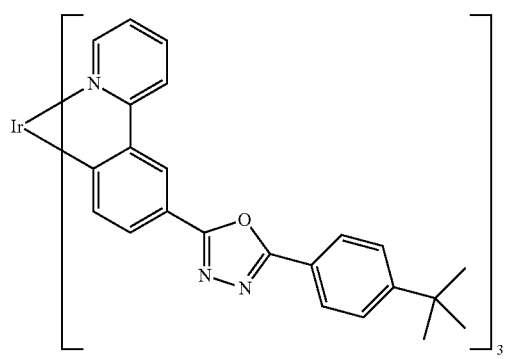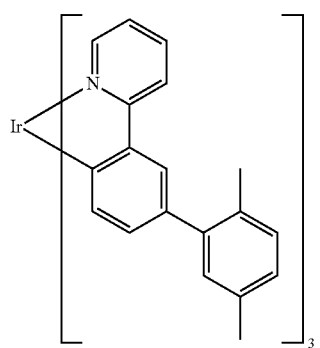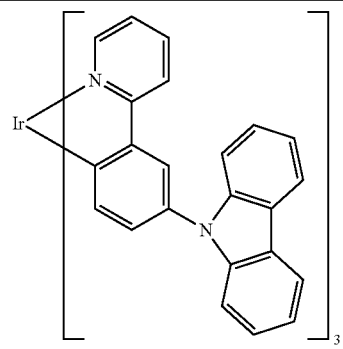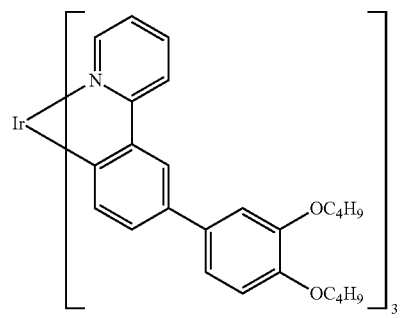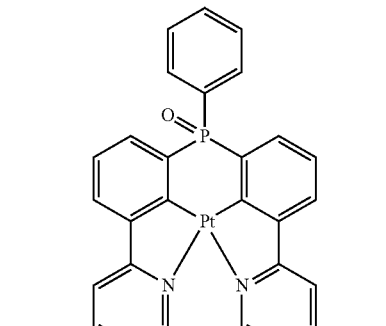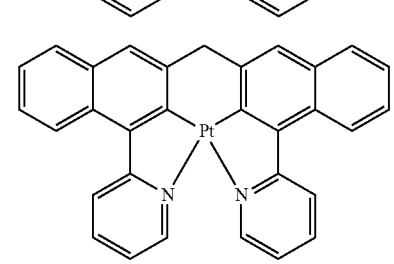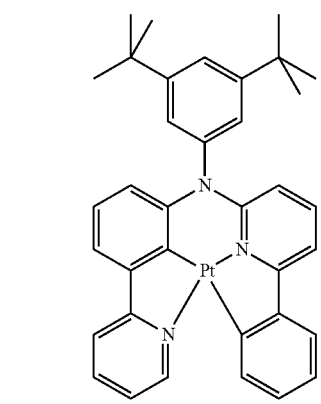

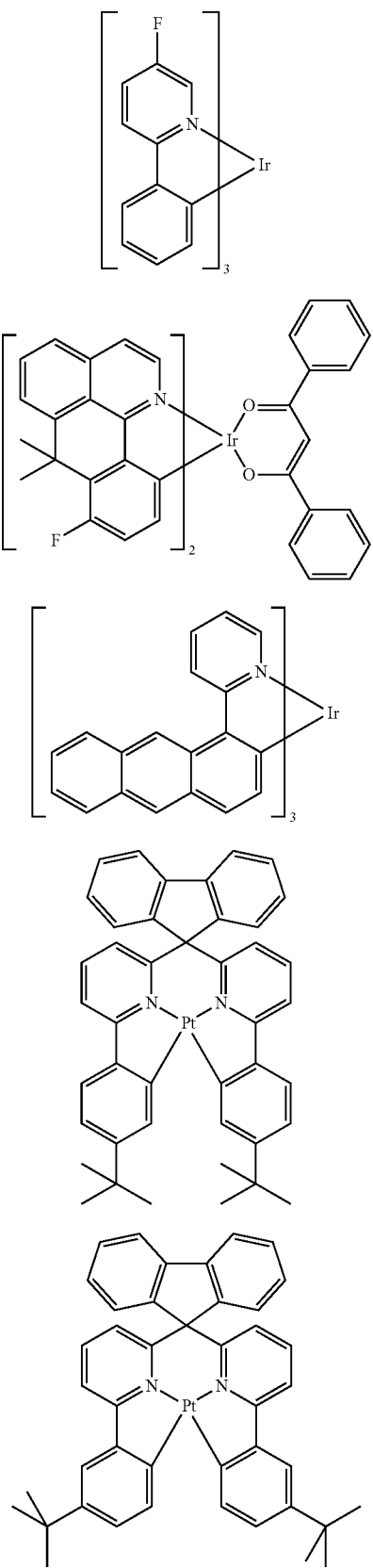
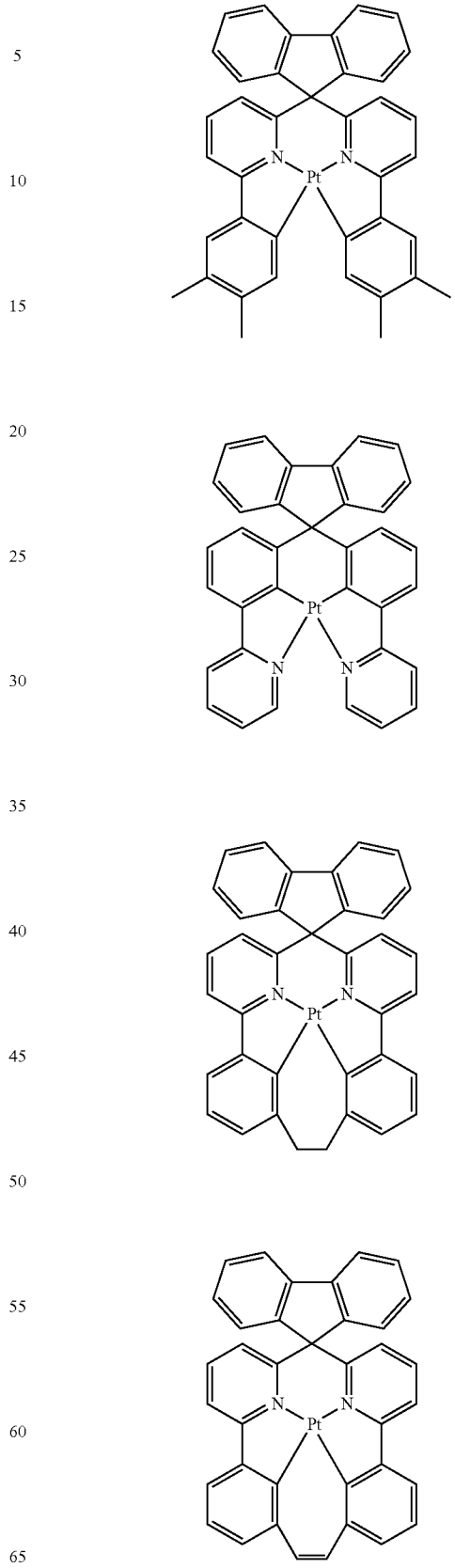

71
-continued
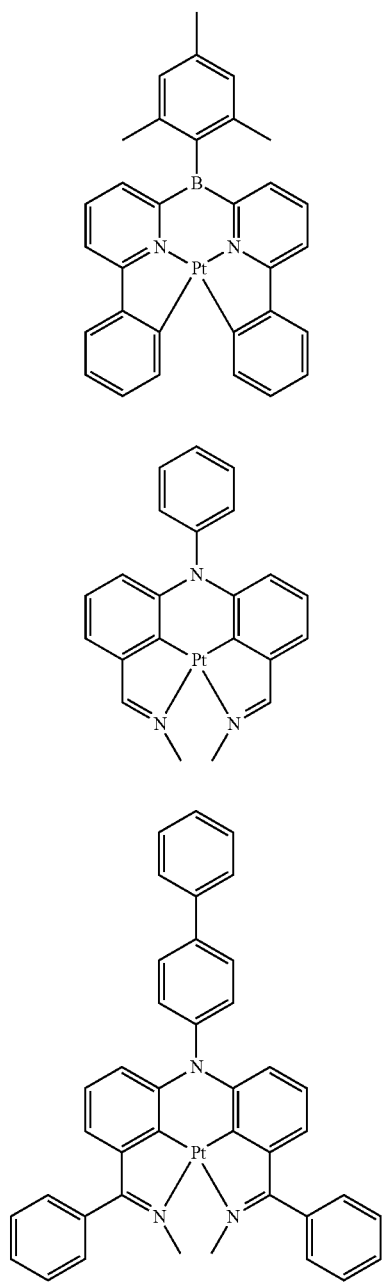
72
-continued
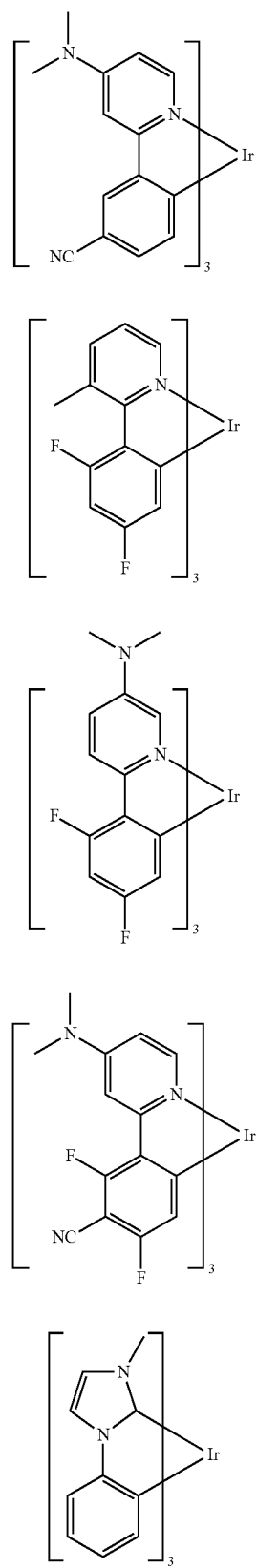

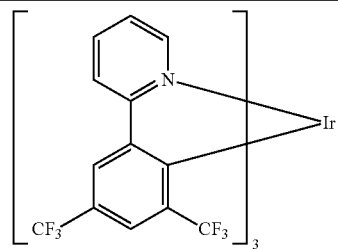
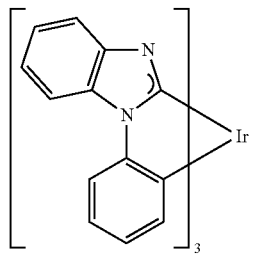
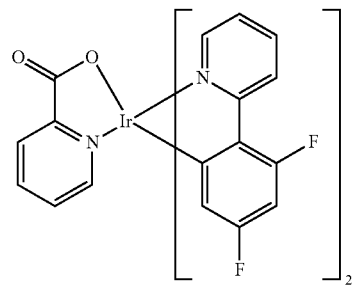
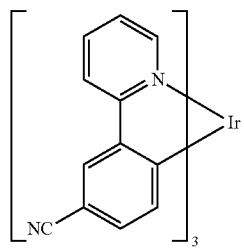
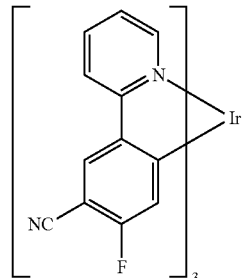
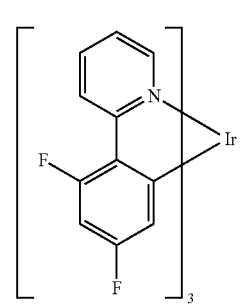
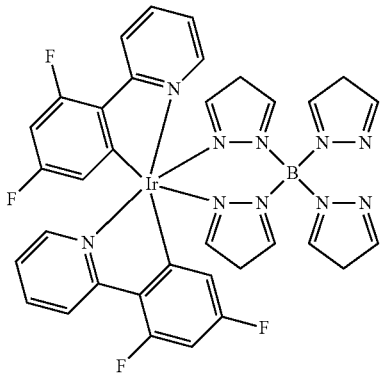
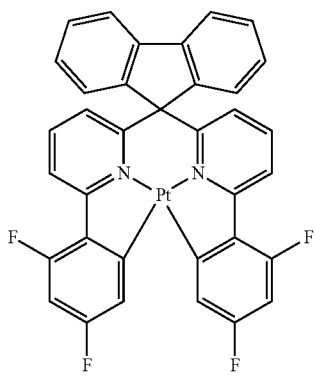
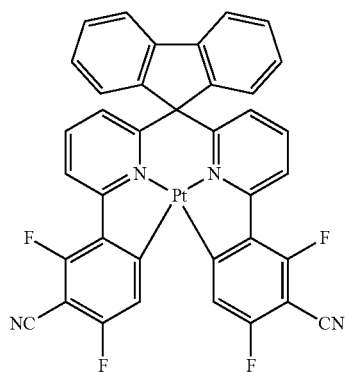
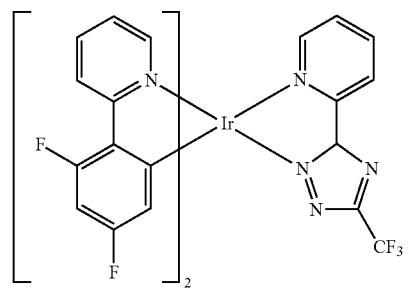

-continued

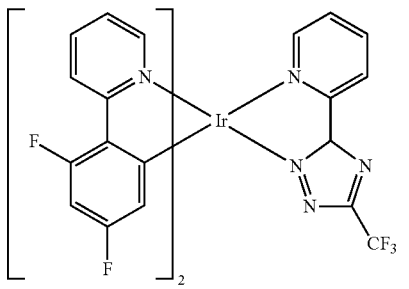

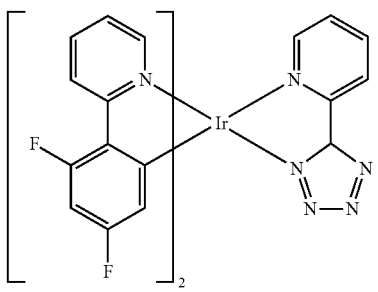

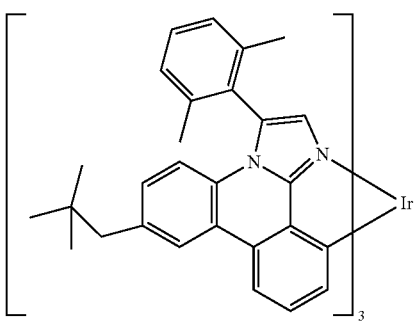

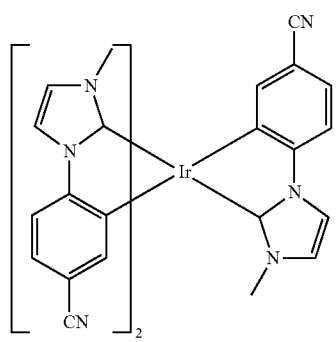

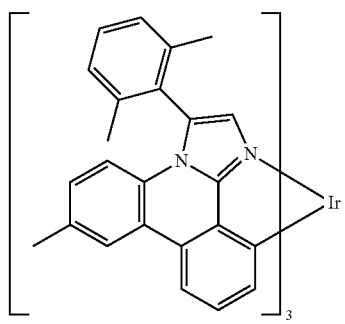

In a preferred embodiment of the invention, the compounds of the formula (I) are employed as hole-transport material. The compounds are then preferably employed in a hole-transport layer and/or in a hole-injection layer. For the purposes of this invention, a hole-injection layer is a layer which is directly adjacent to the anode. For the purposes of this invention, a hole-transport layer is a layer which is located between the hole-injection layer and the emission layer. The hole-transport layer may be directly adjacent to the emission layer. If the compounds of the formula (I) are used as hole-transport material or as hole-injection material, it may be preferred for them to be doped with electron-acceptor compounds, for example with $F_4$-TCNQ or with compounds as described in EP 1476881 or EP 1596445. In a further preferred embodiment of the invention, a compound of the formula (I) is used as hole-transport material in combination with a hexaazatriphenylene derivative as described in US 2007/0092755. The hexaazatriphenylene derivative is particularly preferably employed in its own layer here.

Thus, for example, preference is given to the following structure: anode-hexaazatriphenylene derivative-hole-transport layer, where the hole-transport layer comprises one or more compounds of the formula (I). It is likewise possible to use a plurality of successive hole-transport layers in this structure, where at least one hole-transport layer comprises at least one compound of the formula (I). The following structure is likewise preferred: anode-hole-transport layer-hexaazatriphenylene derivative-hole-transport layer, where at least one of the two hole-transport layers comprises one or more compounds of the formula (I). It is likewise possible in this structure for a plurality of successive hole-transport layers to be used instead of one hole-transport layer, where at least one hole-transport layer comprises at least one compound of the formula (I).

If the compound of the formula (I) is employed as hole-transport material in a hole-transport layer, the compound can be employed as pure material, i.e. in a proportion of 100% in the hole-transport layer, or it can be employed in combination with one or more further compounds in the hole-transport layer.

In a further embodiment of the present invention, the compounds of the formula (I) are employed as matrix material in combination with one or more dopants, preferably phosphorescent dopants.

A dopant is taken to mean the component whose proportion in the mixture is the smaller in a system comprising a matrix material and a dopant. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

Suitable phosphorescent dopants are the phosphorescent emitter compounds mentioned above.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a preferred embodiment of the invention, the compounds of the formula (I) are used as a component of mixed-matrix systems. The mixed-matrix systems preferably comprise two or three different matrix materials, particularly preferably two different matrix materials. The two different matrix materials here may be present in a ratio of 1:10 to 1:1, preferably in a ratio of 1:4 to 1:1. The mixed-matrix systems may comprise one or more dopants. The dopant compound or the dopant compounds together have, in accordance with the invention, a proportion of 0.1 to 50.0% by vol. in the mixture as a whole and preferably a proportion of 0.5 to 20.0% by vol. in the mixture as a whole. Correspondingly, the matrix components together have a proportion of 50.0 to 99.9% by vol. in the mixture as a whole and preferably a proportion of 80.0 to 99.5% by vol. in the mixture as a whole.

Mixed-matrix systems are preferably employed in phosphorescent organic electroluminescent devices.

Particularly suitable matrix materials, which can be employed in combination with the compounds according to the invention as matrix components of a mixed-matrix system, are aromatic ketones, aromatic phosphine oxides or aromatic sulfoxides or sulfones, for example in accordance with WO 04/013080, WO 04/093207, WO 06/005627 or WO 10/006680, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 08/086851, indolocarbazole derivatives, for example in accordance with WO 07/063754 or WO 08/056746, azacarbazole derivatives, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with WO 2010/015306, WO 07/063754 or WO 08/056746, zinc complexes, for example in accordance with EP 652273 or WO 09/062578, diazasilole or tetraazasilole derivatives, for example in accordance with WO 10/054729, diazaphosphole derivatives, for example in accordance with WO 10/054730, or indenocarbazole derivatives, for example in accordance with WO 10/136109.

The invention thus furthermore relates to mixtures comprising one or more compounds of the formula (I) and one or more further compounds selected from phosphorescent dopants and/or further matrix materials, preferably aromatic ketones, aromatic phosphine oxides or aromatic sulfoxides or sulfones, triarylamines, carbazole derivatives, indolocarbazole derivatives, azacarbazole derivatives, bipolar matrix materials, silanes, azaboroles or boronic esters, triazine derivatives, zinc complexes, diazasilole or tetraazasilole derivatives, diazaphosphole derivatives and indenocarbazole derivatives.

Preferred phosphorescent dopants for use in mixed-matrix systems comprising the compounds according to the invention are the phosphorescent dopants mentioned in the above table.

In a further embodiment of the invention, the compounds of the formula (I) are employed as emitting materials in an emitting layer. The compounds are suitable, in particular, as emitting compounds If they contain at least one diarylamino group. In this case, the compounds according to the invention are particularly preferably used as green or blue emitters.

The proportion of the compound of the formula (I) as dopant in the mixture of the emitting layer is in this case between 0.1 and 50.0% by vol., preferably between 0.5 and 20.0% by vol., particularly preferably between 0.5 and 8.0% by vol. Correspondingly, the proportion of the matrix material is between 50.0 and 99.9% by vol., preferably between 80.0 and 99.5% by vol., particularly preferably between 92.0 and 99.5% by vol.

Preferred matrix materials for use in combination with the compounds according to the invention as emitters are mentioned in one of the following sections. They correspond to the matrix materials for fluorescent emitters that are mentioned as preferred.

The materials preferably employed for the respective functions or in the respective functional layers in the electronic devices according to the invention are mentioned below.

Preferred fluorescent emitter materials are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitter materials are selected from indenofluorenamines or indenofluorenediamines, for example in accordance with WO 06/122630, benzoindenofluorenamines or benzoindenofluorenediamines, for example in accordance with WO 08/006449, and dibenzoindenofluorenamines or dibenzoindenofluorenediamines, for example in accordance with WO 07/140847. Examples of emitter materials from the class of the styrylamines are substituted or unsubstituted tristilbenamines or the emitter materials described in WO 06/000388, WO 06/058737, WO 06/000389, WO 07/065549 and WO 07/115610. Preference is furthermore given to the condensed hydrocarbons disclosed in the application WO 10/012328.

Preferred fluorescent emitter materials are furthermore the compounds of the formula (I) according to the invention.

Suitable emitter materials are furthermore the structures depicted in the following table, and the derivatives of these structures disclosed in JP 06/001973, WO 04/047499, WO 06/098080, WO 07/065678, US 2005/0260442 and WO 04/092111.

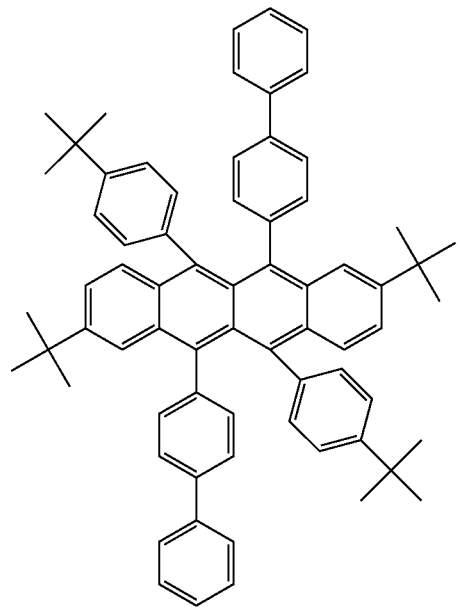 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]

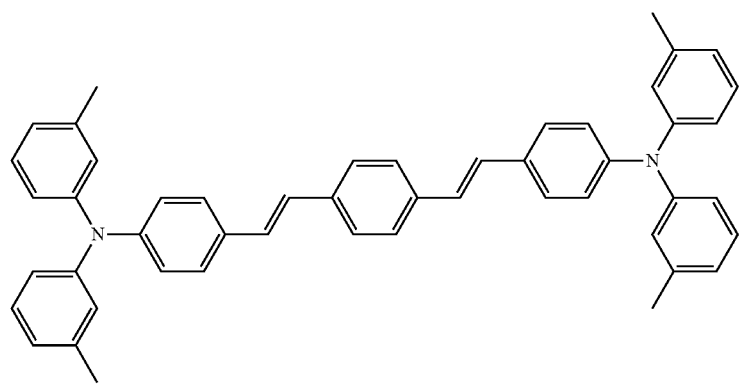 [SMILES: Cc1cccc(N(c2ccc(/C=C/c3ccc(/C=C/c4ccc(N(c5cccc(C)c5)c5cccc(C)c5)cc4)cc3)cc2)c2cccc(C)c2)c1]

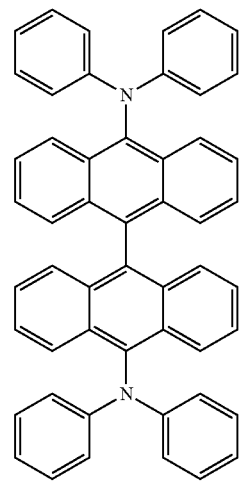 [SMILES: c1ccc(N(c2ccccc2)c2c3ccccc3c(-c3c4ccccc4c(N(c4ccccc4)c4ccccc4)c4ccccc34)c3ccccc23)cc1]

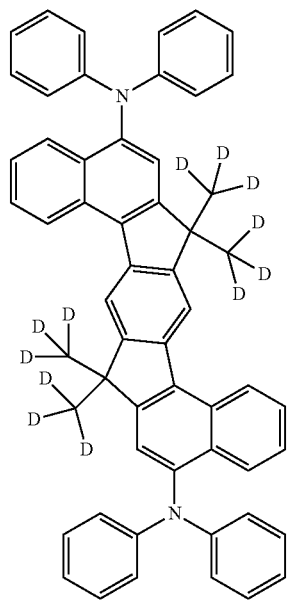 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]
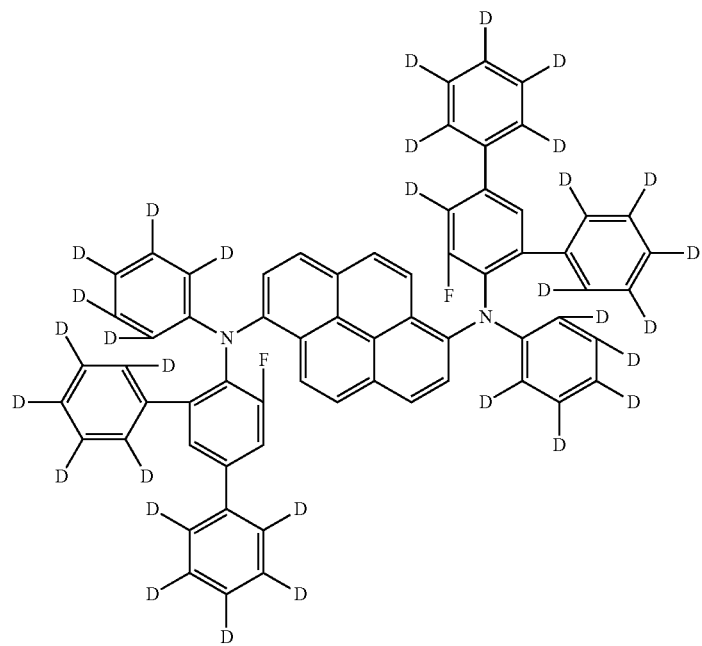 [SMILES: [2H]c1c([2H])c([2H])c(-c2cc(F)c(N(c3c([2H])c([2H])c([2H])c([2H])c3[2H])c3ccc4ccc5c(N(c6c([2H])c([2H])c([2H])c([2H])c6[2H])c6c(-c7c([2H])c([2H])c([2H])c([2H])c7[2H])cc(-c7c([2H])c([2H])c([2H])c([2H])c7[2H])c([2H])c6F)ccc6ccc3c4c65)c(-c3c([2H])c([2H])c([2H])c([2H])c3[2H])c2)c([2H])c1[2H]]
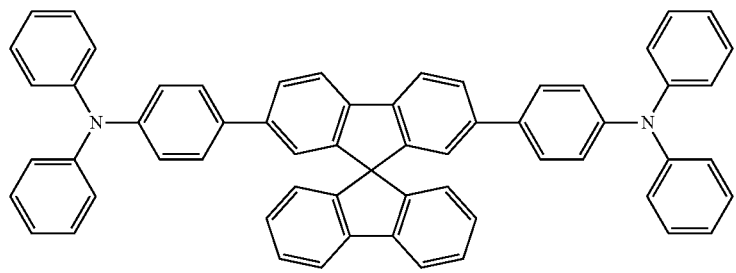 [SMILES: c1ccc(N(c2ccccc2)c2ccc(-c3ccc4c(c3)C3(c5ccccc5-c5ccccc53)c3cc(-c5ccc(N(c6ccccc6)c6ccccc6)cc5)ccc3-4)cc2)cc1]

-continued
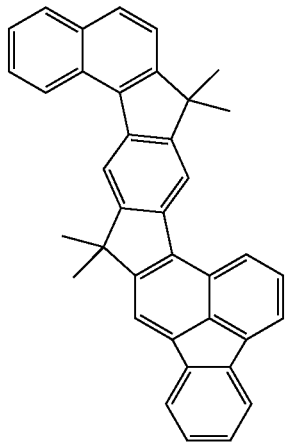 [SMILES: CC1(C)c2cc3c(cc2-c2c1ccc1ccccc21)C(C)(C)c1cc2c4c(cccc4c1-3)-c1ccccc1-2]
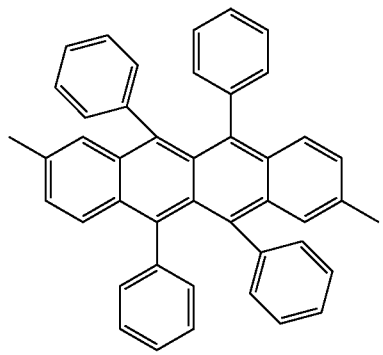
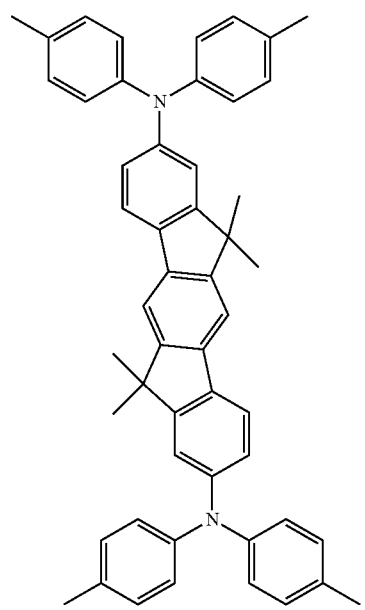

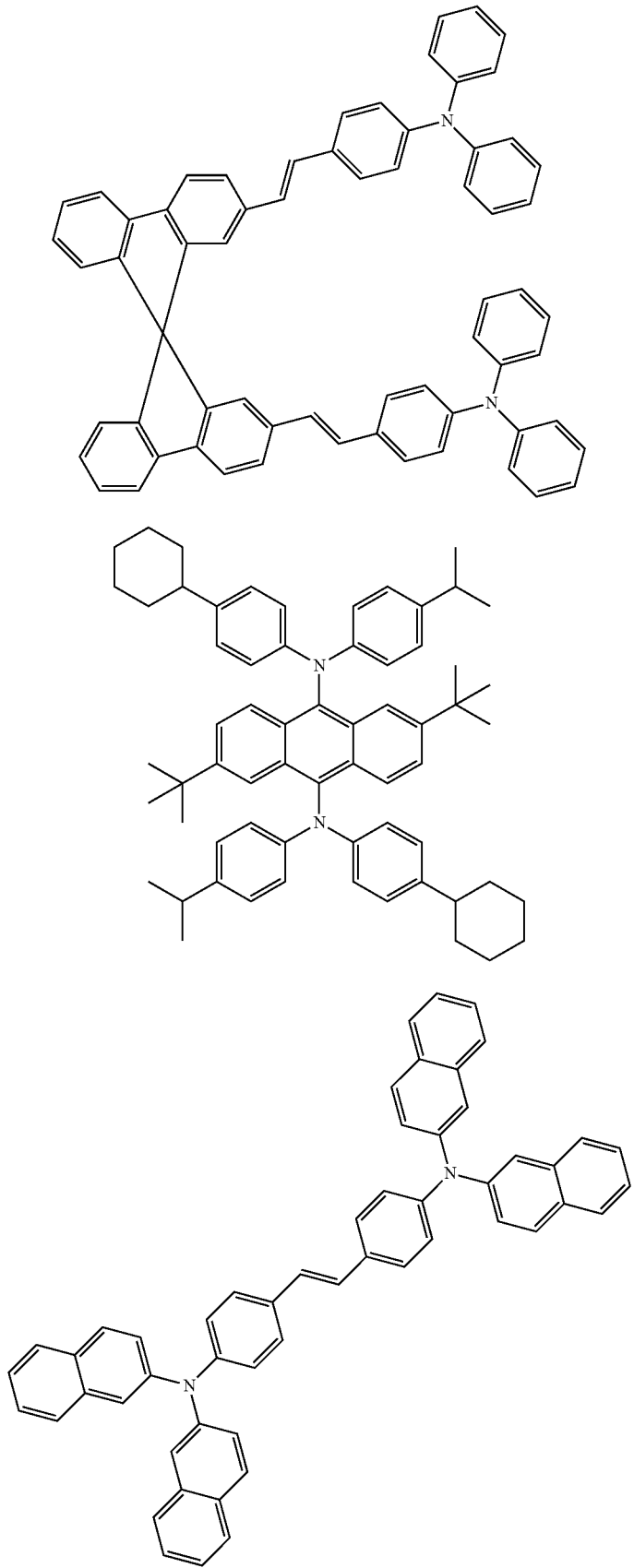

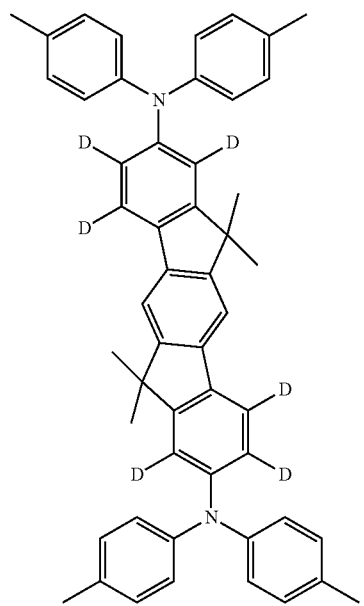
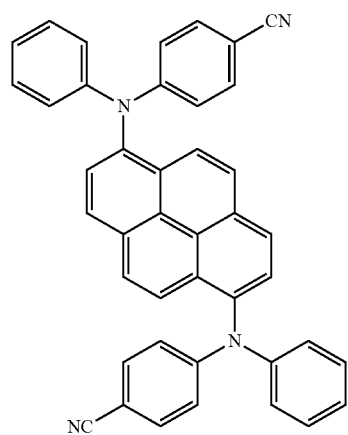 [SMILES: N#Cc1ccc(N(c2ccccc2)c2ccc3ccc4c(N(c5ccccc5)c5ccc(C#N)cc5)ccc5ccc2c3c54)cc1]

-continued
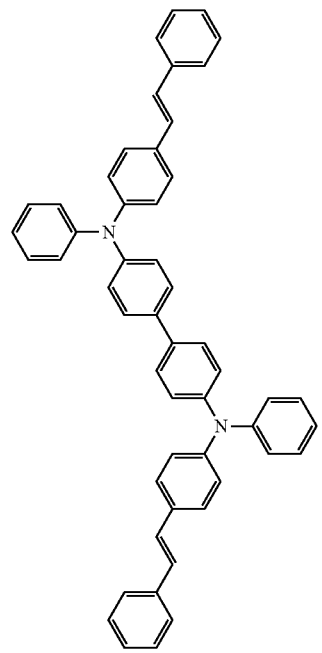 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]
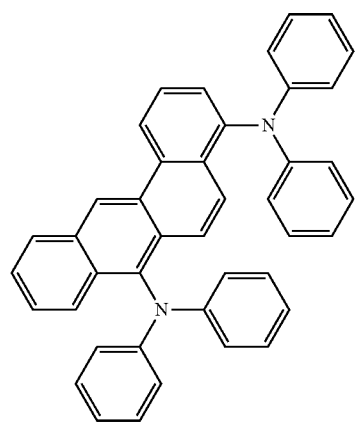 [SMILES: c1ccc(N(c2ccccc2)c2cccc3c2ccc2c(N(c4ccccc4)c4ccccc4)c4ccccc4cc23)cc1]
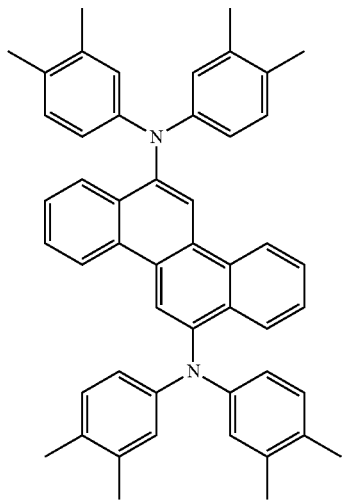

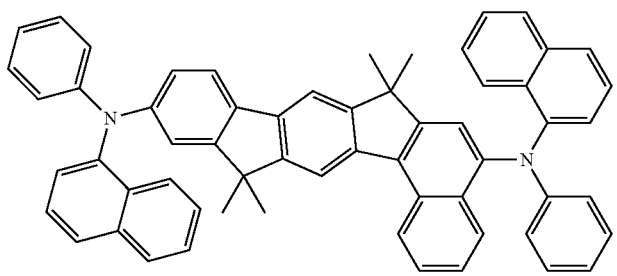 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
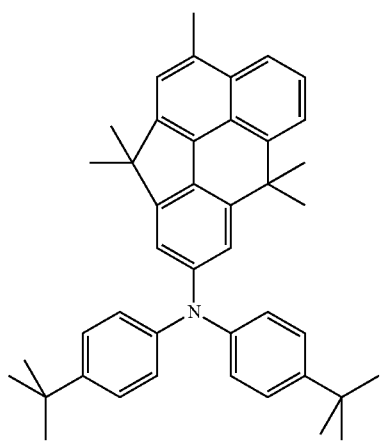 [SMILES: Cc1cc2c3c4c(cccc14)C(C)(C)c1cc(N(c4ccc(C(C)(C)C)cc4)c4ccc(C(C)(C)C)cc4)cc(c1-3)C2(C)C]
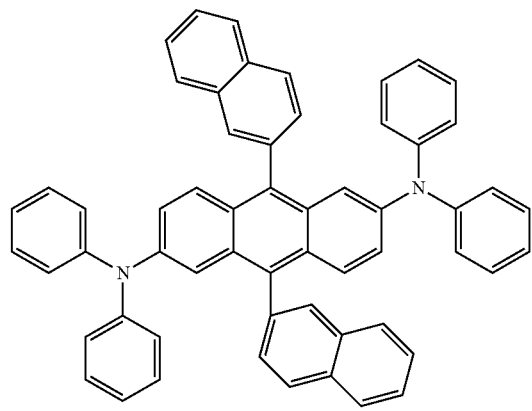 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]
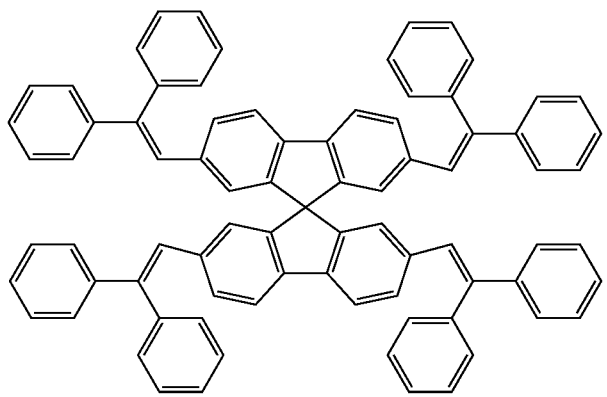 [SMILES: C(=C(c1ccccc1)c1ccccc1)c1ccc2c(c1)C1(c3cc(C=C(c4ccccc4)c4ccccc4)ccc3-2)c2cc(C=C(c3ccccc3)c3ccccc3)ccc2-c2ccc(C=C(c3ccccc3)c3ccccc3)cc21]

-continued
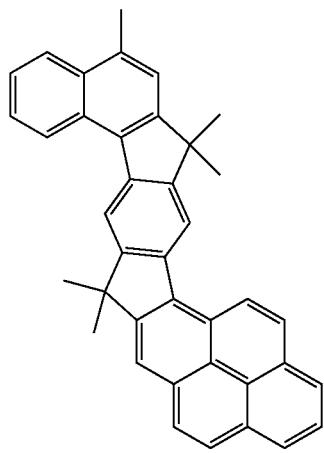 [SMILES: Cc1cc2c(c3ccccc13)-c1cc3c(cc1C2(C)C)-c1c(cc2ccc4cccc5ccc1c2c45)C3(C)C]
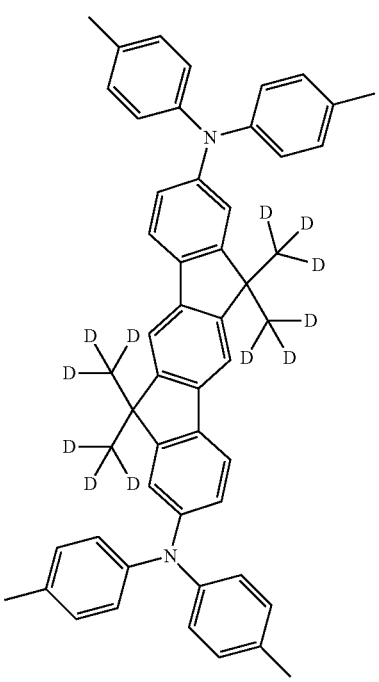
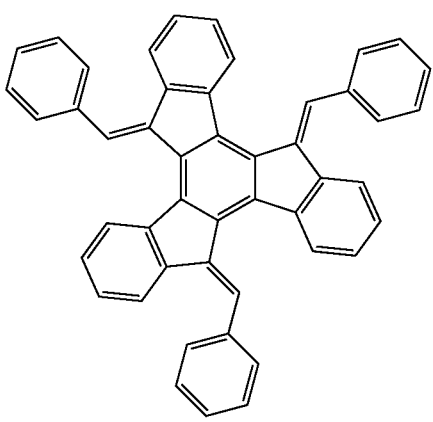 [SMILES: C(=C1/c2ccccc2-c2c1c1c(c3c2/C(=C/c2ccccc2)c2ccccc2-3)/C(=C/c2ccccc2)c2ccccc2-1)/c1ccccc1]

-continued
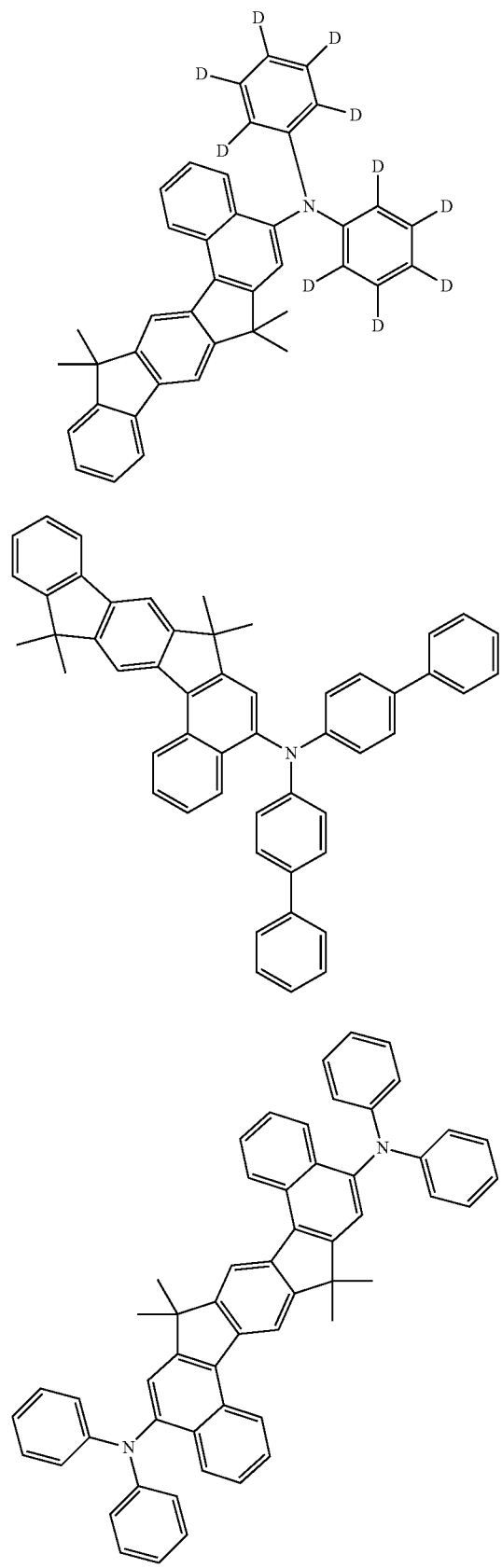

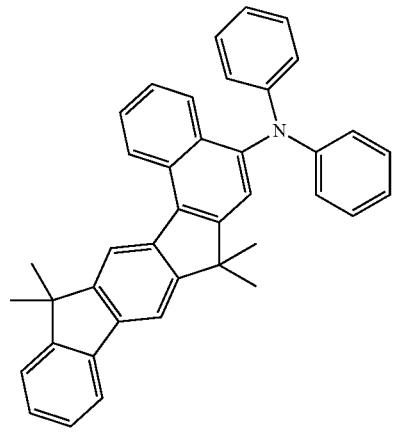 [SMILES: CC1(C)c2ccccc2-c2cc3c(cc21)-c1c(cc(N(c2ccccc2)c2ccccc2)c2ccccc12)C3(C)C]
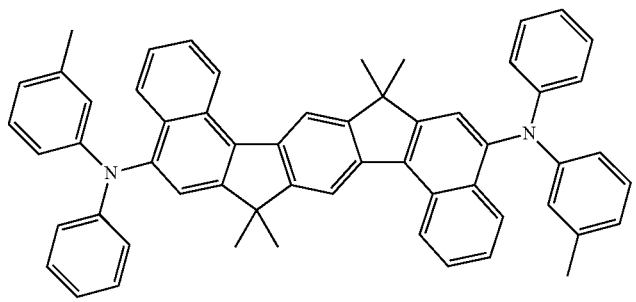 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1]
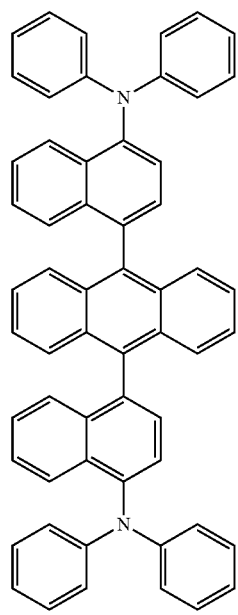 [SMILES: c1ccc(N(c2ccccc2)c2ccc(-c3c4ccccc4c(-c4ccc(N(c5ccccc5)c5ccccc5)c5ccccc45)c4ccccc34)c3ccccc23)cc1]

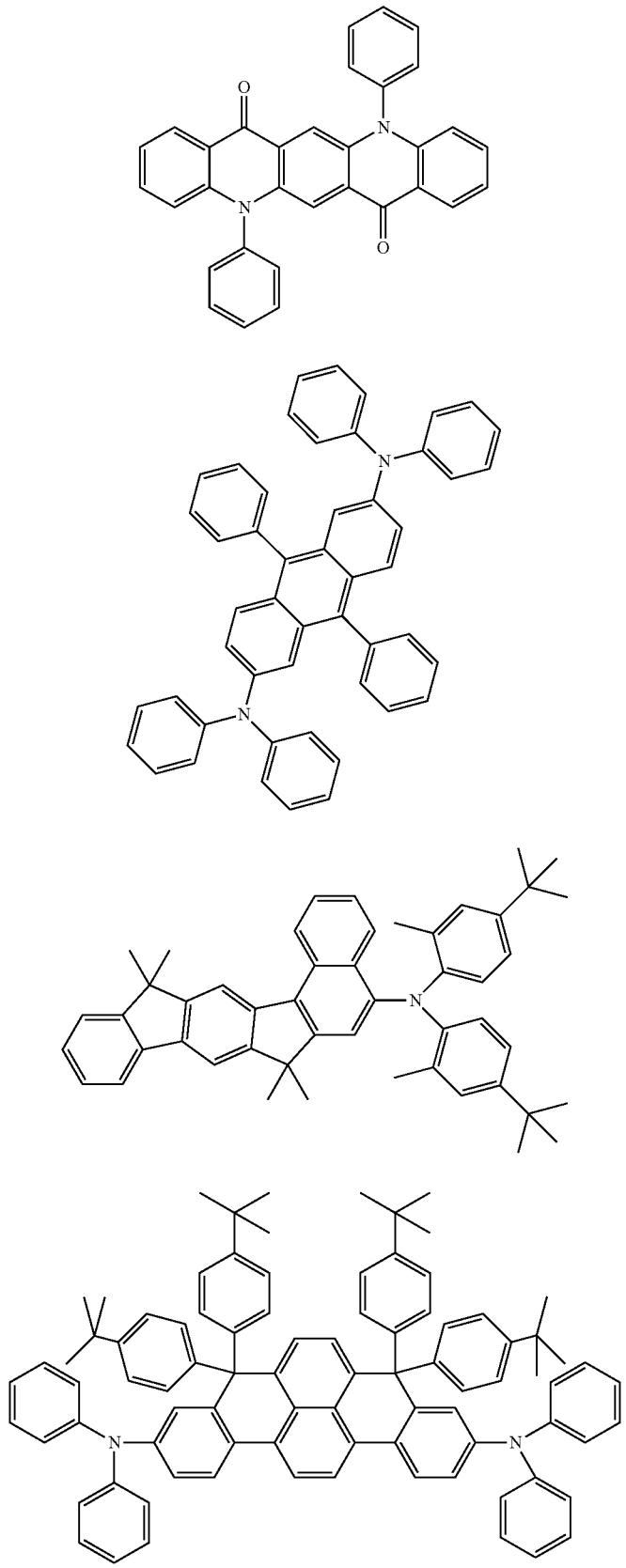

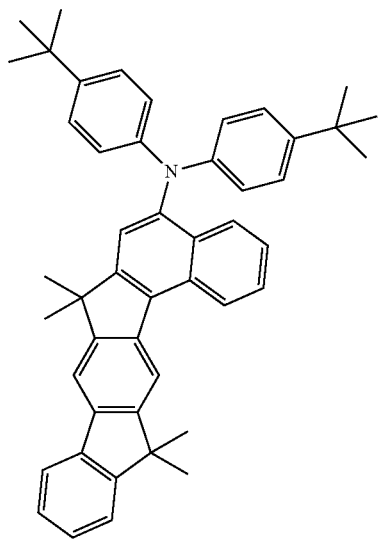 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
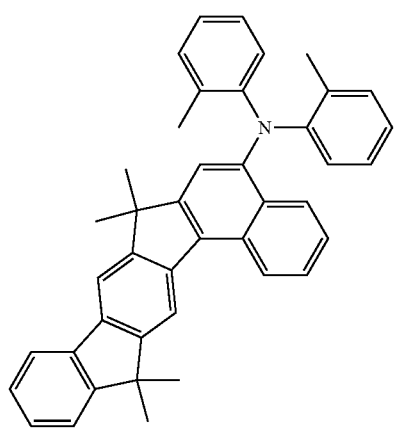 [SMILES: Cc1ccccc1N(c1ccccc1C)c1cc2c(c3ccccc13)-c1cc3c(cc1C2(C)C)-c1ccccc1C3(C)C]
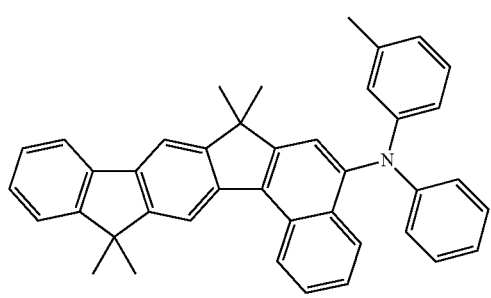 [SMILES: Cc1cccc(N(c2ccccc2)c2cc3c(c4ccccc24)-c2cc4c(cc2C3(C)C)-c2ccccc2C4(C)C)c1]
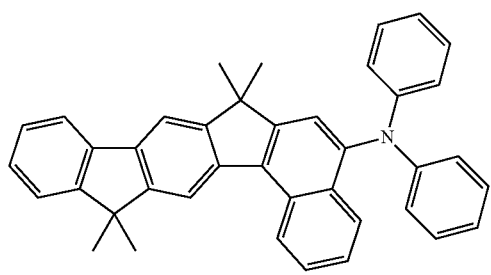 [SMILES: CC1(C)c2ccccc2-c2cc3c(cc21)-c1c(cc(N(c2ccccc2)c2ccccc2)c2ccccc12)C3(C)C]

-continued
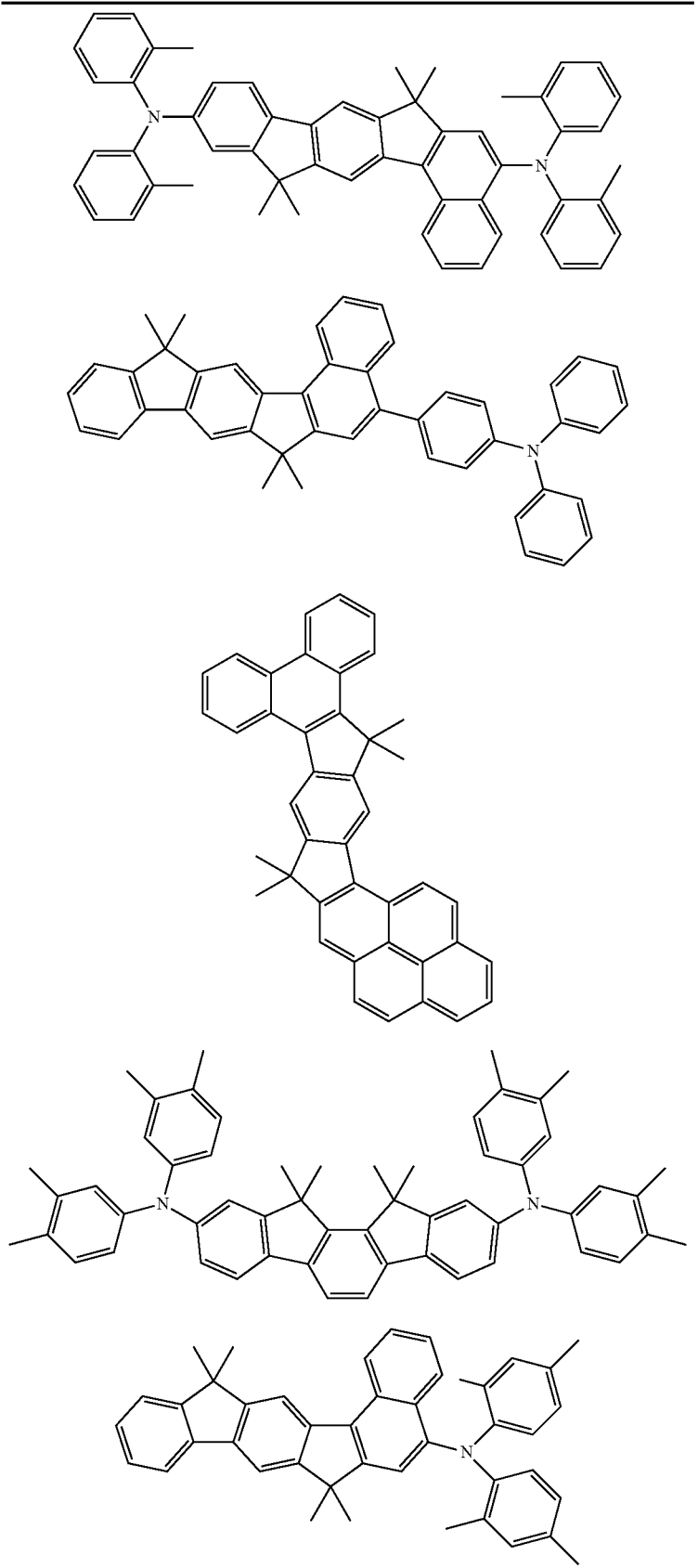

-continued
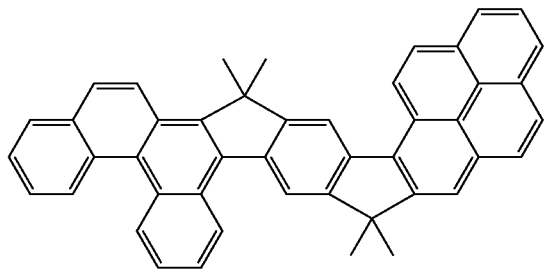 [SMILES: CC1(C)c2cc3c(cc2-c2c1cc1ccc4cccc5ccc2c1c45)C(C)(C)c1c-3c2ccccc2c2c1ccc1ccccc12]
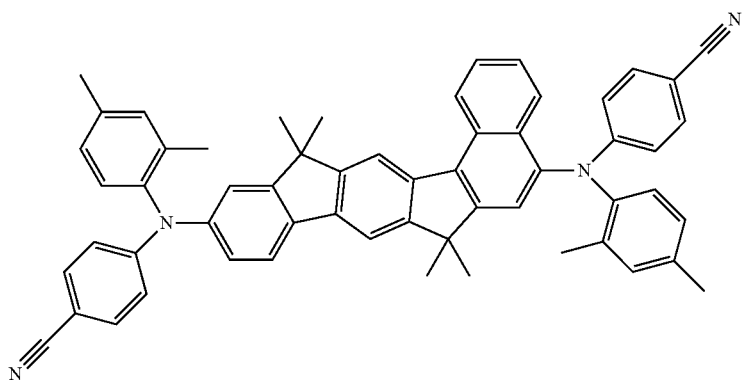 [SMILES: Cc1ccc(N(c2ccc(C#N)cc2)c2ccc3c(c2)C(C)(C)c2cc4c(cc2-3)C(C)(C)c2cc(N(c3ccc(C#N)cc3)c3ccc(C)cc3C)c3ccccc3c2-4)c(C)c1]
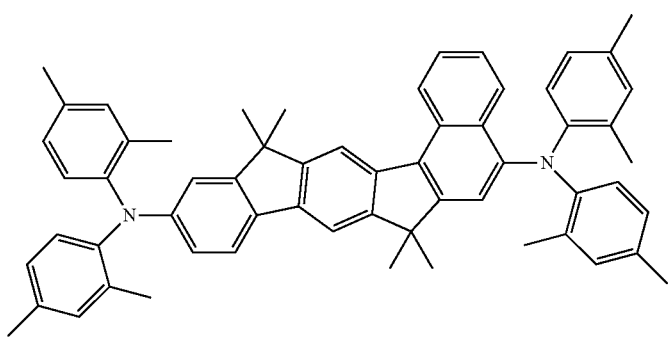
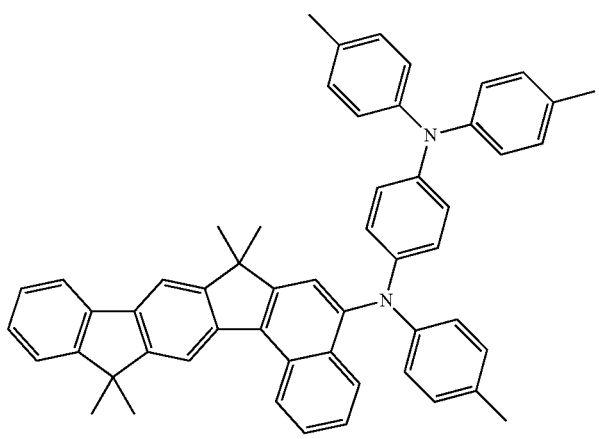 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]

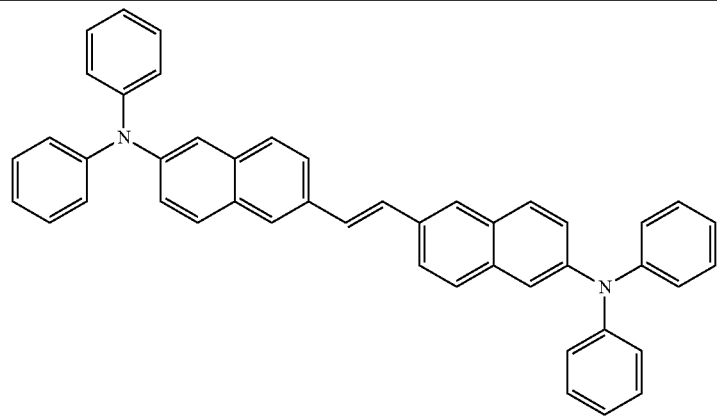

Matrix materials which can be used, preferably for fluorescent dopants, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145239). Suitable matrix materials are furthermore preferably the compounds according to the invention. Apart from the compounds according to the invention, particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable matrix materials, preferably for fluorescent dopants, are, for example, the materials depicted in the following table, and derivatives of these materials, as disclosed in WO 04/018587, WO 08/006449, U.S. Pat. No. 5,935,721, US 2005/0181232, JP 2000/273056, EP 681019, US 2004/0247937 and US 2005/0211958.

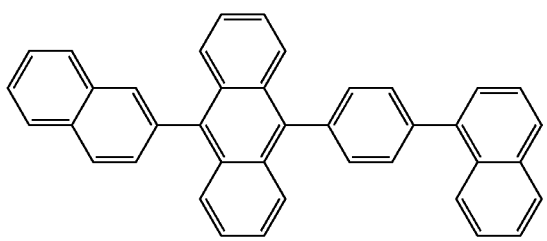 [SMILES: c1ccc2cc(-c3c4ccccc4c(-c4ccc(-c5cccc6ccccc56)cc4)c4ccccc34)ccc2c1]

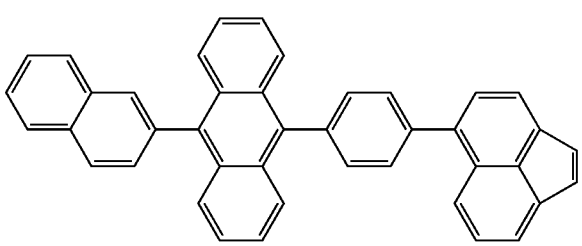 [SMILES: C1=Cc2ccc(-c3ccc(-c4c5ccccc5c(-c5ccc6ccccc6c5)c5ccccc45)cc3)c3cccc1c23]

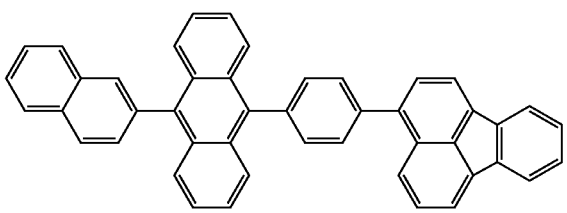 [SMILES: c1ccc2c(c1)-c1cccc3c(-c4ccc(-c5c6ccccc6c(-c6ccc7ccccc7c6)c6ccccc56)cc4)ccc-2c13]

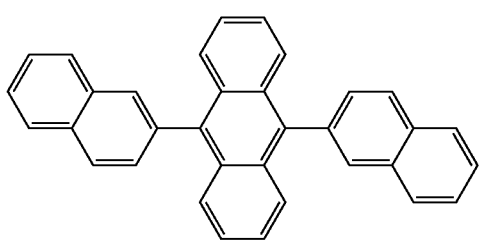 [SMILES: c1ccc2cc(-c3c4ccccc4c(-c4ccc5ccccc5c4)c4ccccc34)ccc2c1]

| 109 -continued | 110 -continued |
|---|---|
| 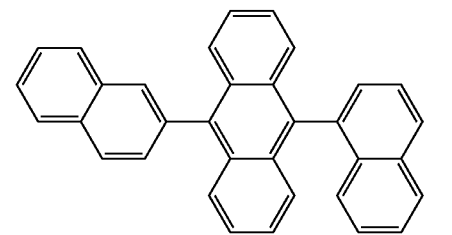 [SMILES: c1ccc2cc(-c3c4ccccc4c(-c4cccc5ccccc45)c4ccccc34)ccc2c1] | 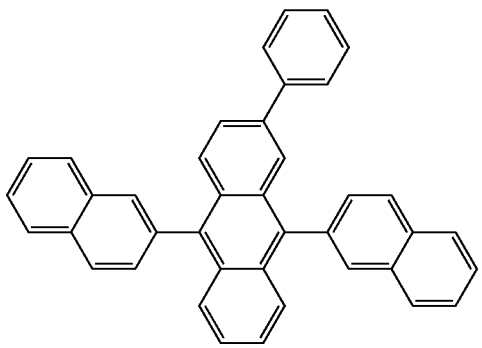 |
| 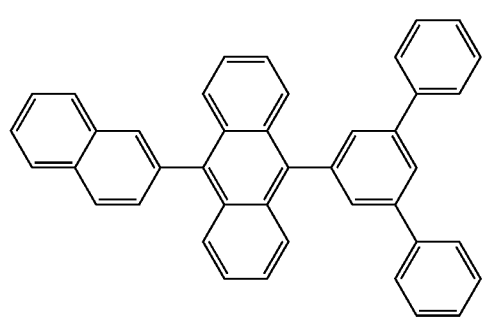 [SMILES: c1ccc(-c2cc(-c3ccccc3)cc(-c3c4ccccc4c(-c4ccc5ccccc5c4)c4ccccc34)c2)cc1] | 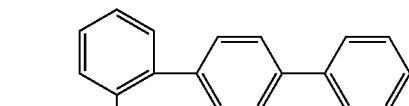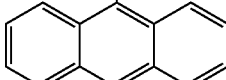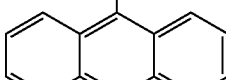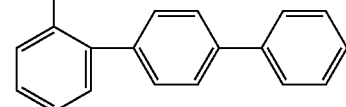 |
| 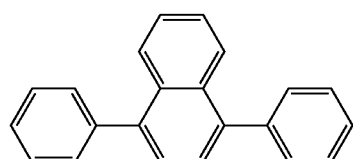 | 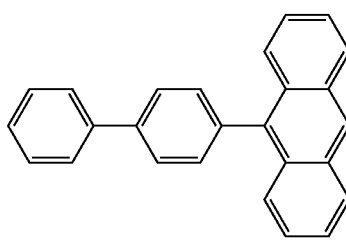 |
| 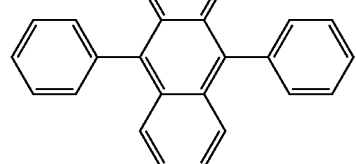 | 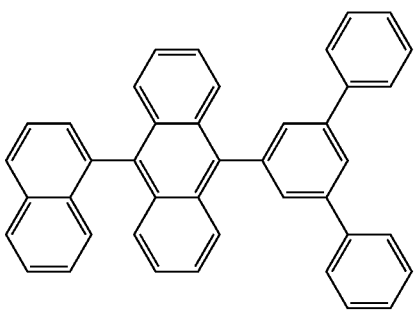 [SMILES: c1ccc(-c2cc(-c3ccccc3)cc(-c3c4ccccc4c(-c4cccc5ccccc45)c4ccccc34)c2)cc1] |
| | |

| 111 -continued | 112 -continued |
|---|---|
| 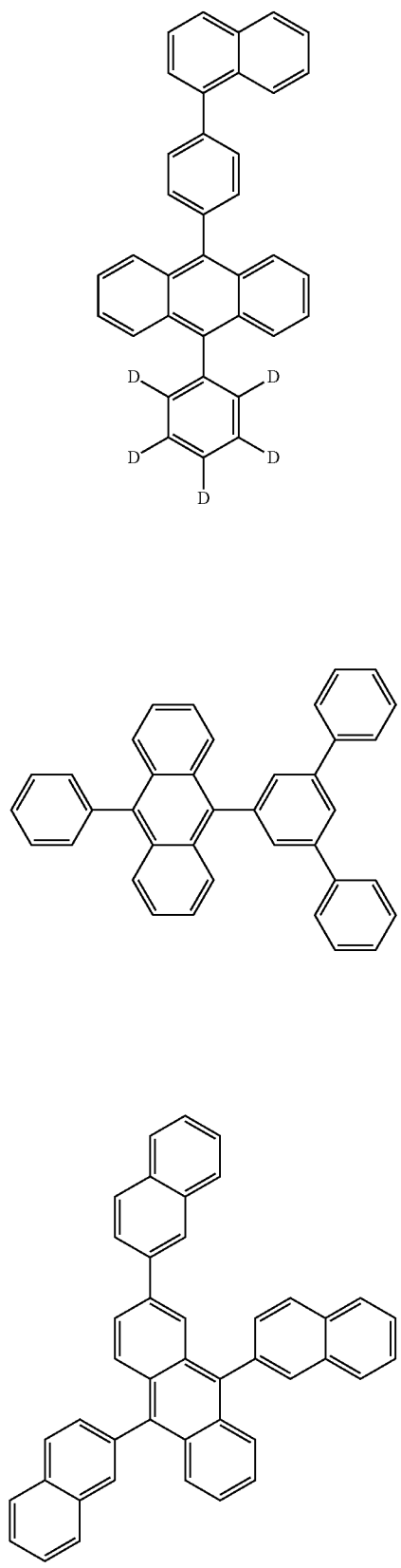 | 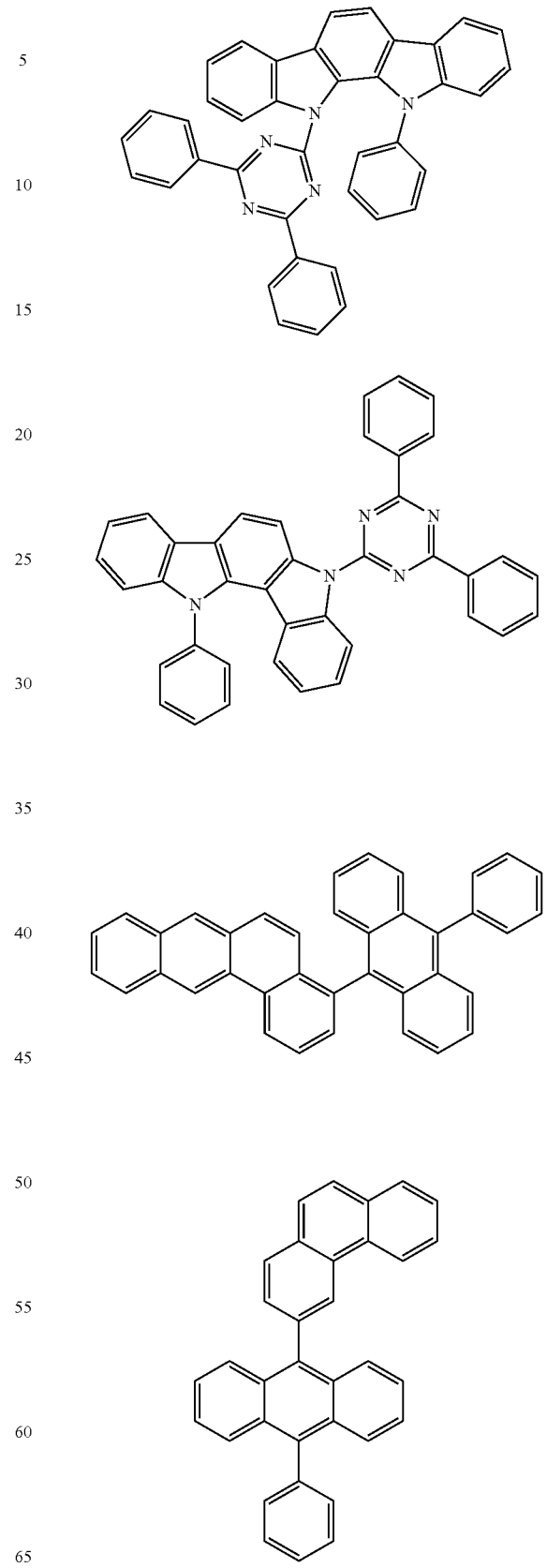 |

-continued
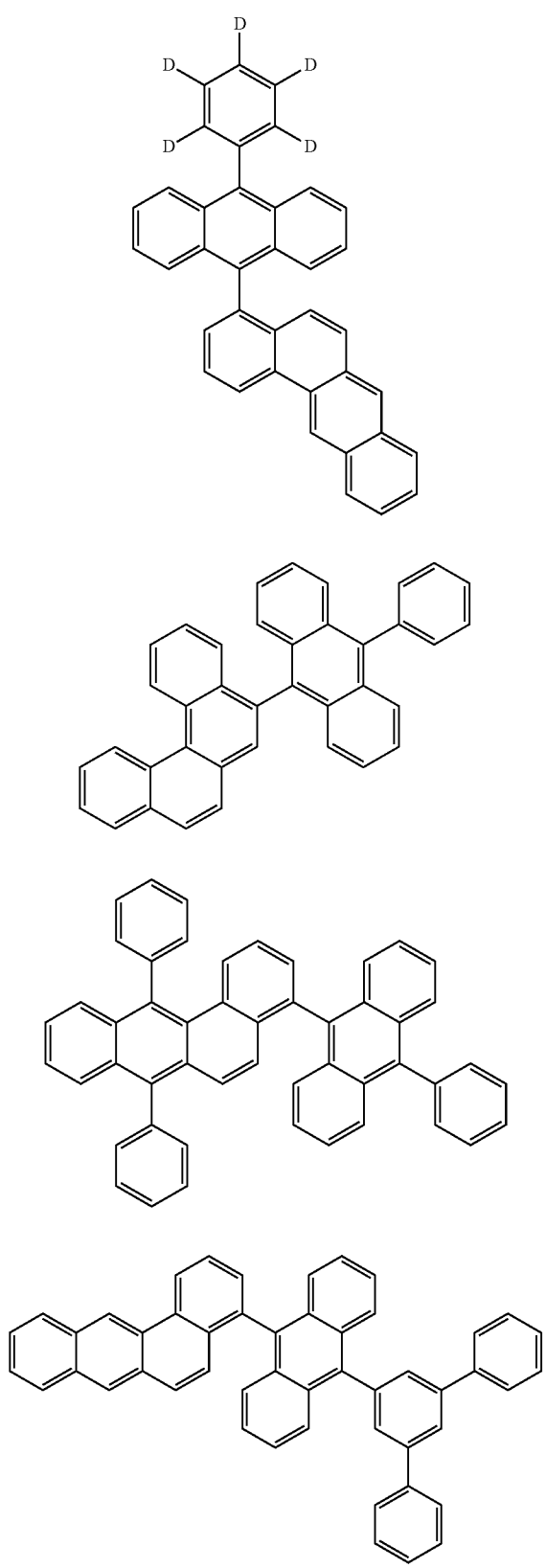
-continued
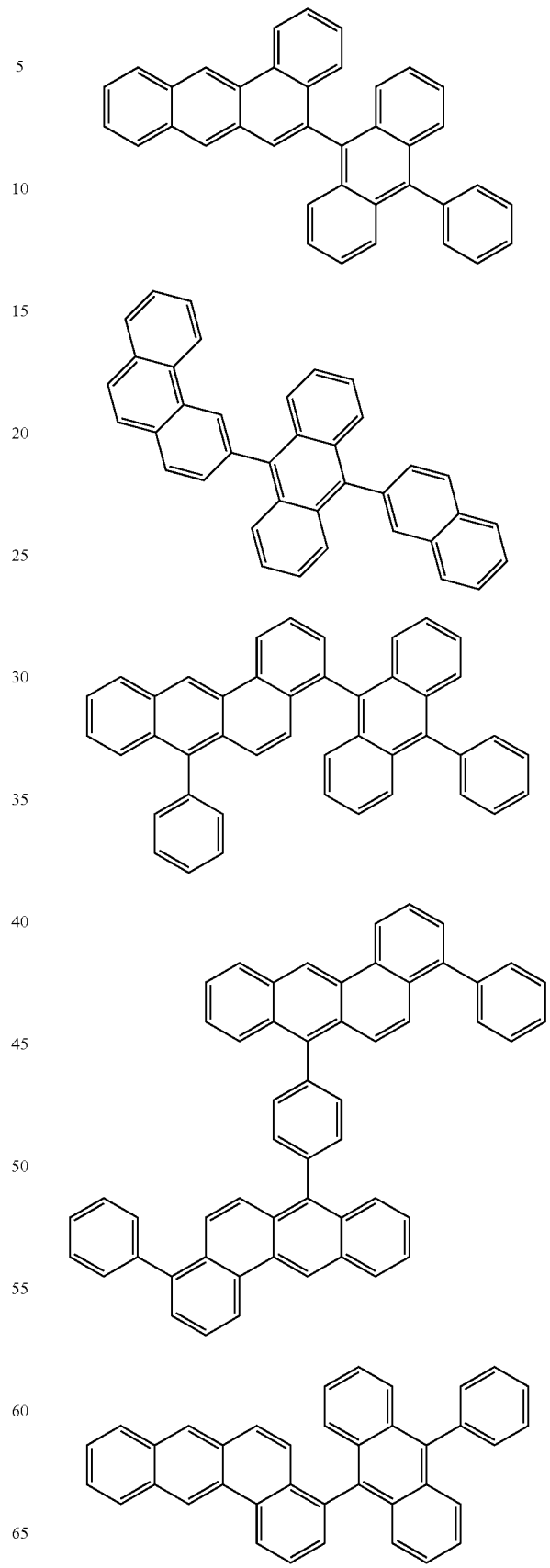

| 115 -continued | 116 -continued |
|---|---|
| 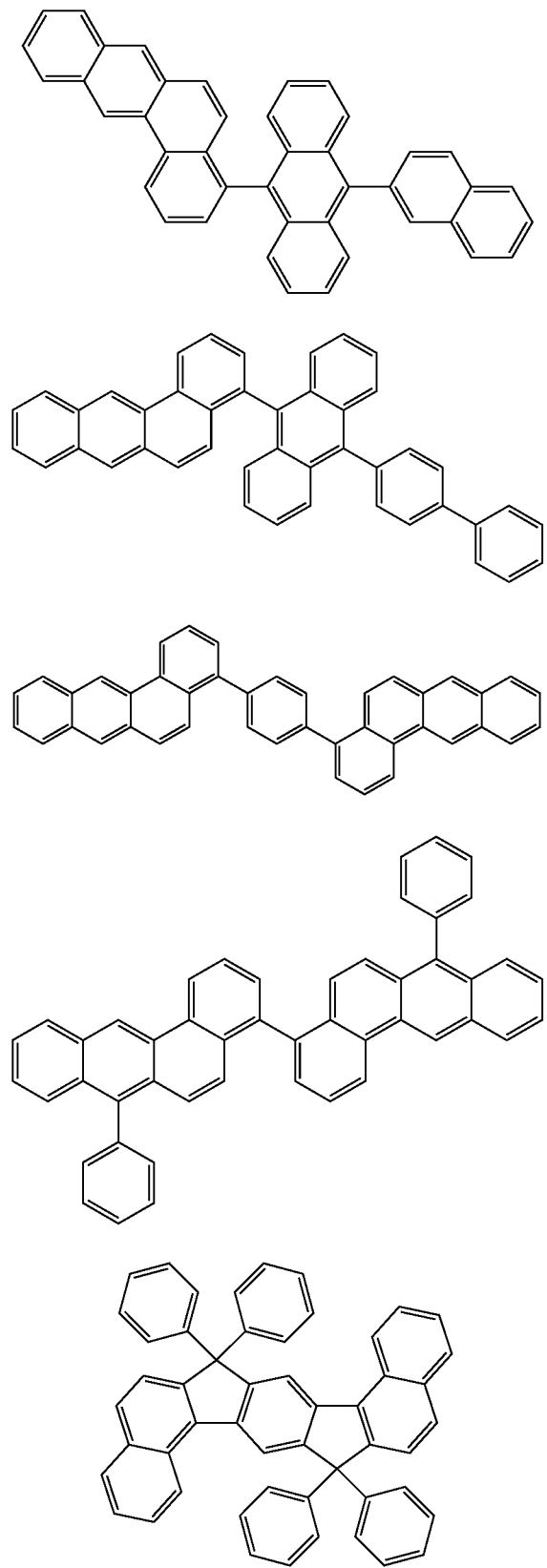 | 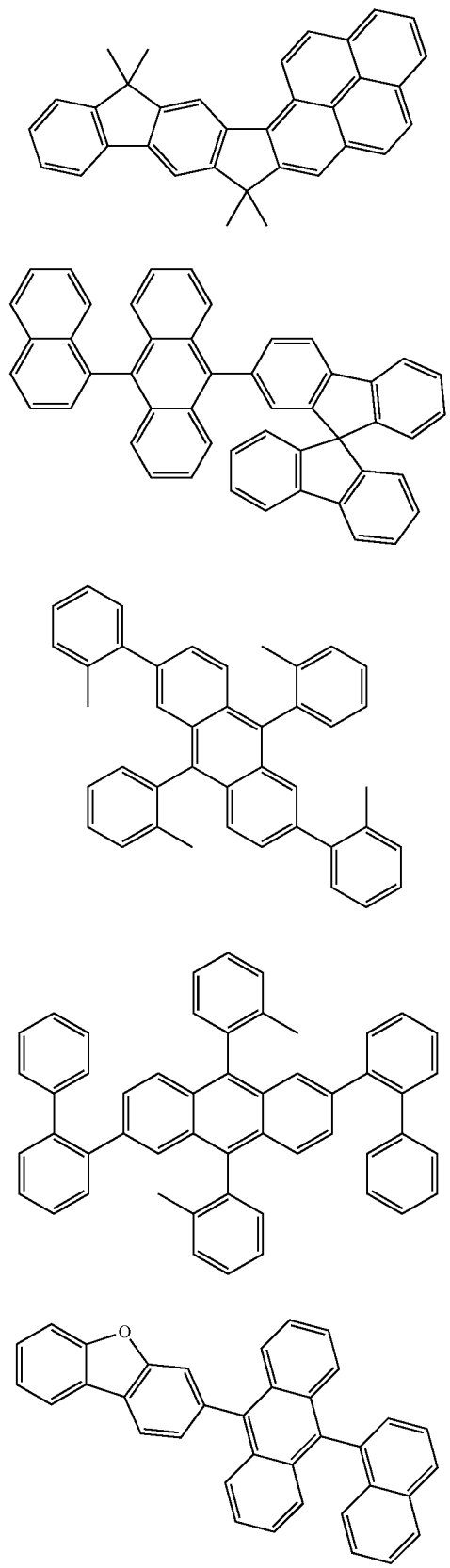 |

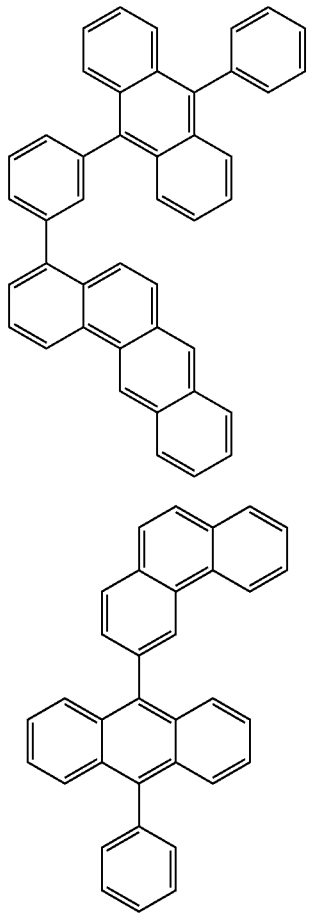

Preferred matrix materials for phosphorescent dopants are carbazole derivatives (for example CBP (N,N-biscarbazolyl-biphenyl) or compounds in accordance with WO 2005/039246, US 2005/0069729, JP 2004/288381, EP 1205527 or WO 2008/086851), triarylamines, azacarbazoles (for example in accordance with EP 1617710, EP 1617711, EP 1731584, JP 2005/347160), indolocarbazole derivatives, for example in accordance with WO 2007/063754 or WO 2008/056746), ketones (for example in accordance with WO 2004/093207 or WO 2010/006680), phosphine oxides, sulfoxides and sulfones (for example in accordance with WO 2005/003253), oligophenylenes, aromatic amines (for example in accordance with US 2005/0069729), bipolar matrix materials (for example in accordance with WO 2007/137725), silanes (for example in accordance with WO 2005/111172), azaboroles or boronic esters, for example in accordance with WO 2006/117052, triazine derivatives, for example in accordance with WO 2010/015306, WO 2007/063754 or WO 2008/056746, zinc complexes (for example in accordance with WO 2009/062578), aluminium complexes (for example BAlq), diazasilole and tetraazasilole derivatives, for example in accordance with WO 2010/054730, indenocarbazole derivatives, for example in accordance with WO 2010/136109 and WO 2011/000455, or diazaphospholes, for example in accordance with WO 2010/054730.

Besides the compounds according to the invention, suitable charge-transport materials, as can be used in the hole-injection or hole-transport layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ba/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds of the formula (I) can be employed in displays, as light sources in lighting applications and as light sources in medical and/or cosmetic applications (for example in light therapy).

The compounds according to the invention have excellent hole mobility and are therefore very highly suitable as hole-transport materials. The high hole mobility enables a reduction in the operating voltage and an improvement in the operating lifetime of the electronic devices comprising the compounds according to the invention. Furthermore, the compounds according to the invention, on use in electronic devices, result in higher power efficiency of the devices.

Furthermore, the compounds of the formula (I) are distinguished by high oxidation stability in solution, which has an advantageous effect during purification and handling of the compounds and on use thereof in electronic devices.

The compounds are furthermore eminently suitable for use as matrix materials in mixed-matrix systems, where they preferably result in a reduction in the operating voltage and an increase in the lifetime of the electronic devices.

Furthermore, the compounds of the formula (I) are temperature-stable and can thus be sublimed substantially without decomposition. Purification of the compounds is thus simplified, and the compounds can be obtained in higher purity, which has a positive effect on the performance data of the electronic devices comprising the materials. In particular, devices having longer operating lifetimes can thus be produced.

The invention is explained in greater detail by the following working examples, without wishing it to be restricted thereby.

USE EXAMPLES

I. Synthesis Examples

A) 5,8-Bisbiphenyl-4-yl-13,13-dimethyl-8,13-dihydro-5H-5,8-diazaindeno[1,2-a]anthracene A 1) Synthesis of Tert-butyl 3-bromocarbazole-9-carboxylate A1

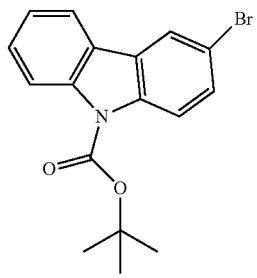

A1

147.12 g (674.1 mmol) of di-tert-butyl dicarbonate are dissolved in 1000 ml of degassed THF, and 118.5 g (481.5 mmol) of 3-bromo-9H-carbazole and 5.94 g (48.15 mmol) of DMAP are added (caution: evolution of gas!). The reaction mixture is subsequently slowly heated under reflux. The cooled reaction solution is carefully added to water and extracted with methylene chloride and dried, giving a yellow oil, which is washed by stirring with hot heptane and crystallised with ultrasound treatment, giving 116.1 g (69%) of the product as a white solid.

2) Synthesis of Tert-butyl 3-(2-methoxycarbonyl-phenylamino)carbazole-9-carboxylate A2

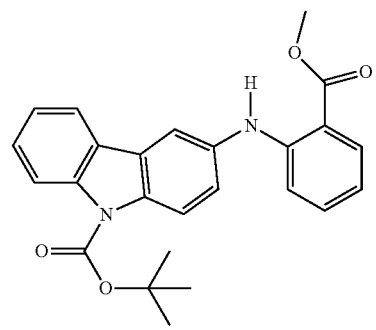

A2

63.4 g (183.12 mmol) of the bromide A1 are dissolved in 1200 ml of dry toluene with 39.0 ml (302.15 mmol) of methyl anthranilate, and 27.4 ml (27.4 mmol, 1 M in toluene) of tris-tert-butylphosphine are added via a syringe. 103.2 g (316.8 mmol) of $Cs_2CO_3$ and 3.28 g (14.7 mmol) of $Pd(OAc)_2$ are added, and the mixture is heated under reflux for about 2.5 h. When the conversion is complete, the cooled batch is filtered through silica gel and evaporated in a rotary evaporator. MeOH is added to the oil obtained, and the mixture is stirred at 50° C. for 3 min. The precipitate which deposits is washed a number of times with a little MeOH, giving 63.1 g (83%) of the product as beige crystals.

3) Synthesis of Methyl 2-(9H-carbazol-3-ylamino)benzoate A3

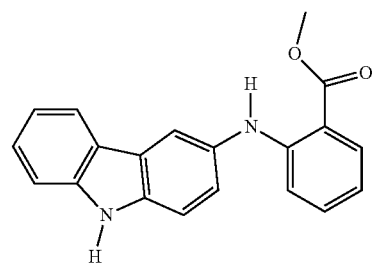

A3

80.5 g (193.3 mmol) of the ester A2 are dissolved in 600 ml of dichloromethane and 4.2 ml (38.5 mmol) of anisole. 15.7 ml of trifluoroacetic acid are then slowly added at room temperature, and the reaction mixture is heated to 40° C. Anisole and trifluoroacetic acid are subsequently added a number of times in portions until the conversion is complete. The cooled reaction mixture is subsequently added to icewater and carefully, but as rapidly as possible, adjusted to pH=7-8 using 20% NaOH solution. The mixture is extracted with methylene chloride, dried, filtered and evaporated. The oily solid obtained is washed by stirring with warm heptane, giving 43.9 g (72%) of the product as a solid.

4) Synthesis of 2-[2-(9H-carbazol-3-ylamino)phenyl]propan-2-ol A4

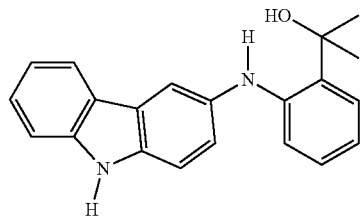

A4

43.9 g (138.8 mmol) of the ester A3 are dissolved in dry THF and cooled to −78° C. 315.4 ml (693.8 mmol, 2.2 M in diethyl ether) of MeLi are added dropwise at this temperature. Complete conversion is observed after about 5 h at a temperature of −40° C. 240 ml of MeOH are slowly added at −30° C. (caution: evolution of gas commences), and the mixture is extracted with ethyl acetate and water. The organic phase is dried, and the yellow solid obtained is washed by stirring with warm heptane, giving 42.7 g (97%) of the product as yellow-beige crystals.

5) Synthesis of 13,13-dimethyl-8,13-dihydro-5H-5,8-diazaindeno[1,2-a]-anthracene A5

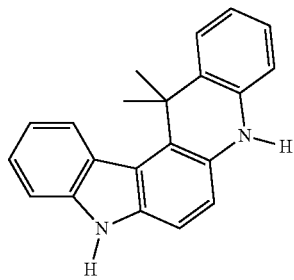

A5

42.6 g of the alcohol A4 are dissolved in 1000 ml of dichloromethane and cooled to −5° C. A mixture of 87.4 ml (1.35 mol) of methanesulfonic acid (10 eq.) and 118.8 g (1.21 mol) of polyphosphoric acid (9 eq.) is subsequently carefully added at −5° C. The reaction solution becomes pale pink in the process, and an oil deposits. The reaction is monitored via TLC (micro work-up) and subsequently carefully adjusted to pH=7-8 at low temperature using 20% NaOH. The organic phase is separated off, washed, dried and evaporated. The two isomers formed are separated by column chromatography (EA:H 9:1). The product obtained is again washed by stirring with hot heptane, giving 15 g (37%) of the product having a purity of >99.5% as a white solid.

6) Synthesis of 5,8-bisbiphenyl-4-yl-13,13-dimethyl-8,13-dihydro-5H-5,8-diazaindeno[1,2-a]anthracene A

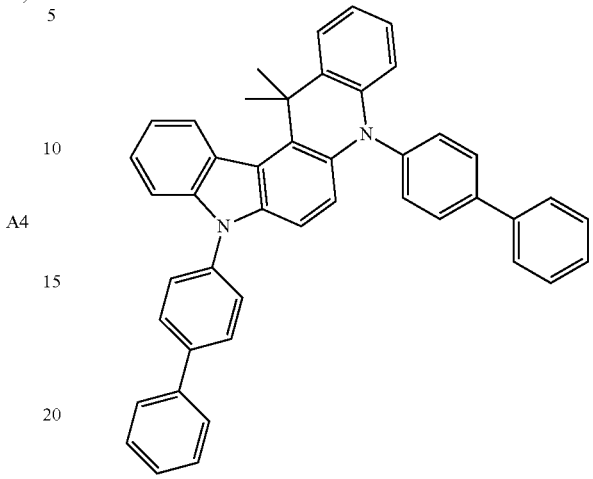

A 15 g (50.3 mmol) of the amine A5 are dissolved in degassed toluene, and 29.2 g (125.7 mmol) of 4-bromobiphenyl are added. 3.5 ml (3.52 mmol, 1 M in toluene) of tri-tert-butylphosphine, 0.45 g (2.01 mmol) of PdOAc₂ and 14.4 g (150.8 mmol) of NaOtBu are subsequently added. The mixture is heated under reflux for about 4 h, and 4-bromobiphenyl is again added if necessary. The reaction solution is allowed to cool, and water is added, whereupon the product precipitates out as a grey precipitate. The crude product is crystallised from O-dichlorobenzene, giving 20.3 g (66.9%) of the product as a yellowish solid having a purity of 99.99%.

B) Dimethyl-5,8-dinaphthalen-1-yl-8,13-dihydro-5H-5,8-diazaindeno-[1,2-a]anthracene B

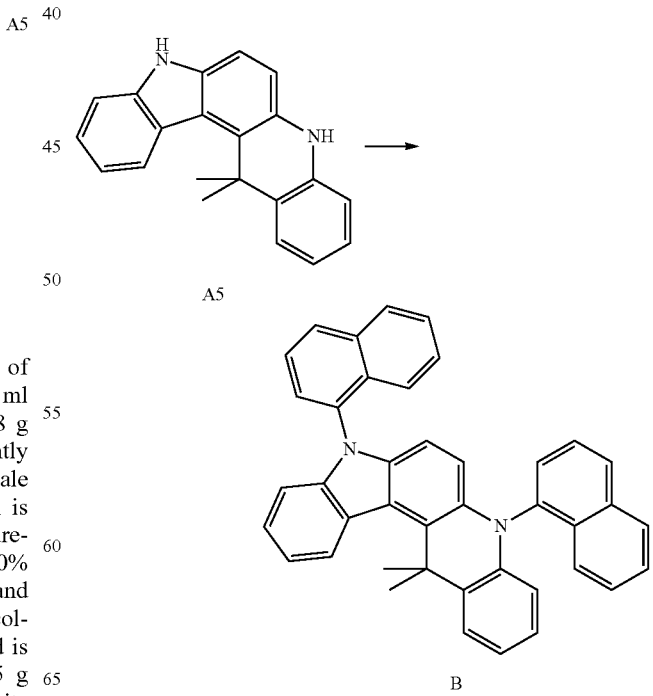

Tri-tert-butylphosphine (2.4 ml of a 1 M solution in toluene), sodium tert-butoxide (9.7 g, 101 mmol) and palladium acetate (0.3 g, 1.3 mmol) are added to a solution of 13,13-dimethyl-8,13-dihydro-5H-5,8-diazaindeno-[1,2-a]anthracene A5 (10.0 g, 34 mmol) and 1-bromonaphthalene (17.4 g, 84 mmol) in degassed xylene (200 ml), and the mixture is heated under reflux for 2 h. After the reaction mixture has cooled to room temperature, the precipitated solid is filtered off and extracted with heptane in a Soxhlet extractor. The crude product is subsequently recrystallised four times from toluene and purified by sublimation twice in vacuo ($p=5\times10^{-5}$ mbar, $T=270°$ C.).

Yield: 6.6 g (12 mmol), 35% of theory, purity >99.9% according to HPLC, colourless solid.

II. Device Examples

OLEDs according to the invention and OLEDs in accordance with the prior art are produced by a general process in accordance with WO 04/058911, which is adapted to the circumstances described here (layer-thickness variation, materials).

In Examples C1 to I5 below (see Tables 1 and 2), the data for various OLEDs are presented. Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The OLEDs basically have the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), to which the matrix material or materials is (are) admixed by co-evaporation in a certain proportion by volume. An expression such as ST1:TEG1 (90%:10%) here means that the material ST1 is present in the layer in a proportion by volume of 90% and TEG1 is present in the layer in a proportion of 10%. Analogously, the electron-transport layer may also consist of a mixture of two materials.

The OLEDs are characterised by standard methods. To this end, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), and the lifetime are determined. The electroluminescence spectrum are determined at a luminous density of 1000 cd/m², and the CIE 1931 x and y colour coordinates are calculated therefrom. The expression U1000 in Table 2 denotes the voltage required for a luminous density of 1000 cd/m². CE1000 and PE1000 denote the current and power efficiency respectively which are achieved at 1000 cd/m². Finally, EQE1000 is the external quantum efficiency at an operating luminous density of 1000 cd/m². The lifetime LT is defined as the time after which the luminous density has dropped from the initial luminous density L0 to a certain proportion L1 on operation at constant current. The expression L0=4000 cd/m² and L1=80% in Table 2 means that the lifetime indicated in column LT corresponds to the time after which the initial luminous density of the corresponding OLED has dropped from 4000 cd/m² to 3200 cd/m². The values for the lifetime can be converted into a value for other initial luminous densities with the aid of conversion formulae known to the person skilled in the art. The lifetime for an initial luminous density of 1000 cd/m² is the usual figure quoted here.

The data for the various OLEDs are summarised in Table 2. Examples C1-C3 are comparative examples in accordance with the prior art, while Examples I1-I5 show data for OLEDs comprising materials according to the invention.

Some of the examples are explained in greater detail below in order to illustrate the advantages of the compounds according to the invention. However, it should be pointed out that this only represents a selection of the data shown in Table 2.

Use of Compounds According to the Invention as Hole-transport Materials

OLEDs C1-C3 are comparative examples in accordance with the prior art in which hole-transport materials SpA1 and SpNPB are employed. Examples I1-I5 show data of OLEDs in which compounds A and B according to the invention are employed.

Use of compound B in blue-fluorescent OLEDs gives rise to an operating voltage which is reduced by 0.3 V compared with the prior art, which results in an increase from 7.1 to 7.5 lm/W with virtually unchanged current efficiency. The lifetime increases from 210 to 240 h through the use of compound B (Examples C1, I2).

In phosphorescent green OLEDs, the use of compounds according to the invention likewise gives rise to improvements with respect to voltage and power efficiency. In particular without HATCN as interlayer, the use of compound A instead of SpA1 gives rise to a significant increase in the power efficiency of virtually 15%, with the lifetime simultaneously also increasing from 360 to 410 h (Examples C3, I5).

The use of compounds according to the invention on the hole-transport side of OLEDs thus gives rise to improvements with respect to operating voltage, power efficiency and lifetime.

Use of Compounds According to the Invention as Dopants

Use of compound B in the emission layer of OLEDs gives rise to blue emission. Use of the layer structure HATCN 5 nm/SPA1 140 nm/NPB 20 nm/M1:B (95%:5%) 30 nm/ST1: LiQ (50%:50%) 20 nm with an aluminium layer with a thickness of 100 nm as cathode gives rise to deep-blue colour coordinates of CIE x/y=0.15/0.09 and an external quantum efficiency of 5.2% at 1000 cd/m². The operating voltage is 4.5 V for a luminous density of 1000 cd/m².

TABLE 1

Structure of the OLEDs

| Ex. | HIL thickness | HTL thickness | IL thickness | EBL thickness | EML thickness | HBL thickness | ETL thickness |
|---|---|---|---|---|---|---|---|
| C1 | HATCN 5 nm | SpNPB 40 nm | — | NPB 20 nm | M1:D1 (98.5%:1.5%) 30 nm | — | ST2:LiQ (50%:50%) 20 nm |
| C2 | — | SpA1 70 nm | HATCN 5 nm | BPA1 20 nm | ST1:TEG1 (90%:10%) 30 nm | ST1 10 nm | ST1:LiQ (50%:50%) 30 nm |
| C3 | — | SpA1 70 nm | — | BPA1 90 nm | IC1:TEG1 (90%:10%) 30 nm | — | ST1:LiQ (50%:50%) 40 nm |
| I1 | HATCN 5 nm | A 40 nm | — | NPB 20 nm | M1:D1 (98.5%:1.5%) 30 nm | — | ST2:LiQ (50%:50%) 20 nm |
| I2 | HATCN 5 nm | B 40 nm | — | NPB 20 nm | M1:D1 (98.5%:1.5%) 30 nm | — | ST2:LiQ (50%:50%) 20 nm |
| I3 | — | A 70 nm | HATCN 5 nm | BPA1 20 nm | ST1:TEG1 (90%:10%) 30 nm | ST1 10 nm | ST1:LiQ (50%:50%) 30 nm |
| I4 | — | B 70 nm | HATCN 5 nm | BPA1 20 nm | ST1:TEG1 (90%:10%) 30 nm | ST1 10 nm | ST1:LiQ (50%:50%) 30 nm |
| I5 | — | A 70 nm | — | BPA1 90 nm | IC1:TEG1 (90%:10%) 30 nm | — | ST1:LiQ (50%:50%) 40 nm |

TABLE 2

Data for the OLEDs

| Ex. | U1000 (V) | CE1000 (cd/A) | PE1000 (lm/W) | EQE 1000 | CIE x/y at 1000 cd/m² | L0 (cd/m²) | L1 % | LT (h) |
|---|---|---|---|---|---|---|---|---|
| C1 | 4.3 | 9.8 | 7.1 | 7.6% | 0.14/0.16 | 6000 | 50 | 210 |
| C2 | 4.2 | 52 | 39 | 14.5% | 0.36/0.60 | 4000 | 80 | 330 |
| C3 | 3.8 | 54 | 45 | 14.9% | 0.36/0.60 | 4000 | 80 | 360 |
| I1 | 4.2 | 9.9 | 7.4 | 7.7% | 0.14/0.16 | 6000 | 50 | 200 |
| I2 | 4.0 | 9.5 | 7.5 | 7.4% | 0.14/0.16 | 6000 | 50 | 240 |
| I3 | 4.0 | 52 | 41 | 14.3% | 0.36/0.60 | 4000 | 80 | 340 |
| I4 | 3.9 | 53 | 43 | 14.6% | 0.36/0.60 | 4000 | 80 | 360 |
| I5 | 3.4 | 55 | 51 | 15.3% | 0.36/0.60 | 4000 | 80 | 410 |

TABLE 3

Structural formulae of the materials for the OLEDs

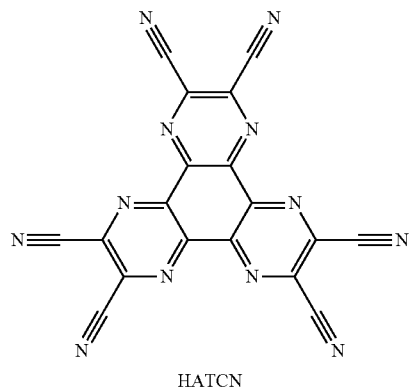

HATCN

TABLE 3-continued

Structural formulae of the materials for the OLEDs

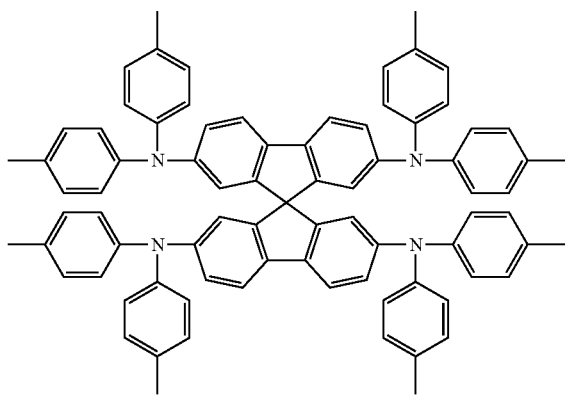

SpA1 (prior art)

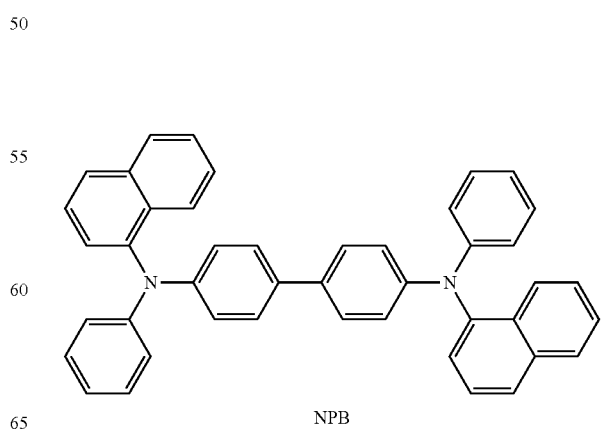

NPB

TABLE 3-continued
Structural formulae of the materials for the OLEDs
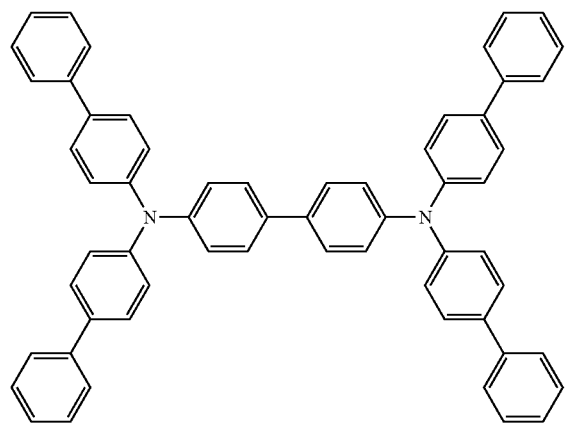
BPA1
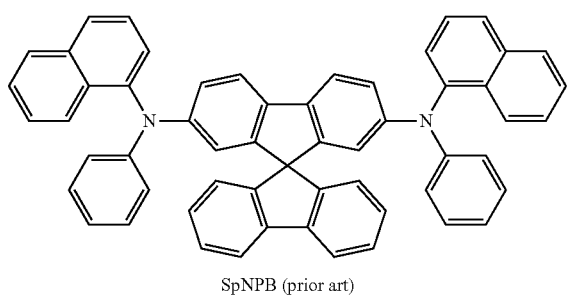 [SMILES: c1ccc(N(c2ccc3c(c2)C2(c4ccccc4-c4ccccc42)c2cc(N(c4ccccc4)c4cccc5ccccc45)ccc2-3)c2cccc3ccccc23)cc1]
SpNPB (prior art)
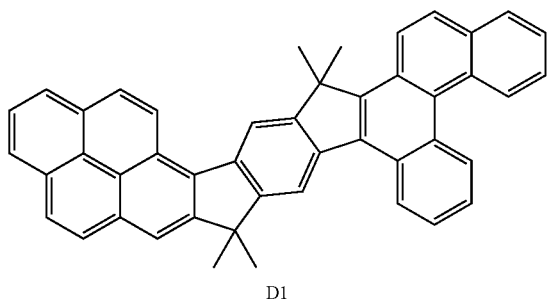
D1
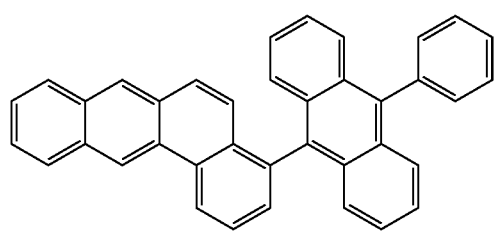
M1
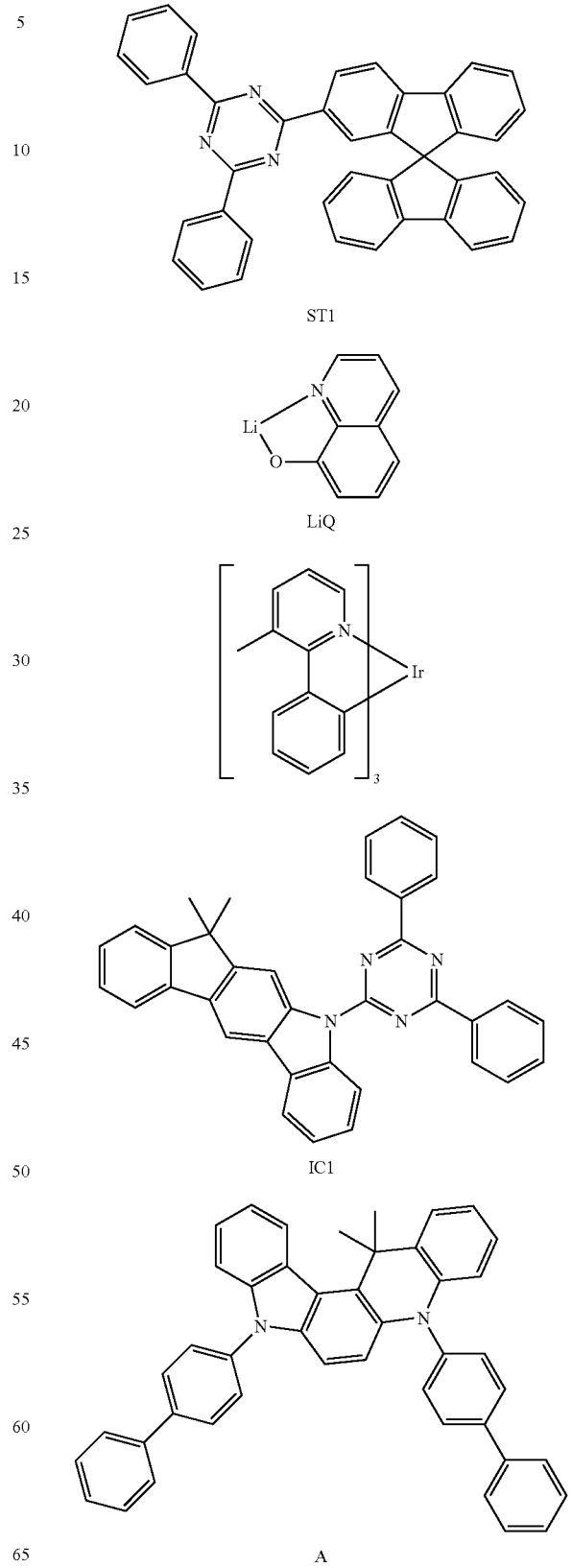
ST1
LiQ
IC1
A

TABLE 3-continued

Structural formulae of the materials for the OLEDs

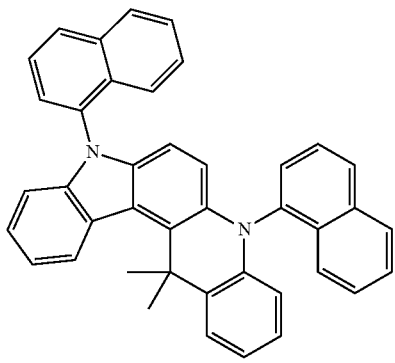

B

The invention claimed is:

1. A compound of the formula (Ia)

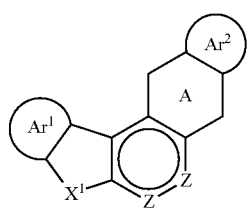

formula (I)

wherein $X^1$, $X^2$ and $X^3$ are on each occurrence a divalent group selected, identically or differently, from $BR^1$, $C(R^1)_2$, $Si(R^1)_2$, $C=NR^1$, $C=C(R^1)_2$, $NR^1$, O, S, S=O, $S(=O)_2$, $PR^1$ or $P(=O)R^1$;

Z is on each occurrence selected, identically or differently, from $CR^1$ and N;

$Ar^1$ and $Ar^2$ are on each occurrence, identically or differently, an aryl group having 6 to 60 aromatic ring atoms or a heteroaryl group having 5 to 60 aromatic ring atoms, wherein said aryl or heteroaryl group is optionally substituted by one or more radicals $R^2$;

$R^1$ and $R^2$ are on each occurrence, identically or differently,

H, D, F, CN, $Si(R^3)_3$, $N(R^3)_2$ or a straight-chainalkyl or alkoxy group having 1 to 20 C atoms or a branched or cyclic alkyl or alkoxy group having 3 to 20 C atoms, wherein said straight-chain alkyl or alkoxy group or said branched or cyclic alkyl or alkoxy group is optionally substituted by one or more radicals $R^3$, where one or more $CH_2$ groups in said straight-chain alkyl or alkoxy group or the branched or cyclic alkyl or alkoxy group is optionally replaced by —C≡C—, —$R^3$C=$CR^3$—, $Si(R^3)_2$, C=O, C=$NR^3$, —$NR^3$—, —O—, —S—, —COO— or —$CONR^3$—, or an aryl or heteroaryl group having 5 to 20 aromatic ring atoms, which may is optionally substituted by one or more radicals $R^3$, where two or more radicals $R^1$ or $R^2$ may be linked to one another and may form an aliphatic or aromatic ring system;

$R^3$ is on each occurrence, identically or differently, H, D, F, CI, Br, $B(OR^4)_2$, CHO, $C(O)R^4$, $CR^4=C(R^4)_2$, CN, $COOR^4$, $CON(R^4)_2$, $Si(R^4)_3$, $N(R^4)_2$, $NO_2$, $P(=O)(R^4)_2$, $OSO_2R^4$, OH, $S(=O)R^4$, $S(=O)_2R^4$, a straight-chainalkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, wherein said straight-chainalkyl, alkoxy or thioalkyl group or said branched or cyclic alkyl, alkoxy or thioalkyl group is optionally substituted by one or more radicals $R^4$, where one or more $CH_2$ groups in said straight-chainalkyl, alkoxy or thioalkyl group or said branched or cyclic alkyl, alkoxy or thioalkyl group is optionally replaced by —$R^4C=CR^4$—, —C≡C—, $Si(R^4)_2$, $Ge(R^4)_2$, $Sn(R^4)_2$, C=O, C=S, C=Se, C=$NR^4$, —COO—, —$CONR^4$—, $NR^4$, $P(=O)(R^4)$, —O—, —S—, SO or $SO_2$ and where one or more H atoms is optionally replaced by D, F, CI, Br, I, CN or $NO_2$, or an aromatic or heteroaromatic ring system having 5 to 60 aromatic ring atoms, said aromatic or heteroaromatic ring system is optionally substituted by one or more radicals $R^4$, or an aryloxy or heteroaryloxy group having 5 to 60 aromatic ring atoms, which is optionally substituted by one or more radicals $R^4$ where two or more radicals $R^3$ is optionally linked to one another and may form an aliphatic or aromatic ring system;

$R^4$ is, identically or differently on each occurrence, H, D, F or an aliphatic, aromatic and/or heteroaromatic organic radical having 1 to 20 C atoms, in which, in addition, one or more H atoms in said organic radical is optionally replaced by D or F; two or more identical or different substituents $R^4$ here is optionally linked to one another and form an aliphatic or aromatic ring system;

and with the proviso that all three groups $X^1$, $X^2$ and $X^3$ do not simultaneously represent O, that all three groups $X^1$, $X^2$ and $X^3$ do not simultaneously represent S, and that, if one or more of the groups $X^1$, $X^2$ and $X^3$ represent a group of the formula $NR^1$, Was a constituent of the group $NR^1$ is an aryl or heteroaryl group having 5 to 20 aromatic ring atoms, which may in each case be substituted by one or more radicals $R^3$.

2. The compound according to claim 1, wherein $X^1$, $X^2$ and $X^3$ are on each occurrence, identically or differently, selected from $C(R^1)_2$, $NR^1$, O or S and with the proviso that all three groups $X^1$, $X^2$ and $X^3$ do not simultaneously represent O, that all three groups $X^1$, $X^2$ and $X^3$ do not simultaneously represent S and that, if one or more of the groups $X^1$, $X^2$ and $X^3$ represent a group of the formula $NR^1$, $R^1$ as a constituent of the group $NR^1$ is an aryl or heteroaryl group having 5 to 20 aromatic ring atoms, which may in each case be substituted by one or more radicals $R^3$.

3. The compound according to claim 1, wherein the groups $Ar^1$ and $Ar^2$ are selected on each occurrence, identically or differently, from the following groups:

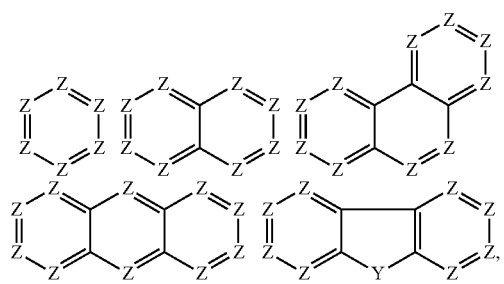

where the groups is optionally fused to the remainder of the compound via any desired bond Z—Z, where these Z cannot be equal to N, Z is otherwise as defined in claim 1, and furthermore Y is selected on each occurrence, identically or differently, from $C(R^2)_2$, C=O, $NR^2$, O, S, S=O or $S(=O)_2$.

4. The compound according to claim 3, wherein not more than three groups Z per aromatic ring are equal to N and the remaining groups Z are equal to $CR^1$.

5. A formulation comprising at least one compound according to claim 1 and at least one solvent.

6. An electronic device which comprises the compound according to claim 1.

7. The electronic device according to claim 6, wherein the device is an organic electroluminescent device (OLED).

8. The electronic device according to claim 6, wherein the device is an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC), an organic laser diode (O-laser) or an organic electroluminescent device (OLED).

9. An electronic device which comprises the compound according to claim 1 is employed as a hole-transport material in a hole-transport layer or a hole-injection layer or is employed as a matrix material in an emitting layer or is employed as dopant in an emitting layer.

* * * * *